(12) United States Patent
Boltje et al.

(10) Patent No.: US 11,639,364 B2
(45) Date of Patent: May 2, 2023

(54) POTENT SIALYLTRANSFERASE INHIBITORS

(71) Applicant: STICHTING RADBOUD UNIVERSITEIT, Nijmegen (NL)

(72) Inventors: Thomas Jan Boltje, Doorn (NL); Torben Heise, Lyons (FR); Johan Franciscus Adrianus Pijnenborg, Nijmegen (NL); Christian Büll, Copenhagen (DK); Gosse Jan Adema, Groesbeek (NL)

(73) Assignees: STICHTING RADBOUD UNIVERSITEIT, Nijmegen (NL); STICHTING RADBOUD UNIVERSITAIR MEDISCH CENTRUM, Nijmegen (NL)

( * ) Notice: Subject to any disclaimer, the term of this patent is extended or adjusted under 35 U.S.C. 154(b) by 0 days.

(21) Appl. No.: 16/965,023

(22) PCT Filed: Jan. 29, 2019

(86) PCT No.: PCT/EP2019/052116
§ 371 (c)(1),
(2) Date: Jul. 27, 2020

(87) PCT Pub. No.: WO2019/145562
PCT Pub. Date: Aug. 1, 2019

(65) Prior Publication Data
US 2021/0107931 A1 Apr. 15, 2021

(30) Foreign Application Priority Data
Jan. 29, 2018 (EP) ..................................... 18153972

(51) Int. Cl.
*C07H 13/12* (2006.01)
*C07H 13/04* (2006.01)

(52) U.S. Cl.
CPC ............. *C07H 13/12* (2013.01); *C07H 13/04* (2013.01)

(58) Field of Classification Search
CPC ............................... C07H 13/12; C07H 13/04
See application file for complete search history.

(56) References Cited

FOREIGN PATENT DOCUMENTS

| EP | 2591787 A1 | 5/2013 |
|---|---|---|
| WO | WO2008/068638 A2 | 6/2008 |
| WO | WO2015/148915 A1 | 10/2015 |
| WO | WO2016/071431 A1 | 5/2016 |

OTHER PUBLICATIONS

Heise et al., J. Med. Chem., 2019, 62, p. 1014-1021, Published: Dec. 13, 2018. (Year: 2018).*
Suzuki et al., Carbohydrate Research, 2015, 406, p. 1-9. (Year: 2015).*
Definition of prevent, Oxford English Dictionary Online, http://dictionary.oed.com/, accessed online Mar. 27, 2010, especially definition 9a. at p. 2. (Year: 2010).*
Krausslich et al., Antiviral Strategies, Handbook of Experimental Pharmacology, 2009, Springer-Verlag Berlin Heidelberg, p. 1-24. (Year: 2009).*
Vogel, V.G., Cancer J. Clin., 2000, 50, p. 156-170. (Year: 2000).*
Karam et al., Critical Care, 2016, 20, article No. 136, 9 pages. (Year: 2016).*
Rémi Szabo et al: "Advancement of Sialyltransferase Inhibitors: Therapeutic Challenges and Opportunities : Sialyltransferase Inhibitors". Medicinal Research Reviews, vol. 37, No. 2, Mar. 1, 2017, pp. 219-270.
Michelle A Sparks et al: "Synthesis of potential inhibitors of hemagglutination by influenza virus: chemoenzymic preparation of N-5 analogs of N-acetylneuraminic acid". Tetrahedron, Jan. 1, 1993, pp. 1-12.
Susanne Johansson et al: Synthesis, and Evaluation of N-Acyl Modified Sialic Acids as Inhibitors of Adenoviruses Causing Epidemic Keratoconjunctivitis +, Journal of Medicinal Chemistry, vol. 52. No. 12. Jun. 25, 2009, pp. 3666-3678.
N. Drinnan et al: "Inhibitors of Sialyl transferases: Potential Roles in Tumor Growth and Metastasis", Mini Reviews in Medicinal Chemistry, vol. 3, No. 6, Sep. 1, 2003, pp. 501-517.
Stefanie Mesch et al: Low Molecular Weight Antagonists of the Myelin-Associated Glycoprotein: Synthesis, Docking, and Biological Evaluation, Journal of Medicinal Chemistry, vol. 53, No. 4, Feb. 25, 2010, pp. 1597-1615.
Torben Heise et al:Potent Metabolic Sialylation Inhibitors Based on C-5-Modified Fluorinated Sialic Acids, Journal of Medicinal Chemistry, vol. 62, No. 2, Dec. 13, 2018, pp. 1014-1021.
Adams, David, and William A. Gahl. "Free sialic acid storage disorders." GeneReviews®[Internet], University of Washington, Seattle, 2013.
Almaraz, Ruben T., et al. "Metabolic oligosaccharide engineering with N-Acyl functionalized ManNAc analogs Cytotoxicity, metabolic flux, and glycan-display considerations." Biotechnology and bioengineering 109.4 (2012): 992-1006.
Angata, Takashi, and Ajit Varki. "Chemical diversity in the sialic acids and related α-keto acids: an evolutionary perspective." Chemical reviews 102.2 (2002): 439-470.
Bode, Christian, et al. "CpG DNA as a vaccine adjuvant." Expert review of vaccines 10.4 (2011): 499-511.
Büll, Christian, et al. "Targeting aberrant sialylation in cancer cells using a fluorinated sialic acid analog impairs adhesion, migration, and in vivo tumor growth." Molecular cancer therapeutics 12.10 (2013): 1935-1946.

(Continued)

*Primary Examiner* — Jonathan S Lau
(74) *Attorney, Agent, or Firm* — N.V. Nederlandsch Octrooibureau

(57) ABSTRACT

The present invention relates to a new class of sialyltransferase inhibitors. The class features a carbamate or similar moiety on the amine of a neuraminic acid derivative. Such inhibitors are suitable for use as a medicament, for example for treating, preventing, or delaying bacterial infection, viral infection, cancer, a disorder of sialic acid metabolism, or an autoimmune disease.

12 Claims, 9 Drawing Sheets

(56) References Cited

OTHER PUBLICATIONS

Figure 1:
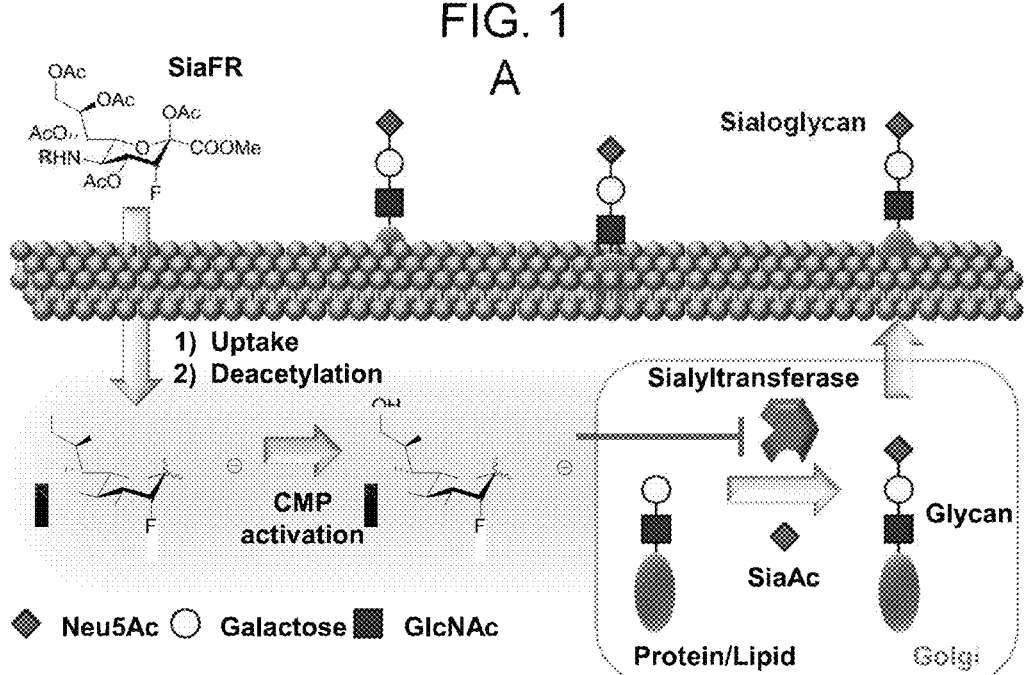
Figure 1:
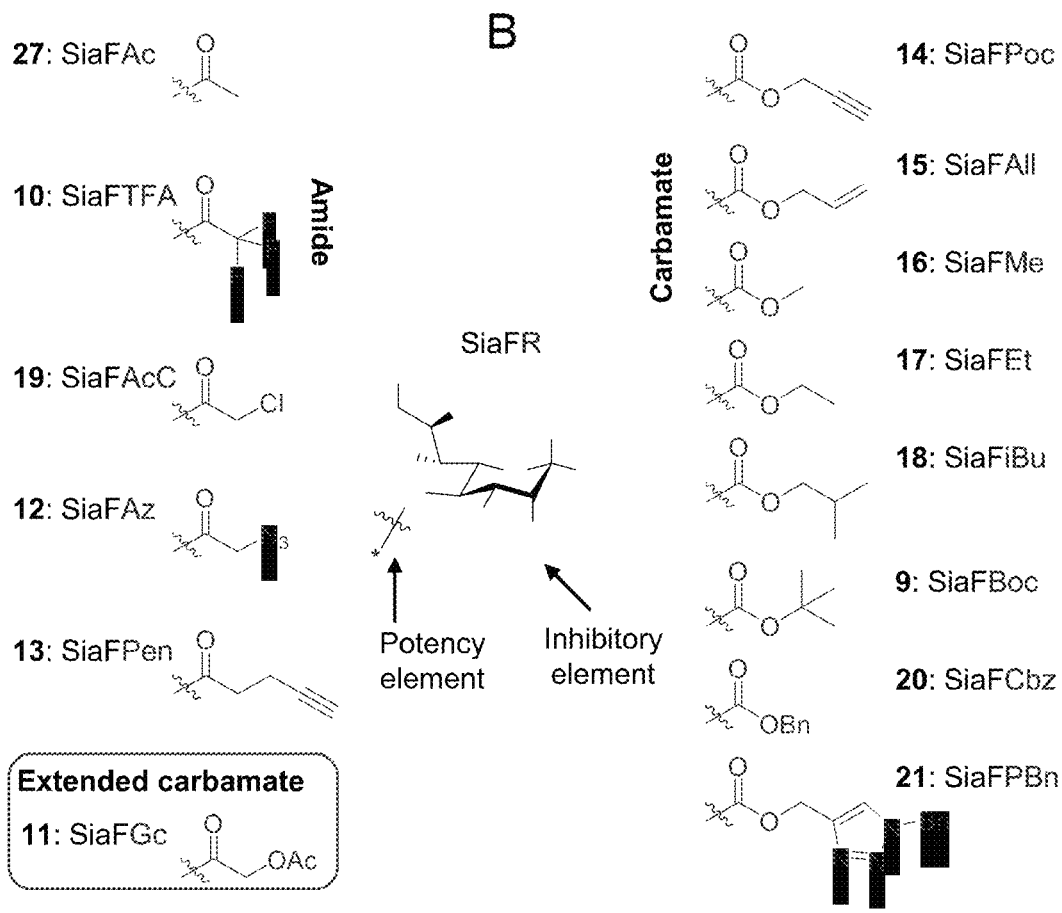

Büll, Christian, Martijn H. den Brok, and Gosse J. Adema. "Sweet escape: sialic acids in tumor immune evasion." Biochimica et Biophysics Acta (BBA)-Reviews on Cancer 1846.1 (2014): 238-246.
Büll, Christian, et al. "Sialic acids sweeten a tumor's life." Cancer research 74.12 (2014): 3199-3204.
Büll, Christian, et al. "Targeted delivery of a sialic acid-blocking glycomimetic to cancer cells inhibits metastatic spread." ACS nano 9.1 (2015): 733-745.
Büll, Christian, et al. "Sialic acid glycoengineering using an unnatural sialic acid for the detection of sialoglycan biosynthesis defects and on-cell synthesis of Siglec ligands." ACS chemical biology 10.10 (2015): 2353-2363.
Büll, Christian, et al. "Sialic acid mimetics to target the sialic acid—Siglec axis." Trends in biochemical sciences 41.6 (2016): 519-531.
Chao, Chin-Sheng, et al. "Versatile acetylation of carbohydrate substrates with bench-top sulfonic acids and application to one-pot syntheses of peracetylated thioglycosides." Carbohydrate research 343.5 (2008): 957-964.
Kroesen, Michiel, et al. "A transplantable TH-MYCN transgenic tumor model in C57BI/6 mice for preclinical immunological studies in neuroblastoma." International journal of cancer 134.6 (2014): 1335-1345.
Ley, Klaus. "The role of selectins in inflammation and disease." Trends in molecular medicine 9.6 (2003): 263-268.
Macauley, Matthew S., Paul R. Crocker, and James C. Paulson. "Siglec-mediated regulation of immune cell function in disease." Nature Reviews Immunology 14.10 (2014): 653-666.
Pagan, Jose D., Maya Kitaoka, and Robert M. Anthony. "Engineered sialylation of pathogenic antibodies in vivo attenuates autoimmune disease." Cell 172.3 (2018): 564-577.
Rillahan, Cory D., et al. "Global metabolic inhibitors of sialyl-and fucosyltransferases remodel the glycome." Nature chemical biology 8.7 (2012): 661-668.
Stauffer, Jimmy K., et al. "High-throughput molecular and histopathologic profiling oftumortissue in a novel transplantable model of murine neuroblastoma: new tools for pediatric drug discovery." Cancer investigation 30.5 (2012): 343-363.
Stencel-Baerenwald, Jennifer E., et al. "The sweet spot: defining virus-sialic acid interactions." Nature Reviews Microbiology 12.11 (2014): 739-749.
Volkers, Gesa, et al. "Structure of human STSSialII sialyltransferase provides insight into cell-surface polysialylation." Nature structural & molecular biology 22.8 (2015): 627-635.
Yin, Bojiao, et al. "A novel sugar analog enhances sialic acid production and biotherapeutic sialylation in CHO cells." Biotechnology and Bioengineering 114.8 (2017): 1899-1902.
Burkart, Michael D., et al. "A new method for the synthesis of fluoro-carbohydrates and glycosides using selectfluor." Journal of the American Chemical Society 119.49 (1997): 11743-11746.
Burkart, Michael D., Stephane P. Vincent, and Chi-Huey Wong. "An efficient synthesis of CMP-3-fluoroneuraminic acid." Chemical Communications 16 (1999): 1525-1526.

\* cited by examiner

A

B

A

B

A

B

POTENT SIALYLTRANSFERASE INHIBITORS

FIELD OF THE INVENTION

The present invention relates to a new class of sialyltransferase inhibitors. The class features a carbamate or similar moiety on the amine of a neuraminic acid derivative. Such inhibitors are suitable for use as a medicament, for example for treating, preventing, or delaying bacterial infection, viral infection, cancer, or a disease or condition associated with over sialylation such as metabolic disorders, cancer, or autoimmune diseases.

BACKGROUND ART

Sialic acids are complex nine-carbon sugars abundantly expressed at the termini of cell surface glycans and on secreted glycoproteins (Angata and Varki, 2002, DOI: 10.1021/cr000407m). The electronegative charge of sialic acids can facilitate the binding and transport of ions, the stabilization of proteins and membranes and enhance the viscosity of mucins (Varki and Schauer, 2009, PMID: 20301246). Additionally, they mask underlying galactose residues thereby regulating protein half-life and recycling. Moreover, sialic acids are recognized by a variety of endogenous immunoregulatory receptors such as Siglecs (Büll et al., 2016, doi: 10.1016/j.tibs.2016.03.007, Macauley et al., 2014, doi: 10.1038/nri3737) and Selectins (Ley, 2003, DOI: 10.1016/S1471-4914(03)00071-6). Sialic acids therefore play an important role in physiological processes. However, the (over)expression of sialic acid is also associated with disease (WO2016071431). For example, pathogenic bacteria have evolved to express sialic acids on their cell surface for immune evasion whilst viruses can utilize sialic acids to gain entry into host tissue. Furthermore, cancer cells overexpress sialic acids which has been linked to immune evasion (Büll et al., 2014, DOI: 10.1016/j.bbcan.2014.07.005), improved extravasation, metastasis and resistance to chemo- and radiotherapy (Büll et al., 2014, DOI: 10.1158/0008-5472.CAN-14-0728). Abolishing sialic acid expression in these cases is therefore a promising therapeutic avenue. This can be achieved by the use of sialidases, enzymes that cleave extracellular sialic acid, but these are often contaminated, immunogenic, and the effect is short-lived since the sialic acid biosynthesis is unaffected (Sedlacek and Seiler, 1978, DOI: 10.1007/BF00199623). Small molecule inhibitors of the sialic acid biosynthesis can overcome these issues.

The most common sialic acid derivative found in humans is N-acetylneuraminic acid (NeuNAc), which is biosynthesized from N-acetylmannosamine (ManNAc). NeuNAc is then CMP-activated (CMP-NeuNAc), in the nucleus, transported to the Golgi and transferred onto glycoconjugates. The transfer is catalyzed by a family of 20 Golgi-resident sialyltransferases (STs) which are substrate and linkage specific resulting in a variety of α2,3-, α2,6-, and α2,8-linked sialosides (Varki and Schauer, 2009, PMID: 20301246). Fluorinated substrates such as 3Fax-Neu-CMP are known to be competitive ST inhibitors (Burkart et al., 1999, DOI: 10.1039/A903362; Volkers et al., 2015, doi: 10.1038/nsmb.3060; WO2015148915). These compounds are, however, not cell-permeable and hence not active in cell culture and in vivo. This hurdle was recently overcome by feeding a peracetylated metabolic precursor (P-3Fax-NeuNAc, see FIG. 1) (Rillahan et al., 2012, DOI: 10.1038/nchembio.999). This metabolic precursor can passively diffuse over the cell membrane, after which it is deacetylated by esterases and CMP-activated by CMAS to afford the active 3Fax-Neu-CMP in situ. The inventors have previously shown that such inhibitors are effective in vitro and in vivo and can be used to combat oversialylation in tumor models (Büll et al., 2013, DOI: 10.1158/1535-7163.MCT-13-0279; Büll et al., 2015, DOI: 10.1021/nn5061964).

However, during these studies it was found that P-3Fax-NeuNAc is not equally potent across different cell lines. There is a need for sialyltransferase inhibitors with an increased potency.

SUMMARY OF THE INVENTION

In a first aspect the invention provides a compound of general formula (I):

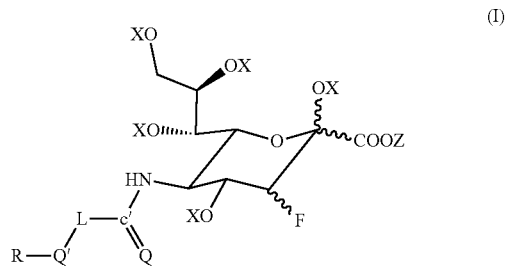

wherein X is in each instance independently chosen from the group consisting of hydrogen and a linear, branched, or cyclic $C_{1-6}$ acyl moiety wherein each carbon atom is optionally substituted by a halogen, an alkoxy, or a haloalkoxy moiety, and wherein the acyl chain is optionally unsaturated; Z is chosen from the group consisting of hydrogen and a linear, branched, or cyclic $C_{1-6}$ alkyl, alkenyl, or alkynyl moiety wherein each carbon atom is optionally substituted by a halogen, an alkoxy, or a haloalkoxy moiety; Q and Q' are each independently chosen from the group consisting of O, S, and NH; c' is C; or optionally when Q is O, c' is C or S(=O), and Q' can be absent when c' is S(=O); L is either —$CH_2$— or is absent; and R is a linear, branched, or cyclic $C_{1-6}$ hydrocarbon moiety, preferably an alkyl, alkenyl, or alkynyl moiety, wherein each carbon atom is optionally substituted by a halogen, an alkoxy, a haloalkoxy, a hydroxyl, or an oxo moiety, or optionally R is H when c' is S(=O), L is absent, and Q' is not absent; wherein the compound is not of general formula (I) wherein Z is methyl, Q is O, Q' is O, L is absent, R is tert-butyl, X at the anomeric position is axial and is H, and each other X is acetyl. In preferred embodiments, the fluor is axial. In preferred embodiments, the fluor is equatorial. In preferred embodiments, L is absent.

In preferred embodiments of this aspect, the compound is provided wherein X is in each instance chosen from the group consisting of acetyl, propionyl, and butyryl, preferably X is acetyl; and/or Z is chosen from the group consisting of methyl, ethyl, n-propyl, isopropyl, cyclopropyl, allyl, propargyl, n-butyl, tert-butyl, sec-butyl, isobutyl, and cyclobutyl, preferably Z is methyl; and/or Q is chosen from the group consisting of O and S, preferably Q is O; and/or Q' is chosen from the group consisting of O, S, and NH, or Q is absent when c' is S(=O); preferably Q' is O or is absent when c' is S(=O), most preferably Q' is O; and/or c' is C or when Q is O, c' is C or S(=O); and/or L is absent; and/or R is a linear, branched, or cyclic $C_{1-6}$ hydrocarbon moiety, preferably an alkyl, alkenyl, or alkynyl moiety, wherein each carbon atom is optionally substituted by a halogen, an alkoxy, a haloalkoxy, a hydroxyl, or an oxo moiety, preferably R is chosen from the group consisting of methyl, ethyl, isobutyl, tert-butyl, n-butyl, allyl, propargyl, acetyl, 2-methoxyethyl, 2,2,2-trichloroethyl, and 2-fluoroethyl. It is further preferred that c' be C.

In a second aspect the invention provides a compound of general formula (I) wherein X is in each instance independently chosen from the group consisting of hydrogen and a linear, branched, or cyclic $C_{1-6}$ acyl moiety wherein each carbon atom is optionally substituted by a halogen, an alkoxy, or a haloalkoxy moiety, and wherein the acyl chain is optionally unsaturated; Z is chosen from the group consisting of hydrogen and a linear, branched, or cyclic $C_{1-6}$ alkyl, alkenyl, or alkynyl moiety wherein each carbon atom is optionally substituted by a halogen, an alkoxy, or a haloalkoxy moiety; Q and Q' are each independently chosen from the group consisting of O, S, and NH; c' is C; or optionally when Q is O, c' is C or S(=O), and Q' can be absent when c' is S(=O); L is either —$CH_2$— or is absent; and R is a linear, branched, or cyclic $C_{1-6}$ hydrocarbon moiety, preferably an alkyl, alkenyl, or alkynyl moiety, wherein each carbon atom is optionally substituted by a halogen, an alkoxy, a haloalkoxy, a hydroxyl, or an oxo moiety, or optionally R is H when c' is S(=O), L is absent, and Q' is not absent; for use as a medicament. The medicament is preferably for use in treating, preventing, or delaying bacterial infection, viral infection, cancer, a disorder of sialic acid metabolism, or an autoimmune disease.

In a third aspect the invention provides a composition comprising a compound as defined above and a pharmaceutically acceptable excipient. The composition can be for use as a medicament, preferably for use in treating, preventing, or delaying bacterial infection, viral infection, cancer, a congenital glycosylation disorder, or an autoimmune disease.

In a fourth aspect the invention provides an in vitro method for inhibiting sialyltransferase, the method comprising the step of contacting the sialyltransferase with a compound as defined in any one of the other aspects, or with a composition as defined in another aspect. In a preferred embodiment is provided the method, wherein the sialyltransferase is in a cell, wherein the method comprises the additional steps of: i) contacting the cell with the compound or composition; and ii) allowing the compound to passively diffuse into the cell, and/or to be actively taken up by the cell; wherein for the compound preferably X is not hydrogen, and/or preferably Z is not hydrogen.

Preferably the method reduces sialylation of the cell. Preferably the cell is a cancer cell or a bacterial cell.

In a fifth aspect the invention provides a method of producing a sialic acid biosynthesis inhibitor, the method comprising the steps of: i) providing a neuraminic acid derivative comprising an equatorial free amine at C-5 and comprising fluorine at C-3, preferably comprising axial fluorine at C-3; ii) reacting the free amine at C-5 with a compound of general formula (IV):

(IV)

$$\underset{Y}{\overset{Q}{\underset{\|}{\text{c'}}}}\text{—L—Q'—R}$$

wherein Q and Q' are each independently chosen from the group consisting of O, S, and NH; c' is C; or optionally when Q is O, c' is C or S(=O), and Q' can be absent when c' is S(=O); L is either —$CH_2$— or is absent; R is a linear, branched, or cyclic $C_{1-6}$ hydrocarbon moiety, preferably an alkyl, alkenyl, or alkynyl moiety, wherein each carbon atom is optionally substituted by a halogen, an alkoxy, a haloalkoxy, a hydroxyl, or an oxo moiety, or optionally R is H when c' is S(=O), L is absent, and Q' is not absent; and Y is a hydroxyl moiety, a halogen, or a condensed leaving group preferably selected from the group consisting of N-hydroxysuccinimide, sulfo-N-hydroxysuccinimide, 4-nitrophenol, pentafluorophenol, imidazole, 1-hydroxybenzotriazole, and —O-c'(=Q)-L-Q'-R; iii) optionally isolating the sialic acid biosynthesis inhibitor.

DESCRIPTION OF EMBODIMENTS

The inventors set out to improve the inhibitory potency of P-3Fax-NeuNAc by introducing modifications on the sialic acid scaffold, to produce new sialic acid biosynthesis inhibitors. C-5 modified sialic acid substrates were investigated. Different fluorinated sialic acid analogues were designed, synthesized and tested in various cell lines. To inhibit sialic acid incorporation a small library of fluorine sialic acid based sialyltransferase inhibitors was explored using a novel synthetic route. Surprisingly, it was found that more heteroatom-rich C-5 groups such as C-5 carbamates and extended carbamates and optionally sulfonates were more potent than C-5 amides, and small hydrophobic substituents further increased this potency. A decrease in $EC_{50}$ of up to 26 fold (1 μM) was obtained compared to the natural C-5 acetamide inhibitor. The inhibitors increased inhibition of 2,3-linkage over 2,6-linkage specific sialyltransferases. Moreover, the new inhibitors showed high potency on an array of different cell lines, such as cancer cell lines as well as primary cells.

Accordingly, in a first aspect the invention provides a compound of general formula (I):

(I)

[chemical structure of formula (I)]

wherein

X is in each instance independently chosen from the group consisting of hydrogen and a linear, branched, or cyclic $C_{1-6}$ acyl moiety wherein each carbon atom is optionally substituted by a halogen, an alkoxy, or a haloalkoxy moiety, and wherein the acyl chain is optionally unsaturated; preferably the $C_{1-6}$ acyl moiety is a $C_{2-4}$ acyl moiety;

Z is chosen from the group consisting of hydrogen and a linear, branched, or cyclic $C_{1-6}$ alkyl, alkenyl, or alkynyl moiety wherein each carbon atom is optionally substituted by a halogen, an alkoxy, or a haloalkoxy moiety;

Q and Q' are each independently chosen from the group consisting of O, S, and NH;

c' is C; or optionally when Q is O, c' is C or S(=O), and Q' can be absent when c' is S(=O);

L is either —CH$_2$— or is absent; and

R is a linear, branched, or cyclic C$_{1-6}$ hydrocarbon moiety, preferably an alkyl, alkenyl, or alkynyl moiety, wherein each carbon atom is optionally substituted by a halogen, an alkoxy, a haloalkoxy, a hydroxyl, or an oxo moiety, or optionally R is H when c' is S(=O), L is absent, and Q' is not absent;

wherein the compound is not of general formula (I) wherein Z is methyl, Q is O, Q' is O, L is absent, R is tert-butyl, X at the anomeric position is axial and is H, and each other X is acetyl. This latter compound is shown below.

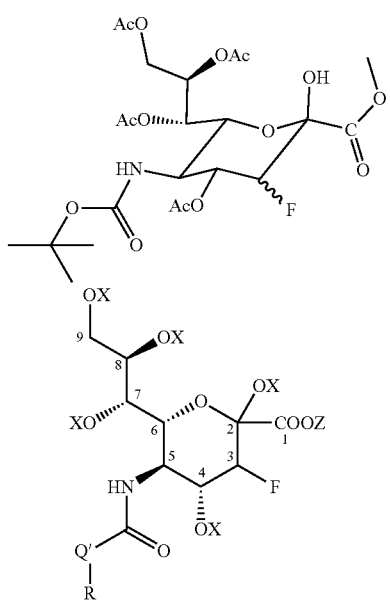

Compound of general formula (I) wherein Z is methyl, Q is O, Q' numbering is O, L is absent, R is tert-butyl, X at the anomeric position is axial and is H, and each other X is acetyl Compounds according to the first aspect of the invention are referred to hereinafter as compounds according to the invention. Preferably, c' is C and Q and Q' are each independently chosen from the group consisting of O, S, and NH. For compounds according to the invention, the anomeric position is position C-2, as it is the hemiketal carbon. The numbering is shown above in a compound where c' is C and L is absent.

For preferred compounds according to the invention, R is not CH$_3$ when X and Z are all H, and Q is O, and c' is S(=O), and Q' and L are absent. For preferred compounds according to the invention, R is not CH$_2$CH$_3$ when X and Z are all H, and Q is O, and c' is S(=O), and Q' and L are absent, more preferably R is not CH$_3$ or CH$_2$CH$_3$ for these compounds.

The fluorine atom at the C-3 position is the inhibitory element that blocks the action of sialyltransferase enzymes. This fluorine can be either axial or equatorial, or both (in a racemic mixture, or in a mixture with any enantiomeric excess). Accordingly, preferred embodiments of the invention provide the compound according to the invention, wherein it is of general formula (II-ax) or (II-eq):

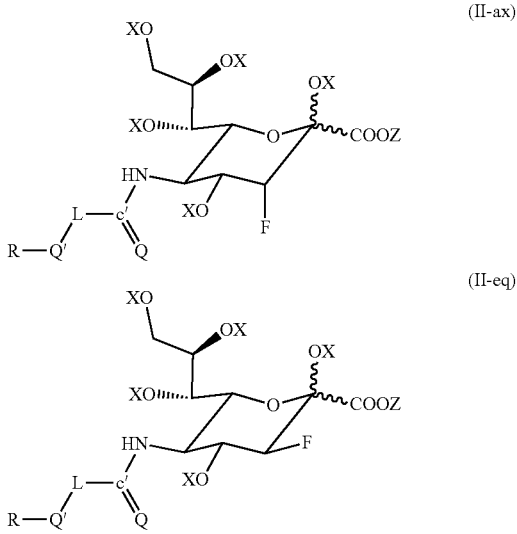

wherein each of X, Z, Q, Q', c', L, and R are as defined above. In preferred embodiments, the compound according to the invention is of general formula (II-eq), wherein each of X, Z, Q, Q', c', L, and R are as defined above, preferably wherein c' is C. In more preferred embodiments, the compound according to the invention is of general formula (II-ax) wherein each of X, Z, Q, Q', c', L, and R are as defined above, preferably wherein c' is C.

At the anomeric position, the —OX and the —COOZ moiety are not stereochemically defined. This is because their respective axial or equatorial positions can be interchanged through anomerisation. Under physiological conditions, the —OX and —COOZ can anomerise spontaneously. The isolated compound does not anomerise this rapidly. Therefore, the invention also encompasses stereochemically pure epimers of compounds of general formula (I), or of compounds of general formula (II-ax), or of compounds of general formula (II-eq). Accordingly, this aspect provides a compound of general formula (I) wherein X at the anomeric position is axial. In preferred embodiments, this aspect provides a compound of general formula (II-eq) wherein X at the anomeric position is axial. In more preferred embodiments, this aspect provides a compound of general formula (II-ax) wherein X at the anomeric position is axial. Accordingly, this aspect provides a compound of general formula (I) wherein X at the anomeric position is equatorial. In preferred embodiments, this aspect provides a compound of general formula (II-eq) wherein X at the anomeric position is equatorial. In more preferred embodiments, this aspect provides a compound of general formula (II-ax) wherein X at the anomeric position is equatorial.

Compounds according to the invention are alfa-heteroatomic or beta-heteroatomic derivatives of 3-fluorinated neuraminic acid, or optionally sulphonamide derivatives. For example, when Q and Q' are each oxygen and c' is carbon, these compounds form carbamates or extended carbamates. In this context, an extended carbamate is similar to a carbamate, but with a methylene moiety inserted in between the carbonyl moiety and the donor alcohol; or in other words, an extended carbamate is the class of compounds of general formula (I) wherein L is —CH$_2$— while both Q and Q' are oxygen and c' is carbon. The same holds mutatis mutandis for extended urea (Q is O, Q' is NH, c' is C, L is —CH$_2$—) and for extended thiocarbamate (one of Q and Q' is S, the other of Q and Q' is O, c' is C, L is —CH$_2$—) and for other compounds wherein L is —CH$_2$—. In brief, an extended analogue is an analogue wherein L is —CH$_2$—. Preferred compounds according to the invention are not extended, and accordingly preferred embodiments provide the compound according to the invention, wherein it is of general formula (III):

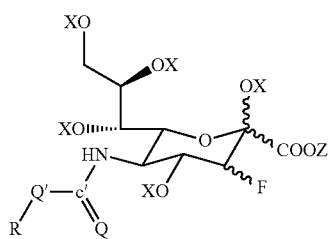
(III)

wherein each of X, Z, Q, Q', c', and R are as defined above.

The compounds according to the invention, preferably those of general formula (III), can be carbamates (Q and Q' are both O, c' is C), dithiocarbamates (Q and Q' are both S, c' is C), guadinines (Q and Q' are both NH, c' is C), thiocarbamates (one of Q and Q' is S, the other of Q and Q' is O, c' is C) which can be O-organyl thiocarbamates (Q is S, Q' is O, c' is C) or S-organyl thiocarbamates (Q is O, Q' is S, c' is C), ureas (Q is O, Q' is NH, c' is C), isoureas (Q is NH, Q' is O, c' is C), thioureas (Q is S, Q' is NH, c' is C), and isothioureas (Q is NH, Q' is S, c' is C), and optionally sulphonamides (Q is O, Q' is absent, c' is S(=O)). Preferred compounds according to the invention are carbamates, ureas, thiocarbamates, and thioureas, and optionally sulphonamides. More preferred compounds according to the invention are carbamates, sulphonamides, ureas, and thiocarbamates.

When c' is C, compounds according to the invention are of general formula I-c:

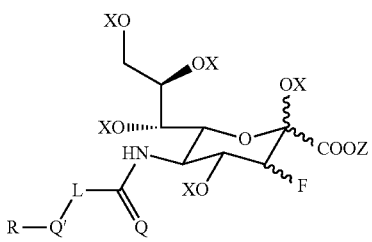
(I-c)

wherein each of X, Z, Q, L, and R are as defined above, and Q' is chosen from the group consisting of O, S, and NH. In compounds of general formula-c, Q' cannot be absent, and R cannot be H, because c' is C. Preferred compounds according to the invention are of general formula I-c. Preferred compounds of general formula I-c are carbamates, ureas, thiocarbamates, or thioureas, and optionally extended versions thereof; more preferably they are carbamates, ureas, or thiocarbamates.

When c' is (S=O), compounds according to the invention are preferably of general formula I-s:

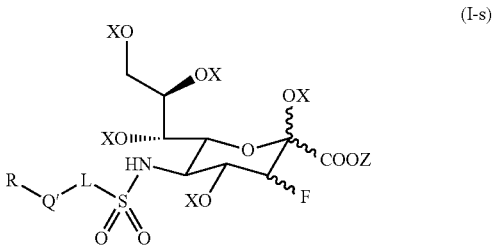
(I-s)

wherein each of X, Z, L, Q', and R are as defined above. In compounds of general formula I-s, L is preferably absent. In compounds of general formula I-s, Q' is preferably O or absent, most preferably absent. Preferred compounds according to the invention are of general formula I-s, more preferably wherein R is a linear, branched, or cyclic $C_{1-5}$, more preferably $C_{1-4}$, most preferably $C_{1-3}$ hydrocarbon moiety, preferably an alkyl, alkenyl, or alkynyl moiety, wherein each carbon atom is optionally substituted by a halogen, an alkoxy, a haloalkoxy, a hydroxyl, or an oxo moiety.

X and Z are H (hydrogen) or form protecting groups. Compounds according to the invention wherein each of X and Z is H can be referred to as unprotected compounds according to the invention. These unprotected compounds benefit from a good solubility in water. They can enter cells through active uptake, such as receptor-mediated uptake, because the carbohydrate scaffold is recognized by various receptor proteins. Accordingly, in preferred embodiments, each instance of X is hydrogen, more preferably each instance of X and of Z is hydrogen. Conversely, when X is more lipophilic (for example when it comprises a longer aliphatic moiety), it can more readily pass through a cell membrane through passive diffusion (Yin et al., 2017, DOI 10.1002/bit.26291; Almaraz et al., 2012, DOI 10.1002/bit.24363). Accordingly, in preferred embodiments, each instance of X is independently chosen from the group consisting of a linear, branched, or cyclic $C_{1-6}$ acyl moiety, preferably a $C_{2-4}$ acyl moiety, wherein each carbon atom is optionally substituted by a halogen, an alkoxy, or a haloalkoxy moiety, and wherein the acyl chain is optionally unsaturated.

X is in each instance independently chosen from the group consisting of hydrogen and a linear, branched, or cyclic $C_{1-6}$ acyl moiety wherein each carbon atom is optionally substituted by a halogen, an alkoxy, or a haloalkoxy moiety, and wherein the acyl chain is optionally unsaturated. In preferred embodiments, X is in each instance independently chosen from the group consisting of hydrogen and a linear, branched, or cyclic $C_{2-4}$ acyl moiety wherein each carbon atom is optionally substituted by a halogen, an alkoxy, or a haloalkoxy moiety, and wherein the acyl chain is optionally unsaturated. Accordingly, X either forms a free hydroxyl moiety, or forms an ester. In preferred embodiments, X is acetyl, propionyl, or butyryl, most preferably acetyl. In highly preferred embodiments, each X is acetyl.

In preferred embodiments, each instance of X is the same. This simplifies their synthesis and purification, while their in vitro or in vivo behaviour is more predictable because the identical groups will behave more similarly. The anomeric position can often be addressed independently, and accordingly in preferred embodiments, each instance of X except the X at the anomeric position (C-2) is the same. In this case, preferably the X at the anomeric position is H. In highly preferred embodiments, X at the anomeric position is H, while each other X is acetyl.

In preferred embodiments, each X is independently selected from the moieties shown in table 1:

TABLE 1 preferred moieties for X

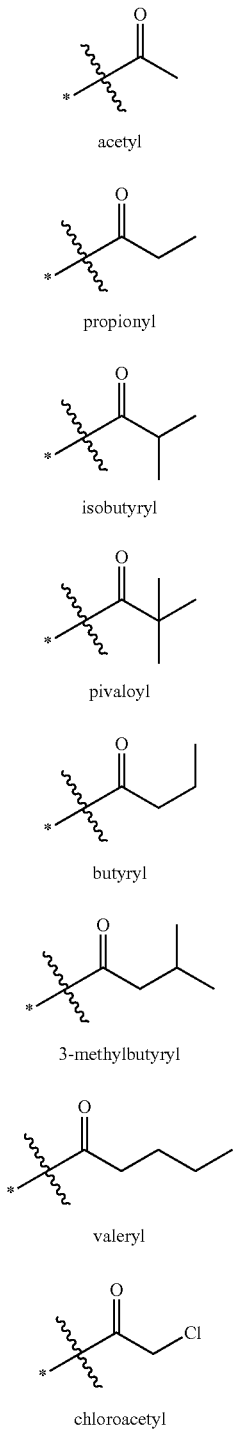

acetyl propionyl isobutyryl pivaloyl butyryl 3-methylbutyryl valeryl chloroacetyl TABLE 1-continued preferred moieties for X

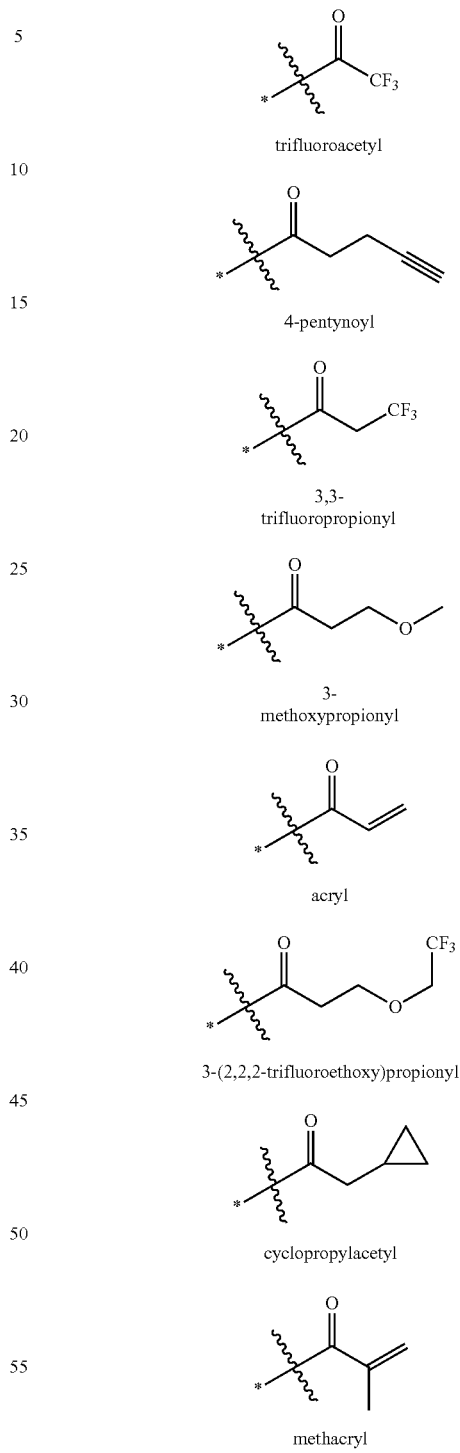

trifluoroacetyl 4-pentynoyl 3,3-trifluoropropionyl 3-methoxypropionyl acryl 3-(2,2,2-trifluoroethoxy)propionyl cyclopropylacetyl methacryl Z is chosen from the group consisting of hydrogen and a linear, branched, or cyclic $C_{1-6}$ alkyl, alkenyl, or alkynyl moiety wherein each carbon atom is optionally substituted by a halogen, an alkoxy, or a haloalkoxy moiety. Preferably, Z is chosen from the group consisting of hydrogen and a linear, branched, or cyclic $C_{1-4}$ alkyl, alkenyl, or alkynyl moiety wherein each carbon atom is optionally substituted by a halogen, an alkoxy, or a haloalkoxy moiety. Accordingly, Z either forms a free carboxylic acid or an ester.

In preferred embodiments, Z is selected from the moieties shown in table 2:

TABLE 2 preferred moieties for Z or R

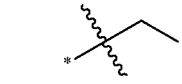

ethyl

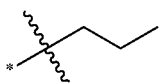

n-propyl

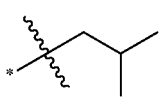

isobutyl

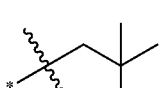

pivalyl

n-butyl

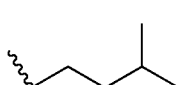

3-methylbutyl

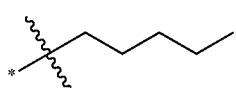

n-pentyl

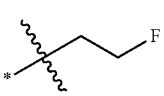

2-fluoroethyl

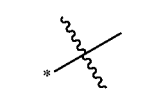

methyl

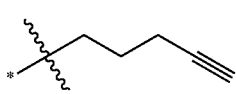

4-pentynyl

TABLE 2-continued preferred moieties for Z or R

propargyl

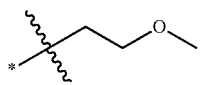

2-methoxyethyl

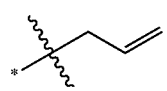

allyl

cyclobutyl

cyclopropyl

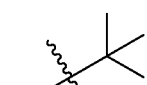

tert-butyl

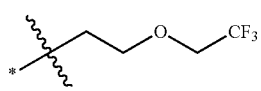

2-(2,2,2-trifluoroethoxy)ethyl

2,2,2-trichloroethyl

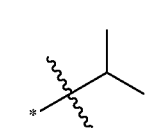

isopropyl

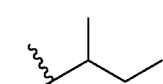

sec-butyl

In more preferred embodiments, Z is chosen from the group consisting of methyl, ethyl, n-propyl, isopropyl, cyclopropyl, allyl, propargyl, n-butyl, tert-butyl, sec-butyl, isobutyl, and cyclobutyl, more preferably Z is methyl.

R is a linear, branched, or cyclic $C_{1-6}$ hydrocarbon moiety, preferably an alkyl, alkenyl, or alkynyl moiety, wherein each carbon atom is optionally substituted by a halogen, an alkoxy, a haloalkoxy, a hydroxyl, or an oxo moiety, or optionally R is H when c' is S(=O), L is absent, and Q' is not absent. When R is cyclic it is optionally unsaturated, preferably forming phenyl. In other preferred embodiments, R is not phenyl. For preferred compounds according to the invention, R is not phenyl when c' is S(=O). Together with Q, Q', c', and L, R forms the potency element of the alfa-heteroatomic or beta-heteroatomic derivative of 3-fluorinated neuraminic acid. It was surprisingly found that smaller substituents lead to an increased potency. Accordingly, throughout this application, when an alkoxy moiety or a haloalkoxy moiety are referred to, this is preferably to be interpreted as a $C_{1-6}$ alkoxy or haloalkoxy moiety, more preferably as a $C_{1-4}$ alkoxy or haloalkoxy moiety, even more preferably as a $C_{1-2}$ alkoxy or haloalkoxy moiety, most preferably as a methoxy moiety.

Because R can carry an oxo substituent, R can be an acyl group as well as an alkyl group when the oxo substituent is on the carbon atom next to Q'. In these cases, R preferably is a linear, branched, or cyclic $C_{2-6}$ alkyl, alkenyl, or alkynyl moiety, wherein each carbon atom is optionally substituted by a halogen, an alkoxy, a haloalkoxy, a hydroxyl, or an oxo moiety.

In preferred embodiments, R is selected from the moieties shown in table 2 and phenyl, more preferably R is selected from the moieties shown in table 2.

R can be H when c' is S(=O), L is absent, and Q' is not absent. In these cases, it is preferred that Q' is O, so that a sulphonic acid amide-type moiety is formed. For preferred compounds of the invention R is a linear, branched, or cyclic $C_{1-6}$ hydrocarbon moiety, preferably an alkyl, alkenyl, or alkynyl moiety, wherein each carbon atom is optionally substituted by a halogen, an alkoxy, a haloalkoxy, a hydroxyl, or an oxo moiety.

Preferably, R is chosen from the group consisting of methyl, ethyl, isobutyl, tert-butyl, n-butyl, allyl, propargyl, acetyl, 2-methoxyethyl, 2,2,2-trichloroethyl, and 2-fluoroethyl, and optionally phenyl. More preferably, R is chosen from the group consisting of methyl, ethyl, isobutyl, tert-butyl, n-butyl, allyl, propargyl, acetyl, 2-methoxyethyl, 2,2,2-trichloroethyl, and 2-fluoroethyl, and optionally phenyl. Even more preferably, R is chosen from the group consisting of methyl, ethyl, isobutyl, tert-butyl, n-butyl, allyl, propargyl, 2-methoxyethyl, 2,2,2-trichloroethyl, and 2-fluoroethyl, and optionally phenyl. Most preferably, R is chosen from the group consisting of methyl, ethyl, isobutyl, tert-butyl, n-butyl, allyl, propargyl, 2-methoxyethyl, 2,2,2-trichloroethyl, and 2-fluoroethyl.

In preferred embodiments, this aspect provides the compound according to the invention, wherein: X is in each instance chosen from the group consisting of acetyl, propionyl, and butyryl, preferably X is acetyl; and/or Z is chosen from the group consisting of methyl, ethyl, n-propyl, isopropyl, cyclopropyl, allyl, propargyl, n-butyl, tert-butyl, sec-butyl, isobutyl, and cyclobutyl, preferably Z is methyl; and/or Q is chosen from the group consisting of O, S, and NH, preferably O and S, more preferably Q is O; and/or Q' is chosen from the group consisting of O, S, and NH, preferably O and NH, more preferably Q' is O; and/or L is —$CH^2$— or is absent, preferably L is absent; and/or R is a linear, branched, or cyclic $C_{1-6}$ hydrocarbon moiety, preferably an alkyl, alkenyl, or alkynyl moiety, wherein each carbon atom is optionally substituted by a halogen, an alkoxy (preferably a $C_{1-6}$ alkoxy), a haloalkoxy (preferably a $C_{1-6}$ haloalkoxy), a hydroxyl, or an oxo moiety, and/or optionally c' is S(=O) and Q' is absent and Q is O. In preferred embodiments, c' is C, or c' is S(=O) and Q' is absent and L is absent and Q is O.

In preferred embodiments, this aspect provides the compound according to the invention, wherein: X is in each instance chosen from the group consisting of acetyl, propionyl, and butyryl, preferably X is acetyl; and/or Z is chosen from the group consisting of methyl, ethyl, n-propyl, isopropyl, cyclopropyl, allyl, propargyl, n-butyl, tert-butyl, sec-butyl, isobutyl, and cyclobutyl, preferably Z is methyl; and/or Q is chosen from the group consisting of O, S, and NH, preferably O and S, more preferably Q is O; and/or Q' is chosen from the group consisting of O, S, and NH, preferably O and NH, more preferably Q' is O; and/or L is —$CH^2$— or is absent, preferably L is absent; and/or R is chosen from the group consisting of methyl, ethyl, isobutyl, tert-butyl, n-butyl, allyl, propargyl, acetyl, 2-methoxyethyl, 2,2,2-trichloroethyl, and 2-fluoroethyl, and/or optionally c' is S(=O) and Q' is absent and Q is O.

In preferred embodiments, this aspect provides the compound according to the invention, wherein: X is in each instance chosen from the group consisting of acetyl, propionyl, and butyryl, preferably X is acetyl; and Z is chosen from the group consisting of methyl, ethyl, n-propyl, isopropyl, cyclopropyl, allyl, propargyl, n-butyl, tert-butyl, sec-butyl, isobutyl, and cyclobutyl, preferably Z is methyl; and Q is chosen from the group consisting of O, S, and NH, preferably O and S, more preferably Q is O; and Q' is chosen from the group consisting of O, S, and NH, preferably O and NH, more preferably Q' is O; and L is —$CH^2$— or is absent, preferably L is absent; and R is chosen from the group consisting of methyl, ethyl, isobutyl, tert-butyl, n-butyl, allyl, propargyl, acetyl, 2-methoxyethyl, 2,2,2-trichloroethyl, and 2-fluoroethyl, and/or optionally c' is S(=O) and Q' is absent and Q is O.

In preferred embodiments, this aspect provides the compound according to the invention, wherein: X is in each instance chosen from the group consisting of acetyl, propionyl, and butyryl, preferably X is acetyl; and/or Z is chosen from the group consisting of methyl, ethyl, n-propyl, isopropyl, cyclopropyl, allyl, propargyl, n-butyl, tert-butyl, sec-butyl, isobutyl, and cyclobutyl, preferably Z is methyl; and/or Q is chosen from the group consisting of O and S, preferably Q is O; and/or Q' is chosen from the group consisting of O and NH; preferably Q' is O; and/or L is absent; and/or R is a linear, branched, or cyclic $C_{1-6}$ hydrocarbon moiety, preferably an alkyl, alkenyl, or alkynyl moiety, wherein each carbon atom is optionally substituted by a halogen, an alkoxy (preferably a $C_{1-6}$ alkoxy), a haloalkoxy (preferably a $C_{1-6}$ haloalkoxy), a hydroxyl, or an oxo moiety, and/or optionally c' is S(=O) and Q' is absent and Q is O.

In preferred embodiments, this aspect provides the compound according to the invention, wherein: X is in each instance chosen from the group consisting of acetyl, propionyl, and butyryl, preferably X is acetyl; and/or Z is chosen from the group consisting of methyl, ethyl, n-propyl, isopropyl, cyclopropyl, allyl, propargyl, n-butyl, tert-butyl, sec-butyl, isobutyl, and cyclobutyl, preferably Z is methyl; and/or Q is chosen from the group consisting of O and S, preferably Q is O; and/or Q' is chosen from the group consisting of O and NH; preferably Q' is O; and/or L is absent; and/or R is chosen from the group consisting of methyl, ethyl, isobutyl, tert-butyl, n-butyl, allyl, propargyl, acetyl, 2-methoxyethyl, 2,2,2-trichloroethyl, and 2-fluoroethyl, and/or optionally c' is S(=O) and Q' is absent and Q is O.

In preferred embodiments, this aspect provides the compound according to the invention, wherein: X is in each instance chosen from the group consisting of acetyl, propionyl, and butyryl, preferably X is acetyl; and Z is chosen from the group consisting of methyl, ethyl, n-propyl, and isopropyl, preferably Z is methyl; and Q is chosen from the group consisting of O and S, preferably Q is O; and Q' is chosen from the group consisting of O and NH; preferably Q' is O; and L is —CH²— or is absent; and R is chosen from the group consisting of methyl, ethyl, isobutyl, tert-butyl, n-butyl, allyl, propargyl, acetyl, 2-methoxyethyl, 2,2,2-trichloroethyl, and 2-fluoroethyl, and/or optionally c' is S(=O) and Q' is absent and Q is O.

In preferred embodiments, this aspect provides the compound according to the invention, wherein: X is chosen from the group consisting of acetyl, propionyl, and butyryl, preferably X is acetyl; and/or Z is chosen from the group consisting of methyl, ethyl, n-propyl, isopropyl, cyclopropyl, allyl, propargyl, n-butyl, tert-butyl, sec-butyl, isobutyl, and cyclobutyl, preferably Z is methyl or ethyl, more preferably methyl; and/or Q is chosen from the group consisting of O and S, preferably Q is O; and/or Q' is chosen from the group consisting of O and NH; preferably Q' is O; and/or L is absent; and/or R is chosen from the group consisting of methyl, ethyl, isobutyl, tert-butyl, n-butyl, allyl, propargyl, acetyl, 2-methoxyethyl, 2,2,2-trichloroethyl, and 2-fluoroethyl, and/or optionally c' is S(=O) and Q' is absent and Q is O.

In preferred embodiments, this aspect provides the compound according to the invention, wherein: X is chosen from the group consisting of acetyl, propionyl, and butyryl, preferably X is acetyl; and Z is chosen from the group consisting of methyl, ethyl, n-propyl, isopropyl, cyclopropyl, allyl, propargyl, n-butyl, tert-butyl, sec-butyl, isobutyl, and cyclobutyl, preferably Z is methyl or ethyl, more preferably methyl; and Q is chosen from the group consisting of O and S, preferably Q is O; and Q' is chosen from the group consisting of O and NH; preferably Q' is O; and L is absent; and R is chosen from the group consisting of methyl, ethyl, isobutyl, tert-butyl, n-butyl, allyl, propargyl, acetyl, 2-methoxyethyl, 2,2,2-trichloroethyl, and 2-fluoroethyl, and/or optionally c' is S(=O) and Q' is absent and Q is O.

In preferred embodiments, this aspect provides the compound according to the invention, wherein: X is in each instance chosen from the group consisting of acetyl, propionyl, and butyryl, preferably X is acetyl; and/or Z is chosen from the group consisting of methyl, ethyl, n-propyl, isopropyl, cyclopropyl, allyl, propargyl, n-butyl, tert-butyl, sec-butyl, isobutyl, and cyclobutyl, preferably Z is methyl; and/or Q is chosen from the group consisting of O and S, preferably Q is O; and/or Q' is chosen from the group consisting of O, S, and NH, or Q is absent when c' is S(=O); preferably Q' is O or is absent when c' is (S=0), most preferably Q' is O; and/or c' is C or when Q is O, c' is C or S(=O); and/or L is absent; and/or R is a linear, branched, or cyclic $C_{1-6}$ hydrocarbon moiety, preferably an alkyl, alkenyl, or alkynyl moiety, wherein each carbon atom is optionally substituted by a halogen, an alkoxy, a haloalkoxy, a hydroxyl, or an oxo moiety, preferably R is chosen from the group consisting of methyl, ethyl, isobutyl, tert-butyl, n-butyl, allyl, propargyl, acetyl, 2-methoxyethyl, 2,2,2-trichloroethyl, and 2-fluoroethyl.

In preferred embodiments, this aspect provides the compound according to the invention, wherein: X is in each instance chosen from the group consisting of acetyl, propionyl, and butyryl, preferably X is acetyl; and/or Z is chosen from the group consisting of methyl, ethyl, n-propyl, isopropyl, cyclopropyl, allyl, propargyl, n-butyl, tert-butyl, sec-butyl, isobutyl, and cyclobutyl, preferably Z is methyl; and/or Q is O; and/or Q' is absent; and/or c' is S(=O); and/or L is absent; and/or R is a linear, branched, or cyclic $C_{1-6}$ hydrocarbon moiety, preferably an alkyl, alkenyl, or alkynyl moiety, wherein each carbon atom is optionally substituted by a halogen, an alkoxy, a haloalkoxy, a hydroxyl, or an oxo moiety, preferably R is chosen from the group consisting of methyl, ethyl, isobutyl, tert-butyl, n-butyl, allyl, propargyl, acetyl, 2-methoxyethyl, 2,2,2-trichloroethyl, and 2-fluoroethyl.

In particular embodiments, the invention provides a combination of a compound according to the invention and an adjuvant, preferably an immune adjuvant. Adjuvants are described later herein.

Composition

In another aspect, the invention provides a composition comprising a compound according to the invention and a pharmaceutically acceptable excipient. Preferably, such a composition is formulated as a pharmaceutical composition. A preferred excipient is water, preferably purified water, more preferably ultrapure water. Further preferred excipients are adjuvants, binders, desiccants, or diluents. Further preferred compositions additionally comprise additional medicaments for treating cancer or for treating conditions associated with oversialylation, as later defined herein. Preferred additional medicaments in this regards are chemotherapeutic agents, immunotherapeutic agents, or steroids for the treatment of cancer, or antiviral agents, or antibacterial agents.

Preferably, a composition according to the invention further comprises a delivery vehicle. In said delivery vehicle, a compound according to the invention is contained in the delivery vehicle or is attached to the delivery vehicle. Accordingly, a compound according to the invention may be present in or attached to the delivery vehicle. A preferred delivery vehicle in a composition according to the present invention is a nanoparticle or an antibody or an antibody conjugate. In case the delivery vehicle is an antibody or an antibody conjugate, the compound according to the invention is attached to the delivery vehicle; the antibody is preferably an anti-tyrosinase related protein-1 antibody. A nanoparticle according to the present invention is preferably a poly(lactic-co-glycolic acid) (PLGA) based nanoparticle. Preferably, a nanoparticle according to the present invention comprises a targeting device. Such a targeting device may be any compound that is capable of targeting the delivery vehicle, in vitro, ex vivo or in vivo, to a predetermined target. The predetermined target may be a microbiological cell or a tumor cell, preferably a tumor cell, more preferably a melanoma cell. A preferred targeting device according to the present invention is an antibody which may be polyclonal but preferably is monoclonal. A preferred antibody is an anti-tyrosinase related protein-1 antibody to target the nanoparticle according to the invention to a melanoma cell. Further preferred delivery vehicles are liposomes, polymersomes, and protein cages.

Medical Use

As described above, inhibition of sialyltransferases can be beneficial for the treatment of various diseases and conditions. Due to their potency as sialyltransferase inhibitors, the invention provides in a second aspect a compound of general formula (I) wherein X is in each instance independently chosen from the group consisting of hydrogen and a linear, branched, or cyclic $C_{1-6}$ acyl moiety wherein each carbon atom is optionally substituted by a halogen, an alkoxy, or a haloalkoxy moiety, and wherein the acyl chain is optionally unsaturated;

Z is chosen from the group consisting of hydrogen and a linear, branched, or cyclic $C_{1-6}$ alkyl, alkenyl, or alkynyl moiety wherein each carbon atom is optionally substituted by a halogen, an alkoxy, or a haloalkoxy moiety;

Q and Q' are each independently chosen from the group consisting of O, S, and NH;

c' is C; or optionally when Q is O, c' is C or S(=O), and Q' can be absent when c' is S(=O);

L is either —$CH_2$— or is absent; and

R is a linear, branched, or cyclic $C_{1-6}$ hydrocarbon moiety, preferably an alkyl, alkenyl, or alkynyl moiety, wherein each carbon atom is optionally substituted by a halogen, an alkoxy, a haloalkoxy, a hydroxyl, or an oxo moiety, or optionally R is H when c' is S(=O), L is absent, and Q' is not absent;

for use as a medicament. These compounds are referred to hereinafter as compounds for use according to the invention. Definitions for X, Z, Q, Q', c', L, and R as defined for compounds according to the invention also apply to compounds for use according to the invention.

The invention similarly provides compositions according to the invention, or compositions comprising a compound for use according to the invention and a pharmaceutically acceptable excipient, for use as a medicament. These compositions are referred to hereinafter as compositions for use according to the invention.

In preferred embodiments, the medicament is for use in treating, preventing, or delaying bacterial infection, viral infection, cancer, a disorder of sialic acid metabolism, or an autoimmune disease. In more preferred embodiments, the medicament is for use in treating, preventing, or delaying bacterial infection, viral infection, an autoimmune disease, or cancer, more preferably bacterial infection, viral infection, or cancer. A compound for use according to the invention can conveniently be combined with state of the art cancer therapies such as, but not limited to cancer medicaments, radiation, surgical procedures, chemotherapy, immunotherapy, targeted therapies or a combination thereof. Similarly, it can be produced with the administration of antiviral or antibacterial agents.

In particular embodiments, the invention provides the use of a compound according to the invention or of a composition according to the invention for the manufacture of a medicament, preferably a medicament for the treatment, prevention, or delay of bacterial infection, viral infection, an autoimmune disease, metabolic sialylation disorders that result in oversialylation such as a congenital glycosylation disorder, or cancer, more preferably bacterial infection, viral infection, cancer, or optionally an autoimmune disease.

Formulation of medicaments, ways of administration, and the use of pharmaceutically acceptable excipients are known and customary in the art and for instance described in Remington; The Science and Practice of Pharmacy, 21st Edition 2005, University of Sciences in Philadelphia.

The medical use and methods according to this aspect of the present invention can be used to treat various subjects. A preferred subject is a subject in need of treatment, which can be a subject suffering from a disease or condition, or a subject expected to develop, or at risk of developing, a disease or condition. A preferred subject is a human or an animal subject. In preferred embodiments, a subject is not human.

In the context of this invention, a preferred cancer is neuroblastoma, glioma, leukaemia, lung cancer, bladder cancer, renal cancer, pancreatic cancer, adenocarcinoma, or epithelial cancer, and more preferably melanoma. Preferred examples of epithelial cancer are colorectal cancer, breast cancer, head and neck cancer, and prostate cancer. The treatment, prevention or delay of cancer is preferably the treatment, prevention or delay of cancer metastasis.

A preferred bacterial or viral infection is an infection with a sialic acid-binding pathogen such as a sialic acid-binding virus, examples of which are now in the art (Stencel-Baerenwald 2014, doi:10.1038/nrmicro3346). Preferred examples of sialic acid-binding viruses are influenza virus (Orthomyxoviridae), reovirus (Reoviridae), adenovirus (Adenoviridae), and rotavirus (Reoviridae).

A disorder of sialic acid metabolism is preferably a metabolic disorder leading to oversialylation, and can be a cancer or the result of a cancer. It can also be a congenital glycosylation disorders. A preferred disorder of sialic acid metabolism is a congenital glycosylation disorder or a sialic acid storage disease in which an aberrant amount of sialic acid is produced, such as an excessive amount, leading to its accumulation. Preferred disorder of sialic acid metabolism is a metabolic disorder associated with oversialylation or with excessive sialic acid storage. Examples of congenital glycosylation disorders, and preferred disorders of sialic acid metabolism, are infantile free sialic acid storage disease (ISSD), sialuria, French type sialuria, and salla disease. Such disorders are reviewed by Adams and Gahl (GeneReviews, 13 Jun. 2003, PMID: 20301643).

Oversialylation, also sometimes referred to as hypersialylation or aberrant sialylation, is a relative parameter, but a skilled person understands its meaning by context. It should be noted that when aberrant sialylation is referred to, it should not be considered as referring to hyposialylation in the context of this document. Oversialylation preferably refers to pathogenic sialylation, or to sialylation that hinders the function of the immune system. For example, when sialylation is on a pathogenic microbe such as a bacterium, and this sialylation hinders recognition of the microbe by the immune system, then any amount of sialylation can be considered to be oversialylation. When the sialylation is sialylation of a cell of the subject, then any sialylation that is in excess of sialylation of healthy tissue can be considered to be oversialylation. When the sialylation is sialyltion of an IgG, preferably of a self-reactive IgG, then any sialylation can be considered to be oversialylation, because anti-inflammatory activity is attributed to sialylation of the Fc glycan, so an IgG with less sialylation can lead to attenuated symptoms of an autoimmune disease (Pagan et al., 2018, doi: 10.1016/j.cell.2017.11.041). Accordingly, a preferred disease or condition associated with oversialylation is an autoimmune disease, more preferably it is rheumatoid arthritis or lupus such as systemic lupus erythematosus.

Medical use according to the invention can advantageously be combined with the use of an adjuvant. Alternately, the medical use of a composition according to the invention is the use of a composition that also comprises such an adjuvant. A preferred adjuvant is an immune adjuvant. Within the context of the present invention, an immune adjuvant may be any relevant compound that is able to initiate or enhance an immune response. Particularly preferred adjuvants are adjuvants that trigger Pattern Recognition Receptors such as Toll-Like Receptors TLR3, 7, 8 and/or TLR9, preferably TLR9, such as, but not limited to nucleic acid based immune adjuvants such as dsRNA, poly(I:C), Resiquimod (R-848), dendritic cell vaccines, ipilimumab (a monoclonal antibody against the cytotoxic T-lymphocyte antigen-4 (CTLA-4) immune checkpoint), blockade agents of programmed death 1 (PD-1) or at least one of its ligands PD-L1 and/or PD-L2, chimeric antigen-receptor carrying T cells, antibodies against for example CD27 or 4-1BB, preferably monoclonal antibodies against for example CD27 or 4-1BB, immunostimulants such as vaccines or antigens, and methylated or unmethylated CpG. Such adjuvants may be produced synthetically or may be produced from naturally occurring nucleic acids. Nucleic acid based immune adjuvants may comprise nucleic acid base analogues. A CpG in the context of the present invention is an oligonucleotide that comprises at least one CpG immunostimulatory motif, including pharmaceutically acceptable salts thereof; the person skilled knows relevant CpG's, e.g. from Bode et al., 2011, doi: 10.1586/erv.10.174. A CpG according to the present invention may comprise at least one internucleotide linkage that has a phosphate backbone modification such as a phosphorothioate or a phosphorodithioate modification and/or at least one stabilized internucleotide linkage. The use of phosphorothioate nucleotides enhances resistance to nuclease digestion when compared with native phosphodiester nucleotides, resulting in a substantially longer in vivo half life (30-60 min compared with 5-10 min for phosphodiester). In some embodiments, all internucleotide linkages have phosphate backbone modifications such as phosphorothioate or phosphorodithioate modifications. A CpG according to the present invention may comprise at least one nucleotide analogue providing enhanced immunostimulatory activity such as described in WO2008/068638 which is herein incorporated by reference. A preferred CpG according to the present invention is one selected from the ones described in Bode et al., 2011 and in EP2591787A1, such as but not limited to, class A CpG (also known as D-type CpG), class B CpG (also known as K-type CpG), class P CpG and class C CpG. A-class CpG oligodeoxyribonucleotides (ODN) typically include nuclease-resistant (stabilized) base sequences comprised of three or more consecutive guanines (poly-G motifs) at one or both ends, and a central region comprised of one or more CpG dinucleotides contained in a self-complementary palindrome. Members of A-class CpG ODN activate natural killer (NK) cells and induce interferon-alpha (INF-[alpha]) secretion from plasmacytoid dendritic cells (pDC). B-class CpG oligodeoxyribonucleotides typically include a stabilized non-palindromic nucleotide sequence, which comprises one or more CpG dinucleotides. In contrast to A-class ODN, B-class CpG oligodeoxyribonucleotides strongly activate B cells, but induce comparatively weaker INF-[alpha] secretion. C-class CpG oligodeoxyribonucleotides typically include one or more CpG motifs, which are located within the 5'-region, and a palindromic sequence, which is located at or near the 3'-end. They exhibit immunostimulatory activity that is characteristic of both A-class and B-class CpG ODN, including induction of INF-[alpha] secretion and activation of NK cells. At similar concentrations, C-class oligodeoxyribonucleotides generally exhibit B cell activation that is greater than what is observed with A-class CpG ODN, but is less than what is typically seen with B-class CpG ODN. Class P CpG contain two palindromic sequences, enabling them to form higher ordered structures. Class P CpG activate B cells and pDCs, and induce substantially greater IFN-α production when compared with class C CpG. A CpG according to the present invention may be optimized for a specific species such as mouse or human being; the person skilled in the art knows how to optimize a CpG for a specific species (see e.g. Bode et al., 2011).

In the medical use according to this aspect of the invention, administration may be performed through any suitable route including but not limited to: oral, aerosol or other device for delivery to the lungs, nasal spray, intravenous, intramuscular, subcutaneous, intradermal, intraperitoneal, intrathecal, vaginal, rectal, topical, lumbar puncture, intrathecal, intratumoral, peritumoral. A combination, a composition, compositions or a single composition according to the present invention may be administered to a subject or to a cell, tissue, tumor or organ of said subject for at least one week, one month, six month, one year or more. The frequency of administration of combination, a composition, compositions or a single composition according to the present invention may depend on several parameters such as the medical condition of the patient. The frequency may be ranged between at least once, two, three, four times a day, a week, or two weeks, or three weeks or four weeks or five weeks or a longer time period. The use may be combined with the use of an immune adjuvant, preferably at a dose that is ranged from 0.1 to 30 mg/kg body weight, preferably from 0.5 to 20 mg/kg, more preferably from 1 to 10 mg/kg, more preferably from 2 to 5 mg/kg of the immune adjuvant, more preferably 3 mg/kg. Preferred adjuvants are described above.

The dosage of the compound for use according to the invention is preferably ranged from 1 to 50 mg/kg body weight, preferably from 5 to 20 mg/kg, more preferably from 5 to 15 mg/kg, more preferably from 7 to 12 mg/kg of the immune adjuvant, more preferably 10 mg/kg.

Method of Treatment

In another aspect, the disclosure provides a method of treating, preventing, or delaying cancer, bacterial infection, a disorder of sialic acid metabolism, an autoimmune disease, or viral infection in a subject in need thereof, the method comprising the step of administering to the subject an effective amount of a compound according to the invention, or a compound for use according to the invention, or a composition according to the invention. An effective amount is preferably an amount that provides a beneficial effect. More features and definitions have been provided elsewhere herein.

Method for Reducing Sialylation

In another aspect, the invention provides a method for reducing sialylation, the method comprising the step of contacting a sialyltransferase with a compound according to the invention, with a compound for use according to the invention, or with a composition according to the invention. Such a method is referred to herein as a method according to the invention. In preferred embodiments of this aspect, the method is for inhibiting sialyltransferase. Accordingly, this aspect also provides a method for inhibiting sialyltransferase, the method comprising the step of contacting the sialyltransferase with a compound according to the invention, with a compound for use according to the invention, or with a composition according to the invention. This method can be an in vitro, in vivo, or ex vivo method. Preferably it is an in vitro method.

In preferred embodiments, the invention provides the method according to the invention, wherein the sialyltransferase is in a cell, wherein the method comprises the additional steps of:

i) contacting the cell with a compound according to the invention, with a compound for use according to the invention, or with a composition according to the invention; and ii) allowing the compound to passively diffuse into the cell, and/or to be actively taken up by the cell; preferably, allowing the compound to passively diffuse into the cell; wherein for the compound according to the invention or for the compound for use according to the invention preferably X is not hydrogen, and/or preferably Z is not hydrogen.

When both X and Z are hydrogen, preferably in step ii) the compound is allowed to be actively taken up by the cell, which is preferably a bacterial cell. When none of X and Z are hydrogen, or when only Z is hydrogen, preferably in step ii) the compound is allowed to passively diffuse into the cell. This method is preferably for reducing sialylation of the cell.

The cell in which sialylation is reduced, or in which the sialyltransferase is present, is preferably a cancer cell, a bacterial cell, or a cell at risk of being infected by a virus; more preferably it is a cancer cell or a bacterial cell. Reduction of sialylation can promote recognition of a bacterial cell or of a cancer cell by immune cells, or it can prevent infection of a host cell by a virus.

Reduction of sialylation can also advantageously be used to produce asialoglycoproteins. When terminal sialic acid residues are not incorporated in glycoproteins, the resulting proteins are known as asialoglycoproteins. The exposure of the subterminal galactose residues can result in rapid clearance of the asialoglycoglycoproteins from the circulation, for example through hepatocyte asialoglycoprotein receptors on Kuppfer cells. This can lead to attenuation of autoimmune disease (Pagan et al., 2018, doi: 10.1016/j.cell.2017.11.041). Accordingly, preferred methods of the invention are for the production of asialoglycoproteins.

Method for Producing Compounds According to the Invention

In a final aspect, the invention provides a method for the production of a compound according to the invention. Accordingly, this aspect provides a method of producing a sialic acid biosynthesis inhibitor, the method comprising the steps of:

i) providing a neuraminic acid derivative comprising an equatorial free amine at C-5 and comprising fluorine at C-3, preferably comprising axial fluorine at C-3;

ii) reacting the free amine at C-5 with a compound of general formula (IV):

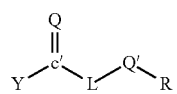

(IV)

wherein

Q and Q' are each independently chosen from the group consisting of O, S, and NH;

c' is C; or optionally when Q is O, c' is C or S(=O), and Q' can be absent when c' is S(=O);

L is either —$CH_2$— or is absent;

R is a linear, branched, or cyclic $C_{1-6}$ hydrocarbon moiety, preferably an alkyl, alkenyl, or alkynyl moiety, wherein each carbon atom is optionally substituted by a halogen, an alkoxy, a haloalkoxy, a hydroxyl, or an oxo moiety, or optionally R is H when c' is S(=O), L is absent, and Q' is not absent; and Y is a hydroxyl moiety, a halogen, or a condensed leaving group preferably selected from the group consisting of N-hydroxysuccinimide, sulfo-N-hydroxysuccinimide, 4-nitrophenol, pentafluorophenol, imidazole, 1-hydroxybenzotriazole, and —O-c'(=Q)-L-Q'-R, preferably —O—C(=Q)-L-Q'-R;

iii) optionally isolating the sialic acid biosynthesis inhibitor. Such a method is referred to hereinafter as a production method according to the invention. This production method allows for the efficient synthesis of compounds according to the invention and of compounds for use according to the invention. In the production method according to the invention, c' is preferably C, and Q' is preferably chosen from the group consisting of O, S, and NH.

In step i) a neuraminic acid derivative is provided. This derivative comprises an equatorial free amine at C-5 and comprises fluorine at C-3. The fluorine can be either axial or equatorial, but preferably it is axial. A skilled person can recognize such a neuraminic acid derivative, which may be protected or unprotected, and which can feature optional further substitutions, for example at the anomeric position. Preferred neuraminic acid derivatives for use in step i) are of general formula (V), preferably of general formula (V-ax), wherein X is in each instance independently chosen from the group consisting of hydrogen and a linear, branched, or cyclic $C_{1-6}$ acyl moiety wherein each carbon atom is optionally substituted by a halogen, an alkoxy, or a haloalkoxy moiety, and wherein the acyl chain is optionally unsaturated; preferably the $C_{1-6}$ acyl moiety is a $C_{2-4}$ acyl moiety; and wherein Z is chosen from the group consisting of hydrogen and a linear, branched, or cyclic $C_{1-6}$ alkyl, alkenyl, or alkynyl moiety wherein each carbon atom is optionally substituted by a halogen, an alkoxy, or a haloalkoxy moiety. More preferably, X is in each instance chosen from the group consisting of acetyl, propionyl, and butyryl, preferably X is acetyl; and/or Z is chosen from the group consisting of methyl, ethyl, n-propyl, isopropyl, cyclopropyl, allyl, propargyl, n-butyl, tert-butyl, sec-butyl, isobutyl, and cyclobutyl, preferably Z is methyl.

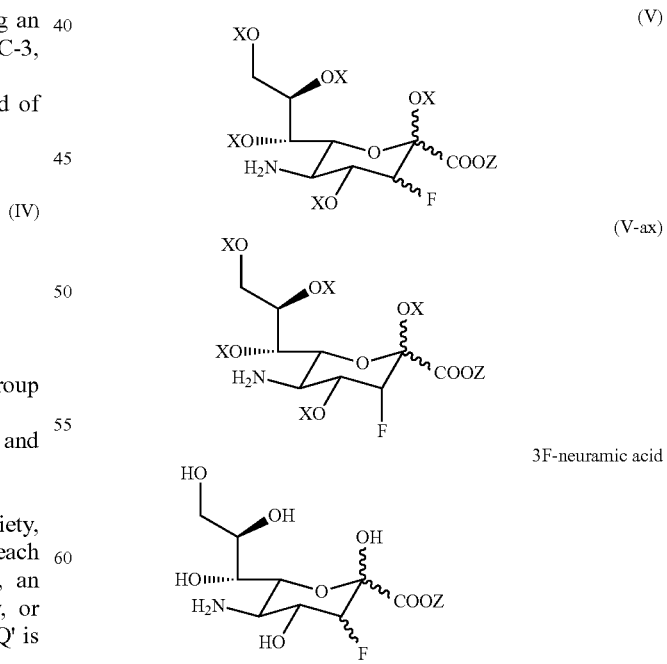

In step ii) the amine at C-5 of the neuraminic acid derivative that was provided in step i) is reacted with a compound of general formula (IV), wherein Q and Q' are each independently chosen from the group consisting of O, S, and NH; c' is C; or optionally when Q is O, c' is C or S(=O), and Q' can be absent when c' is S(=O); L is either —CH$_2$— or is absent; R is a linear, branched, or cyclic C$_{1-6}$ hydrocarbon moiety, preferably an alkyl, alkenyl, or alkynyl moiety, wherein each carbon atom is optionally substituted by a halogen, an alkoxy, a haloalkoxy, a hydroxyl, or an oxo moiety, or optionally R is H when c' is S(=O), L is absent, and Q' is not absent; and Y is a hydroxyl moiety, a halogen, or a condensed leaving group preferably selected from the group consisting of N-hydroxysuccinimide, sulfo-N-hydroxysuccinimide, 4-nitrophenol, pentafluorophenol, imidazole, 1-hydroxybenzotriazole, and —O-c'(=Q)-L-Q'-R.

Such compounds of general formula (IV) are acyl donors that introduce the R, Q, and Q' moieties to the compounds according to the invention or to the compounds for use according to the invention. A skilled person knows how to react these acyl donors with the amine at C-5 or the neuraminic acid derivative, and appreciates that the reactivity of this amine allows its selective reaction in the presence of possibly unprotected hydroxyl moieties that may also be present. The acyl donors can be carboxylic acids (Y is —OH, Q is O). In such a case, a coupling reagent such as a carbodiimide (such as dicyclohexylcarbodiimide, 1-ethyl-3-(3-dimethylaminopropyl)carbodiimide, or N,N-diisopropylcarbodiimide) or benzotriazol derivatives such as O-benzotriazol-1-yl-N,N,N',N'-tetramethyluronium hexafluorophosphate and optionally a base. When Y is a halogen or a condensed leaving group, a coupling reagent is generally not required. When Y is —O-c'(=Q)-L-Q'-R, the compound of general formula (IV) is an anhydride. In such a case, it is most preferably a symmetric anhydride. Suitable bases are mild bases such as DMAP or trialkylamine (triethylamine, diisopropylethylamine). A preferred base is trimethylamine. Preferred solvents are ethyl acetate, chloroform, dichloromethane, and DMF, most preferably dichloromethane. A preferred reaction duration is at least 2 hours, more preferably at least 6 hours, more preferably still overnight or at least 15 hours.

In preferred embodiments of the production method according to the invention, L is absent.

In preferred embodiments of the production method according to the invention, Y is a halogen, or a condensed leaving group preferably selected from the group consisting of N-hydroxysuccinimide, sulfo-N-hydroxysuccinimide, 4-nitrophenol, pentafluorophenol, imidazole, and 1-hydroxybenzotriazole; and/or L is absent.

In preferred embodiments of the production method according to the invention, Q is chosen from the group consisting of O and S, preferably Q is O; and/or Q' is chosen from the group consisting of O and NH; preferably Q' is O; and/or L is absent; and/or Y is a halogen, or a condensed leaving group preferably selected from the group consisting of N-hydroxysuccinimide, sulfo-N-hydroxysuccinimide, 4-nitrophenol, pentafluorophenol, imidazole, and 1-hydroxybenzotriazole.

In preferred embodiments of the production method according to the invention, Q is chosen from the group consisting of O and S, preferably Q is O; Q' is chosen from the group consisting of O and NH; preferably Q' is O; L is absent; Y is a halogen, or a condensed leaving group preferably selected from the group consisting of N-hydroxysuccinimide, sulfo-N-hydroxysuccinimide, 4-nitrophenol, pentafluorophenol, imidazole, and 1-hydroxybenzotriazole.

In preferred embodiments of the production method according to the invention, the compound of general formula IV is of general formula IV-c:

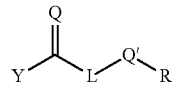

(IV-c)

wherein Q, L, R, and Y are as defined above, and wherein Q' is chosen from the group consisting of O, S, and NH, preferably wherein L is absent.

In preferred embodiments of the production method according to the invention, the compound of general formula IV is of general formula IV-s:

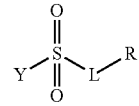

(IV-s)

wherein L, R, and Y are as defined above, preferably wherein L is absent, preferably wherein Y is a halogen such as chloride.

In step iii), which is optional, the produced sialic acid biosynthesis inhibitor is isolated. A skilled person knows how to isolate such compounds, and detailed procedures are provided in the examples. Preferably, the isolation comprises at least one step selected from the group consisting of washing (for example successively with 0.1M HCl and sat. NaHCO$_3$), drying (for example using MgSO$_4$) filtration, concentration in vacuo, and silicagel flash column chromatography (for example using 0%→50% EtOAc in Hept).

General Definitions

Throughout this application, the term "sialic acid biosynthesis inhibitor" is generally interchangeable with the term "sialyltransferase inhibitor". In preferred embodiments, compounds and compositions according to the invention are for use in methods according to the invention, or are for use according to the invention. Each embodiment as identified herein may be combined together unless otherwise indicated.

When a structural formula or chemical name is understood by the skilled person to have chiral centers, yet no chirality is indicated, for each chiral center individual reference is made to all three of either the racemic mixture (having any enantiomeric excess), the pure R enantiomer, and the pure S enantiomer. Whenever a fragment of a molecule, often referred to as a moiety, is represented, a dotted or wavy line indicates which bond links it to the entirety of the molecule; alternately, an asterisk (*) indicates where the represented moiety is linked to the rest of the molecule. This asterisk does not imply an atom, and neither does a bond that is crossed by a dotted or wavy line convey information about which atom is at the non-moiety side of the bond. All this is known in the art, and is routine practice.

Compounds and compounds for use provided in this invention can be optionally substituted. Suitable optional substitutions are replacement of —H by a halogen. Preferred halogens are F, Cl, Br, and I. Further suitable optional substitutions are substitution of one or more —H by —NH$_2$, —OH, =O, alkyl, alkoxy, haloalkyl, haloalkoxy, alkene, haloalkene, alkyne, haloalkyn, and cycloalkyl. Alkyl groups have the general formula $C_nH_{2n+1}$ and may alternately be linear or branched. Unsubstituted alkyl groups may also contain a cyclic moiety, and thus have the concomitant general formula $C_nH_{2n-1}$, and optionally cyclic $C_6$-alkyl can be aromatic, forming phenyl. Optionally, the alkyl groups are substituted by one or more substituents further specified in this document. Examples of alkyl groups include methyl, ethyl, propyl, 2-propyl, t-butyl, 1-hexyl, 1-dodecyl, etc. Throughout this application, the valency of atoms should always be fulfilled, and H can be added or removed as required.

Unless stated otherwise, —H may optionally be replaced by one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_5$-$C_{12}$ cycloalkenyl groups, $C_8$-$C_{12}$ cycloalkynyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens, amino groups, oxo and silyl groups, wherein the silyl groups can be represented by the formula $(R^2)_3Si$—, wherein $R^2$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more heteroatoms selected from the group consisting of O, N and S. Preferably, these optional substitutions comprise no more than twenty atoms, more preferably no more than fifteen atoms.

Whenever a parameter of a substance is discussed in the context of this invention, it is assumed that unless otherwise specified, the parameter is determined, measured, or manifested under physiological conditions. Physiological conditions are known to a person skilled in the art, and comprise aqueous solvent systems, atmospheric pressure, pH-values between 6 and 8, a temperature ranging from room temperature to about 37° C. (from about 20° C. to about 40° C.), and a suitable concentration of buffer salts or other components. It is understood that charge is often associated with equilibrium. A moiety that is said to carry or bear a charge is a moiety that will be found in a state where it bears or carries such a charge more often than that it does not bear or carry such a charge. As such, an atom that is indicated in this disclosure to be charged could be non-charged under specific conditions, and a neutral moiety could be charged under specific conditions, as is understood by a person skilled in the art.

In the context of this invention, a decrease or increase of a parameter to be assessed means a change of at least 5% of the value corresponding to that parameter. More preferably, a decrease or increase of the value means a change of at least 10%, even more preferably at least 20%, at least 30%, at least 40%, at least 50%, at least 70%, at least 90%, or 100%. In this latter case, it can be the case that there is no longer a detectable value associated with the parameter.

The use of a compound or composition as a medicament as described in this document can also be interpreted as the use of said compound or composition in the manufacture of a medicament. Similarly, whenever a compound or composition is used for as a medicament, it can also be used for the manufacture of a medicament, or in a method.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". The word "about" or "approximately" when used in association with a numerical value (e.g. about 10) preferably means that the value may be the given value (of 10) more or less 1% of the value. Variables of general structural formulas are sometimes presented in boldface to aid the reader, no technical meaning should be attributed to whether or not a variable such as R is shown in bold text or in regular text.

All patent and literature references cited in the present specification are hereby incorporated by reference in their entirety. As part of the disclosure R can also be a linear, branched, or cyclic $C_{1-7}$ hydrocarbon moiety, for example forming a benzyl moiety.

In the context of this invention, a cell or a sample can be a cell or a sample from a sample obtained from a subject. Such an obtained sample can be a sample that has been previously obtained from a subject. Such a sample can be obtained from a human subject. Such a sample can be obtained from a non-human subject.

SHORT DESCRIPTION OF DRAWINGS

FIG. 1: A) Working model of metabolic sialyltransferase inhibitors. The metabolic precursor is taken-up via passive diffusion and deacetylated by intracellular esterases. CMP activation in the nucleus by CMAS produces the active inhibitor Sia-3Fax-CMP which competitively blocks sialyltransferases and induces feedback inhibition of the de novo sialic acid synthesis pathway. B) Structure of the metabolic sialyltransferase inhibitors that were prepared containing various C-5 amide- or carbamate modifications.

Figure 2A:
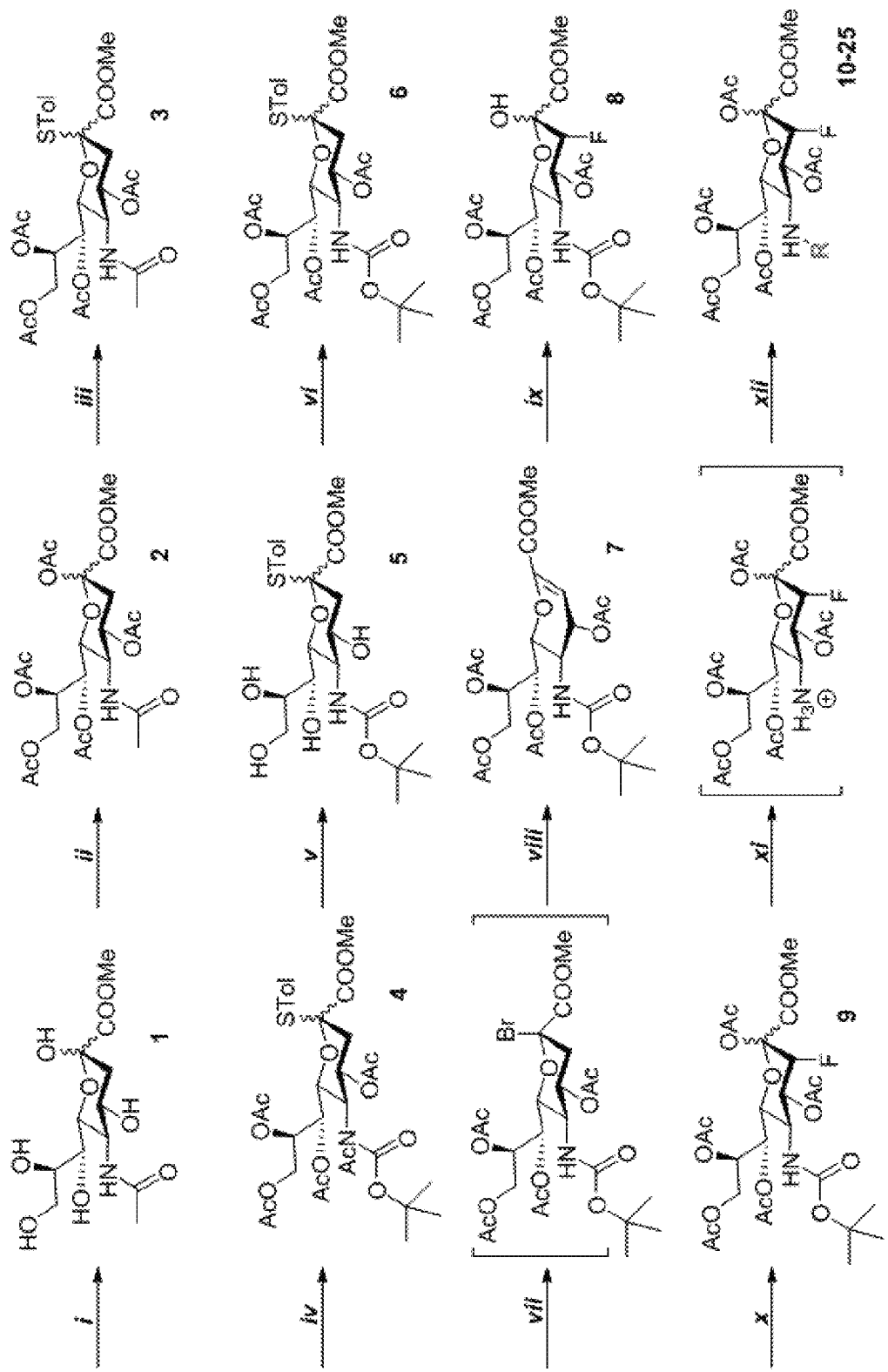

FIG. 2A: strategy for synthesis of various compounds according to the invention, or of reference compounds. i) Dowex H+, MeOH, r.t., 24 hrs ii) $Ac_2O$, Pyr, r.t., 24 hrs iii) HSTol, $BF_3.Et_2O$, r.t., 21 hrs, 95% (three steps), iv) $Boc_2O$, DMAP, THF, 70° C., 1 hr, 88% v) $K_2CO_3$, MeOH, r.t., 24 hrs, 83% vi) $Ac_2O$, Pyr, r.t., 7 hrs, 91% vii) $Br_2$, DCM, r.t., 2.5 hrs viii) TEA, DCM, r.t., 24 hrs, 78% (two steps) ix) Select-Fluor, $H_2O$, DMF, 60° C., 3 hrs, 72% (based on recovery of 7) x) $Ac_2O$, Pyr, r.t., 24 hrs, 95%, xi) TfOH or TFA, DCM, r.t., 5 min-4 hrs xii) R—Cl or R—OSu, DCM, TEA or Pyr, 16-24 hrs, 6-60%.

Figure 2B:
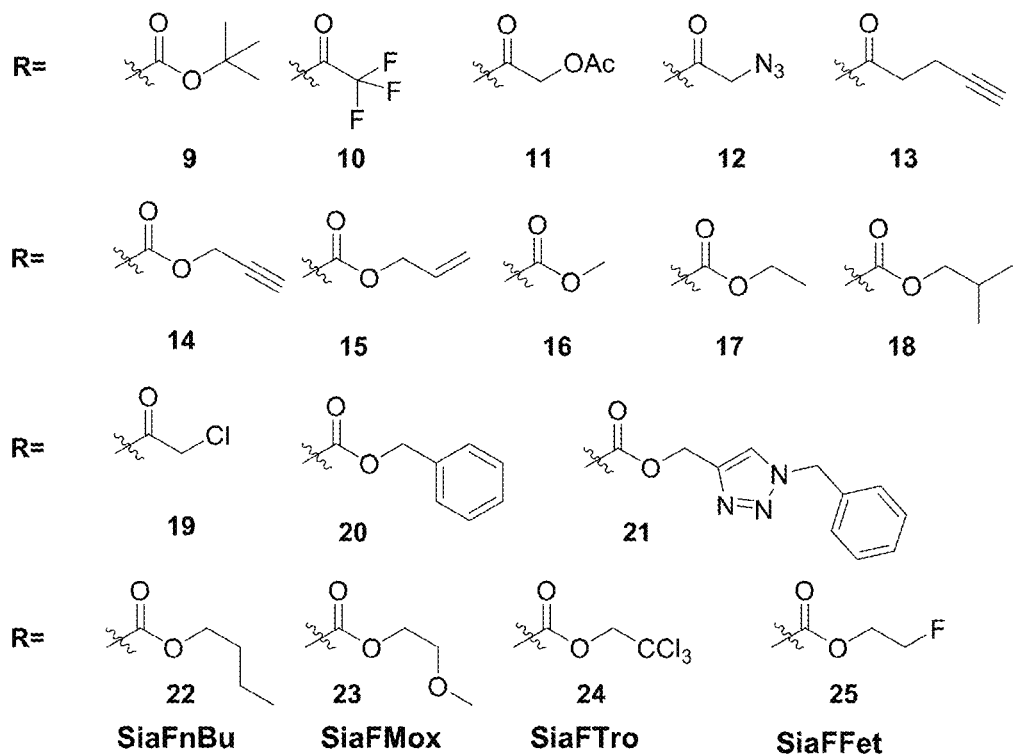

FIG. 2B: depictions of R groups.

Figure 3:
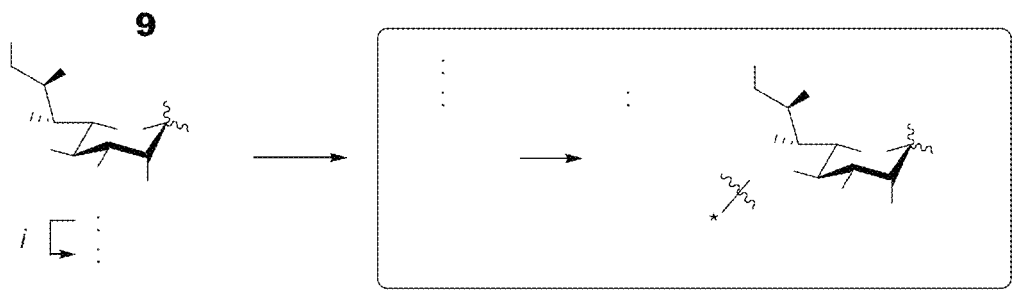

FIG. 3: synthesis of C-5 modified metabolic sialic acid biosynthesis inhibitors. Reagents and Conditions: i) $Ac_2O$, Pyridine, r.t., 48 hrs, 95%; ii) DCM, water, TFA, r.t., 2 hrs; iii) Activated acyl substituents (AAS), TEA, DCM, r.t.; 19: AAS=chloroacetyl chloride, overnight, 60%; 11: AAS=acetoxyacetyl chloride, overnight, 43%; 12: AAS=Azidoacetic acid NHS ester, 23 hrs, 16%; 13: AAS=4-Pentynoic acid NHS ester, overnight, 7%; 14: AAS=N-(propargyloxycarbonyloxy)-succinimide, 15 hrs, 40%; 15: AAS=Allyl chloroformate, 21.5 hrs, 16%; 16: AAS=methyl chloroformate, overnight, 33%; 17: AAS=ethyl chloroformate, overnight, 16%; 18: AAS=isobutyl chloroformate, overnight, 33%; 20: AAS=benzyl chloroformate, 21.5 hrs, 6%; iv) Benzyl azide, TBTA, CuI, Cu, DMF, water, t-butanol, r.t., overnight, 46%.

Figure 4:
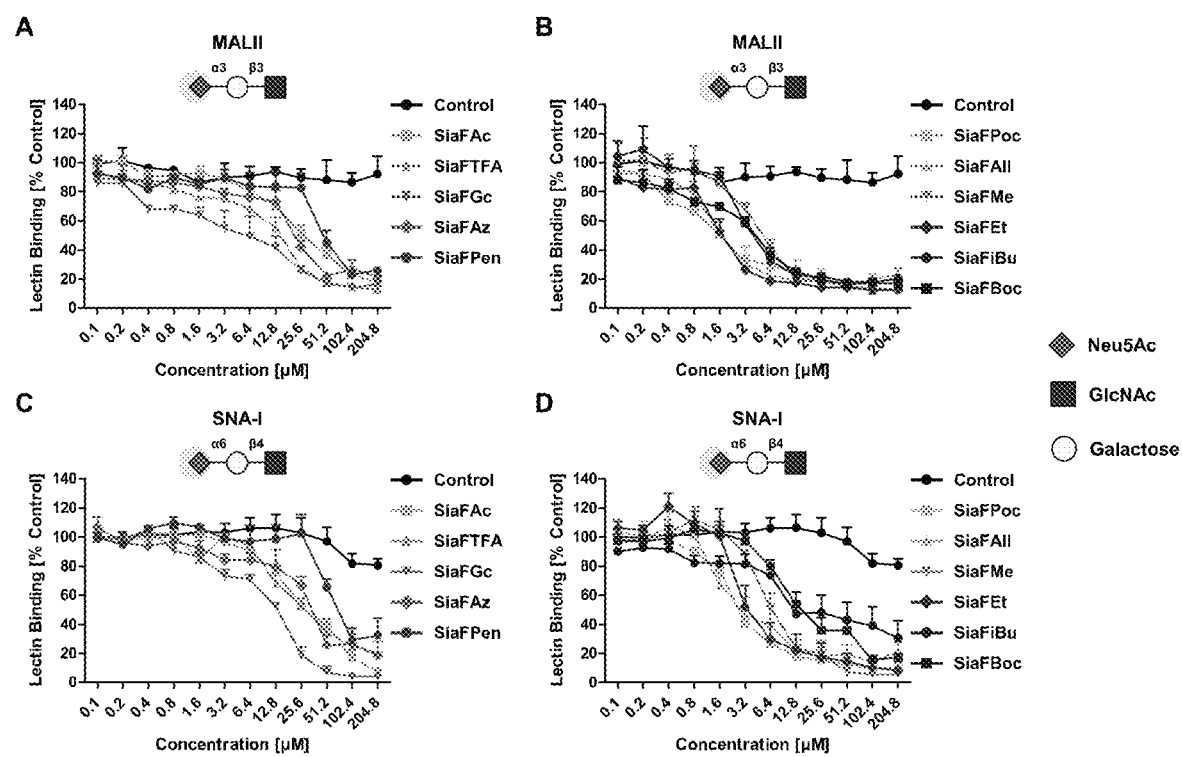

FIG. 4: Amide and carbamate fluorine sialic acids inhibit sialylation in B16-F10 cells. B16-F10 cells were treated for three days with 0.1-204.8 µM amide or carbamate fluorine sialic acids or DMSO control and stained with the biotinylated lectins MALII or SNA-1 that recognize α2,3-linked or α2,6-linked sialic acids, respectively and streptavidin-PE. Binding of the lectins was determined by flow cytometry and data of three independent experiments are presented as mean percentage lectin binding±SEM normalized to control cells. Graphs show MALII and SNA-1 binding to cells treated with amide fluorine sialic acids (A, C) and carbamate fluorine sialic acids (B, D) shown in FIG. 1B.

Figure 4E:
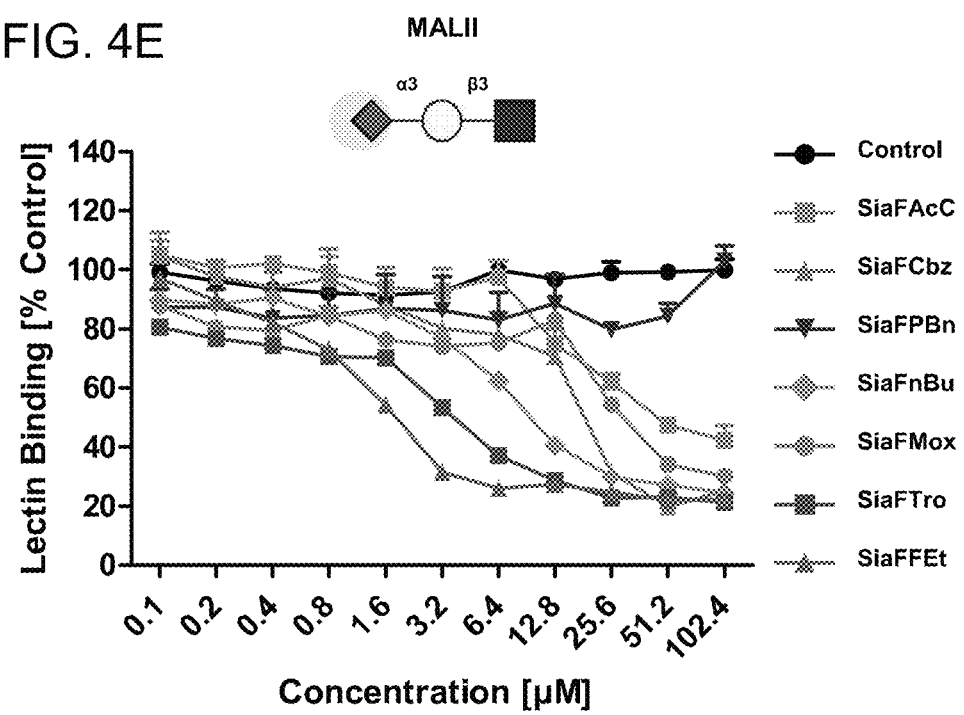

FIG. 4E: MALII data for additional fluorine sialic acids, shown in example 3.

Figure 4F:
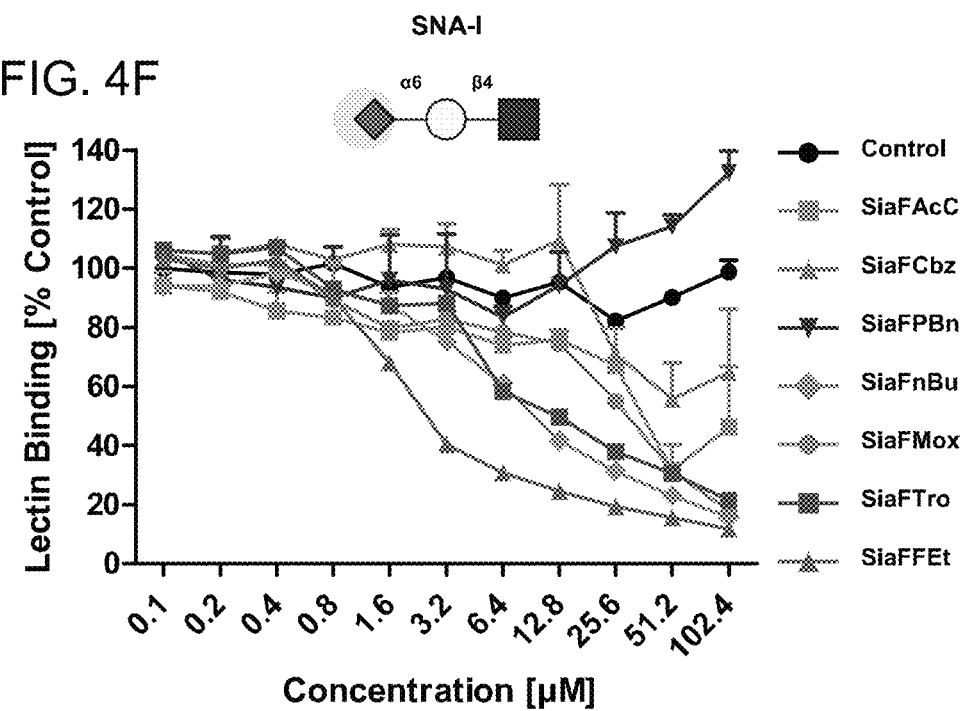

FIG. 4F: SNA-1 data for additional fluorine sialic acids, shown in example 3.

Figure 5:
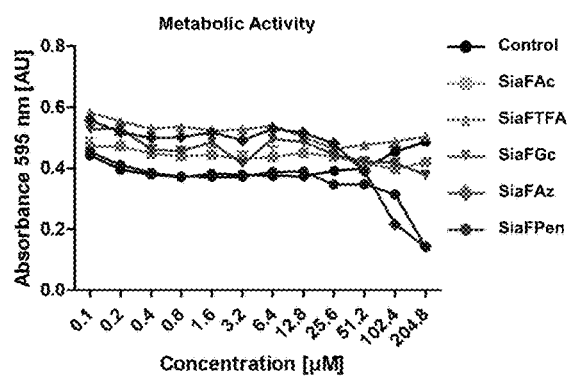
Figure 5:
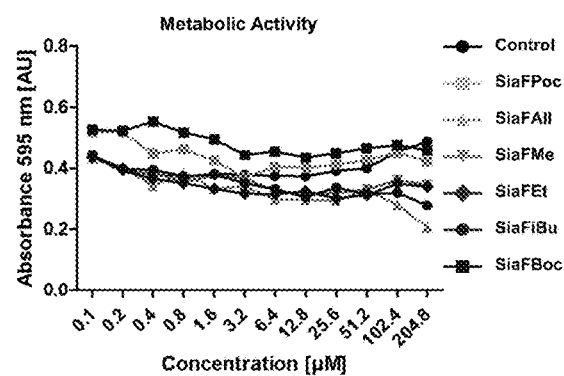

FIG. 5: Effect of fluorine sialic acids on cell metabolic activity/viability. B16-F10 cells were cultured for three days with increasing concentrations of fluorine sialic acids or DMSO and subjected to an MTT assay. Representative graphs show absorbance at 595 nm for cells treated with amide (A) or carbamate (B) fluorine sialic acids.

Figure 6:
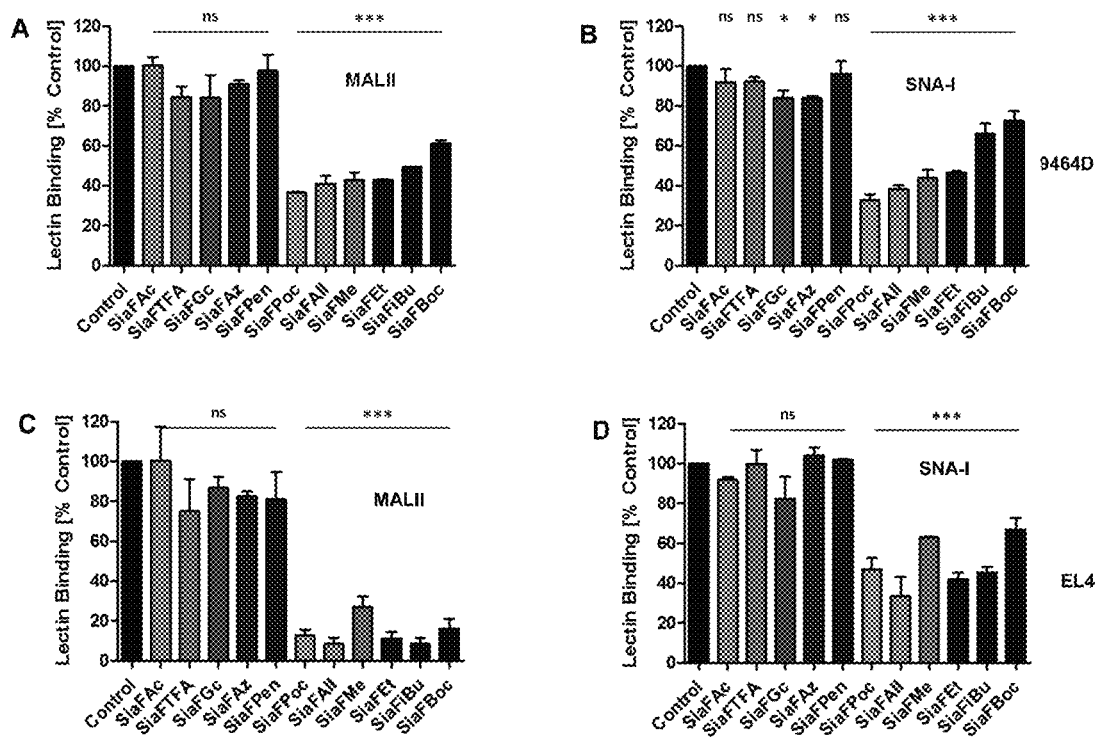

FIG. 6: Carbamate fluorine sialic acids inhibit sialylation in 9464D and EL4 cells. 9464D cells or EL4 cells were treated for three days with DMSO control or 102.4 µM amide or carbamate fluorine sialic acids. Cells were stained with MALII or SNA-1 lectin and streptavidin-PE and lectin binding was determined by flow cytometry. Bar diagrams show mean binding percentages±SEM of MALII and SNA-1 to 9464D cells (A, B) and EL4 cells (C, D) of three independent experiments.

Figure 7:
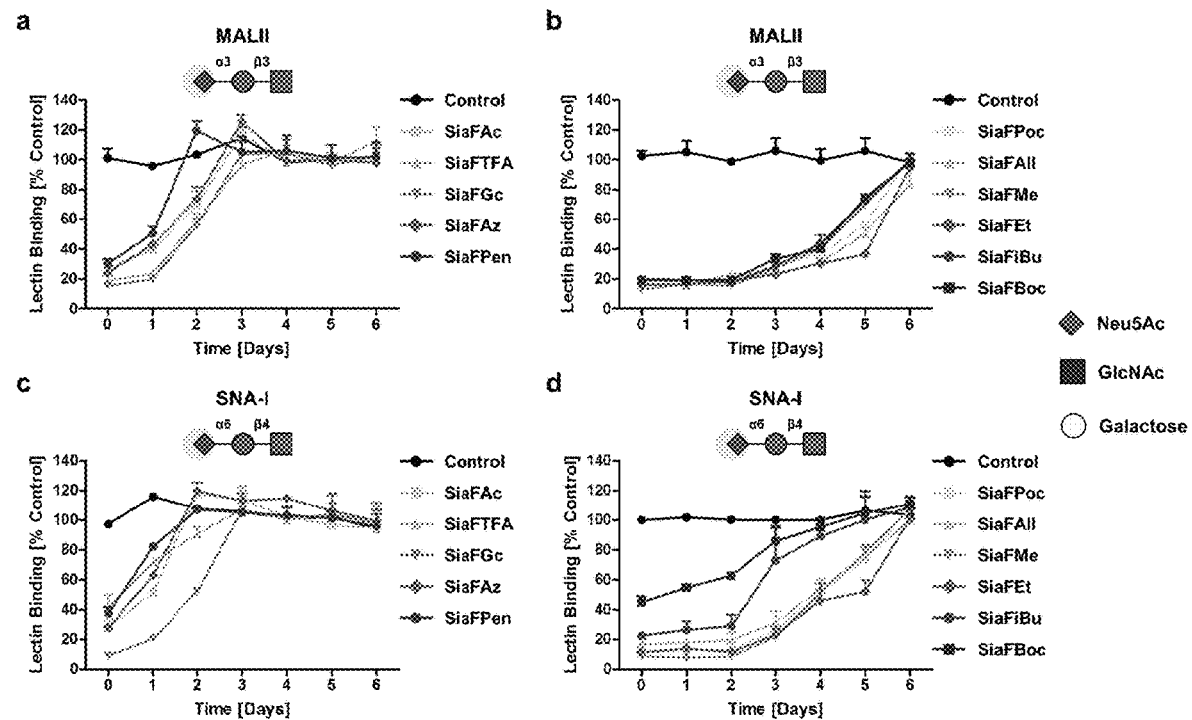

FIG. 7: Recovery of sialylation after amide or carbamate fluorine sialic acid treatment. B16-F10 cells were incubated for three days with 51.2 µM amide or carbamate fluorine sialic acids or DMSO control. Fluorine sialic acids were removed from the culture and the cells were reseeded. During a period of six days, sialylation was assessed daily with flow cytometry by MALII or SNA-1 lectins. Graphs show recovery of α2,3-sialylation (A, B) or α2,6-sialylation (C, D) in time presented as mean percentage lectin binding±SEM normalized to control (n=3).

Figure 8:
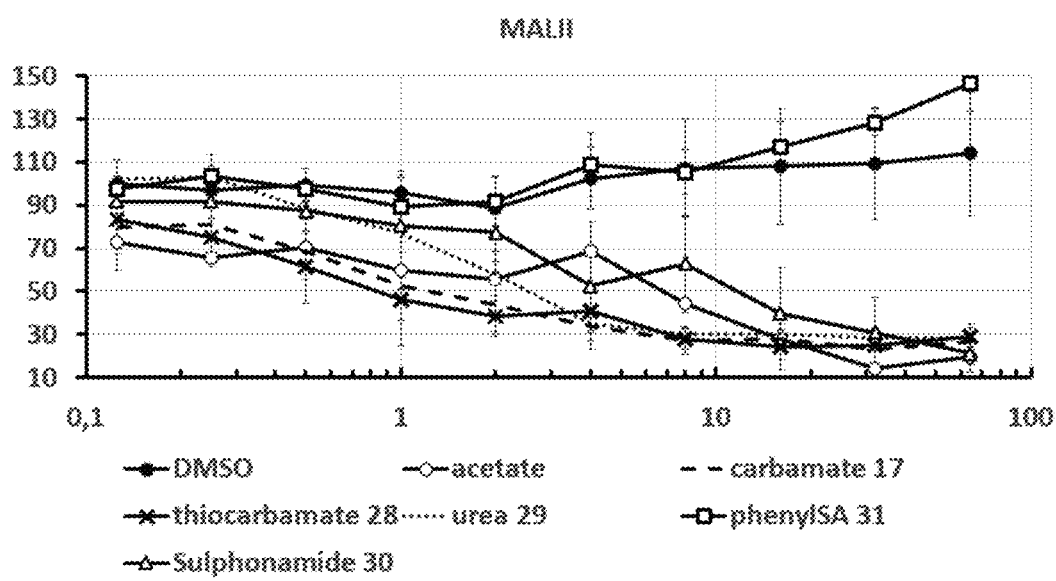
Figure 8:
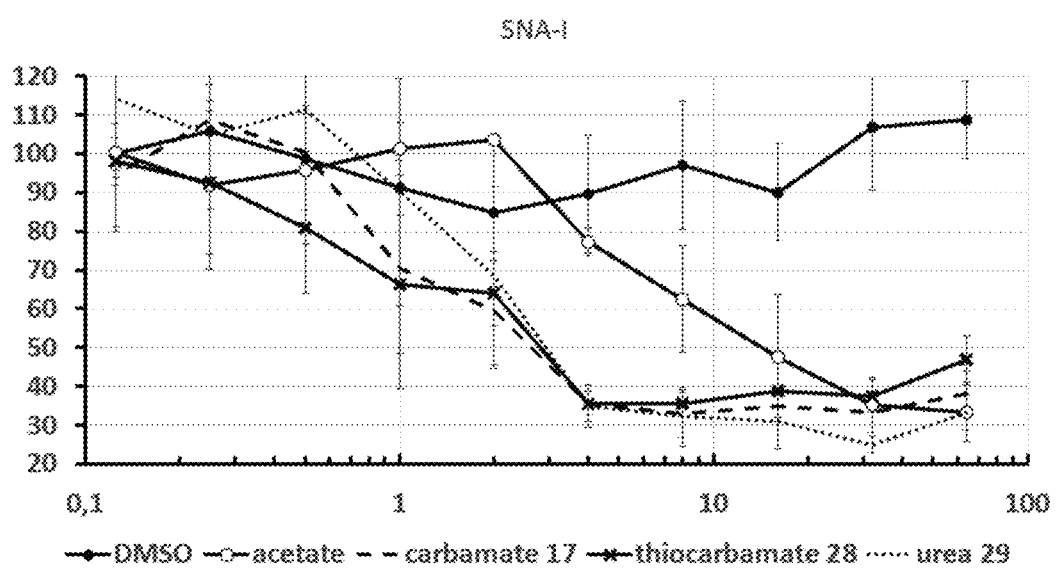

FIG. 8: urea, sulphonamide, and thiocarbamate fluorine sialic acids inhibit sialylation in B16-F10 cells. B16-F10 cells were treated for three days with 0.1-204.8 µM amide, carbamate, urea, or thiocarbamate fluorine sialic acids or DMSO control and stained with the biotinylated lectins MALII or SNA-1 that recognize α2,3-linked or α2,6-linked sialic acids, respectively and streptavidin-PE. Binding of the lectins was determined by flow cytometry and data of at least 4 independent experiments are presented as mean percentage lectin binding±SEM normalized to control cells. Graphs show MALII binding to cells (A) and SNA-1 binding to cells (B).

EXAMPLES

Example 1—Synthesis

General Synthetic Procedures $^1$H and $^{13}$C NMR spectra were recorded on a Varian Inova 400 MHz or Bruker Avance III 500 MHz spectrometer. Chemical shifts are reported in parts per million (ppm) relative to tetramethylsilane (TMS) as the internal standard. NMR data is presented as follows: Chemical shift, multiplicity (s=singlet, bs=broad singlet, d=doublet, t=triplet, dd=doublet of doublet, dt=doublet of triplet, m=multiplet and/or multiple resonances), integration, coupling constant in Hertz (Hz). All NMR signals were assigned on the basis of $^1$H, $^{13}$C, $^{19}$F NMR, COSY and HSQC experiments. Mass spectra were recorded on a JEOL JMS-T1000S AccuTOF mass spectrometer. Automatic column chromatography was performed on Biotage Isolera Spektra One, using SNAP cartridges 10-50 g filled with normal silica (Biotage, 30-100 µm, 60 Å) or water resistant iatro beads. Microwave reactions were performed on a Biotage Initiator 4.1.3. TLC analysis was conducted on TLC Silicagel, 60, F254, Merck, with detection by UV absorption (254 nm) where applicable, and by spraying with 20% $H_2SO_4$ in methanol followed by charring at ~150° C. or by spraying with a solution of $(NH_4)_6Mo_7O_{24}\cdot H_2O$ (25 g l$^{-1}$) in 10% $H_2SO_4$ in methanol followed by charring at ~300° C. DCM, ACN and Tol were freshly distilled. Reactions were carried out under an argon atmosphere.

Commonly Used Abbreviations

Ac$_2$O—Acetic anhydride; Acet—Acetone; ACN—Acetonitrile; AcOH—Acetic acid; Alloc—Allyloxycarbonyl; Az—Azidoacetic acid; BF$_3$.Et$_2$O—Boron trifluoride etherate; Boc$_2$O—Di-tert-butyl dicarbonate; Br$_2$—Bromine; Cbz—Carboxybenzyl; CD$_3$OD—Deuterated methanol; CDCl$_3$—Deuterated chloroform; ClAcCl—Chloroacetyl chloride; D$_2$O—Deuterium oxide; DCM—Dichloromethane; DMAP—Dimethylaminopyridine; DMF—N,N-Dimethylformamide; EtOAc—Ethyl acetate; EtOAc—Ethyl acetate; Hept—Heptane; iBu—Iso-butyl; Me—Methyl; n-Bu—Butyl; Poc—Propargylcarboxycarbonyl; Pyr—Pyridine; ROSu—Hydroxysuccinimide ester; SAda—Adamantyl-thiol; STol—4-methylthiophenol; TBTA—Tris(benzyltriazolyl methyl)amine; tBu—Tert-butyl; TEA—Triethylamine; TFA—Trifluoroacetic acid; TFAA—Trifluoroacetic acid anhydride; TfOH—Trifluoromethanesulfonic acid; TMSOTf—Trimethylsilyl trifluoromethanesulfonate; Tol—Toluene; Troc—2,2,2 trichloroethoxycarbonyl.

General Synthetic Strategy

FIG. 2 shows the strategy for synthesis of various compounds according to the invention, or of reference compounds. The P-3F$_{ax}$-NeuNAc derivatives were prepared from a common C-5 Boc protected precursor 9 (FIG. 3) to allow for rapid derivatization of the C-5 amine after Boc deprotection in a divergent manner. Thioglycoside 6 (Büll et al., 2015, DOI: 10.1021/acschembio.5b00501) was reacted with bromine to afford a mixture of the corresponding glycosyl bromide and glycal 7. Reaction of the mixture under basic conditions then afforded glycal 7 in a good overall yield (78%). Electrophilic fluorination using Selectfluor in a mixture of water/DMF afforded axial-fluorine 8 as the major product (Burkart et al., 1997, DOI: 10.1021/ja9723904). Finally, 8 was acetylated to afford 9 in high yield (95%).

Next, inhibitor precursor 9 was modified in a two-step sequence of Boc deprotection followed by acylation. Including precursor 9, inhibitor derivatives (11-21, FIG. 3) were prepared, carrying a variety of acyl groups in low to moderate yields (6-60%). Derivatives 12, 13 and 14 contain an alkyne or azide group which is amendable for modification using the copper catalyzed azide alkyne cycloaddition (CuAAC) reaction. To explore whether modifications introduced in this manner are tolerated by the sialic acid biosynthesis, derivative 21 was prepared using 14, benzylazide, and CuI/TBTA.

Intermediate: Methyl (5-acetamido-3,5-dideoxy-5-D-glycero-D-galacto)onate (1)

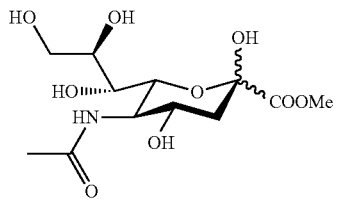

To a solution of N-acetylneuraminic acid (20 g; 64.7 mmol) in MeOH (600 ml; 0.1 M), Dowex (10 g) was added. After stirring at r.t. for 24 hrs, the mixture was filtered. The residue was washed with an excess of MeOH. The filtrate was concentrated in vacuo affording OH 1 (20.9 g; 64.7 mmol; quant.) TLC: (H$_2$O:ACN, 20:80 v/v) R$_f$=0.39. $^1$H NMR (500 MHz, CD$_3$OD) δ 4.07-3.98 (m, 2H, H-4; H-6), 3.85-3.79 (m, 2H, H-5; H-9$_a$), 3.78 (s, 3H, OMe), 3.70 (ddd, J=8.8, 5.7, 2.8 Hz, 1H, H-8), 3.62 (dd, J=11.3, 5.7 Hz, 1H, H-9$_b$), 3.48 (dd, J=9.2, 1.1 Hz, 1H, H-7), 2.22 (dd, J=12.9, 4.9 Hz, 1H, H-3$_{eq}$), 2.02 (s, 3H, Me, Ac), 1.89 (dd, J=12.8, 11.5 Hz, 1H, H-3$_{ax}$). $^{13}$C NMR (126 MHz, CD$_3$OD) δ 175.10 (C-1), 171.78 (CONH), 96.65 (C-2), 72.06 (C-6), 71.62 (C-8), 70.16 (C-7), 67.83 (C-4), 64.82 (C-9), 54.29 (C-5), 53.71 (OMe), 40.68 (C-3), 22.68 (Me, Ac). HR-ESI-TOF/MS (m/z): [M+Na]$^+$ calcd. for C$_{12}$H$_{21}$NNaO$_9$, 346.11140; found, 346.11286.

Intermediate: Methyl (5-acetamido-2,4,7,8,9-penta-O-acetyl-3,5-dideoxy-5-D-glycero-D-galacto)onate (2)

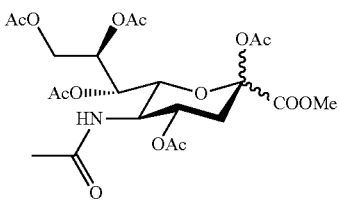

To a solution of 1 (20.9 g; 64.6 mmol) in Pyr (250 ml; 3.09 mol; 47.8 eq.), Ac$_2$O (125 ml; 1.59 mol; 24.6 eq.) was slowly added. After stirring at r.t. for 24 hrs, the mixture was concentrated in vacuo using Tol for co-evaporation. The residue was dissolved in EtOAc and washed successively with HCl (0.1 M) and sat. aq. NaHCO$_3$. The organic layer was dried over MgSO$_4$ and filtered. The filtrate was concentrated in vacuo affording 2 (34.5 g; 64.6 mmol; quant.) as a white foam. TLC: (Ace:DCM, 40:60 v/v) R$_f$=0.51. $^1$H NMR (500 MHz, CDCl$_3$, major anomer) δ 5.38-5.37 (m, 1H, H-7), 5.26 (ddt, J=10.1, 7.5, 4.9 Hz, 1H, H-4), 5.07 (ddd, J=6.8, 5.1, 2.5 Hz, 1H, H-8), 4.50 (dd, J=12.5, 2.6 Hz, 1H, H-9$_a$), 4.15-4.10 (m, 3H, H-9$_b$; H-6; H-5), 3.80 (s, 3H, OMe), 2.55 (dd, J=13.5, 5.0 Hz, 1H, H-3$_{eq}$), 2.15 (s, 3H, Me, OAc), 2.14 (s, 3H, Me, OAc), 2.10-2.09 (m, 1H, H-3$_{ax}$), 2.07 (s, 3H, Me, OAc), 2.05-2.03 (m, 6H, 2×Me, OAc), 1.90 (s, 3H, Me, NHAc). $^{13}$C NMR (126 MHz, CDC$_3$, major anomer) δ 171.15 (CO), 170.75 (CO), 170.41 (2×CO), 170.38 (CO), 168.37 (CO), 166.46 (CO), 97.65 (C-2), 73.00 (C6), 71.52 (C-8), 68.44 (C-4), 67.98 (C-7), 62.27 (C-9), 53.35 (OMe), 49.49 (C-5), 36.05 (C-3), 23.33 (Me, Ac), 21.05 (Me, Ac), 20.99 (Me, Ac), 20.93 (2×Me, Ac) 20.91 (Me, Ac). HR-ESI-TOF/MS (m/z): [M+Na]$^+$ calcd. for C$_{22}$H$_{31}$NNaO$_{14}$, 556.16422; found, 556.16487.

Intermediate: Methyl 5-acetamido-4,7,8,9-penta-O-acetyl-2,3,5-dideoxy-2-para-methylthiophenol-D-glycero-β-galacto-non-2-ulopyranosonate (3)

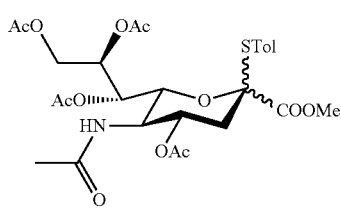

Similar to the previously described procedure (Chao et al., 2008, DOI: 10.1016/j.carres.2008.01.014), 2 (33.87 g; 63.5 mmol) was dissolved in DCM (400 ml; 0.16 M). HSTol (9.26 ml; 76 mmol; 1.2 eq.) was added to form a slightly yellow solution. BF$_3$.Et$_2$O (15.7 ml; 127 mmol; 2 eq.) was added and the reaction stirred for 21 hrs, washed with 10% Na$_2$S$_2$O$_3$ aq. and sat. NaHCO$_3$ aq. The organic layer was dried over MgSO$_4$, filtered and concentrated in vacuo. The residue was crystallized using DCM and Hept. The crystals were filtered, washed with Hept and collected with Ace. Evaporation of solvents in vacuo afforded 3 (35.92 g; 60.1 mmol; 95%) as a white foam. TLC: (Acet/DCM, 30/70): R$_f$=0.4; $^1$H NMR (500 MHz, CDCl$_3$, major anomer) δ 7.30 (dd, J=8.1, 1.8 Hz, 2H, 2×CH, meta STol), 7.12 (d, J=7.2 Hz, 2H, 2×CH, ortho STol), 5.68 (d, J=10.3 Hz, 1H, NH), 5.46 (t, J=2.4 Hz, 1H, H-7), 5.37 (td, J=11.1, 4.8 Hz, 1H, H-4), 4.95 (d, J=8.5 Hz, 1H, H-8), 4.61 (dd, J=10.5, 2.5 Hz, 1H, H-6), 4.49 (dd, J=12.3, 2.2 Hz, 1H, H-9$_a$), 4.12 (q, J=10.4 Hz, 1H, H-5), 4.02 (dd, J=12.2, 8.6 Hz, 1H, H-9$_b$), 3.58 (s, 3H, OMe), 2.64 (dd, J=13.8, 4.7 Hz, 1H, H-3$_{eq}$), 2.31 (s, 3H, Me, STol), 2.11-2.08 (m, 4H, H-3$_{ax}$; Me, Ac), 2.07 (s, 3H, Me, Ac), 2.03 (s, 3H, Me, Ac), 1.95 (s, 3H, Me, Ac). $^{13}$C NMR (126 MHz, CDCl$_3$, major anomer) δ 171.13 (CO, Ac), 170.90 (CO, Ac), 170.23 (CO, Ac), 170.19 (CO, Ac), 170.16 (CO, Ac), 168.21 (C-1), 140.08 (CCH$_3$, STol), 136.14 (2×CH, meta STol), 129.80 (2×CH, ortho STol), 125.17 (C-5, STol), 88.82 (C-2), 73.10 (C-6), 73.01 (C-8), 69.05 (C-4), 68.78 (C-7), 62.64 (C-9), 52.51 (OMe), 49.36 (C-5), 37.33 (C-3), 23.10 (Me, Ac), 21.25 (Me, STol), 21.04 (Me, Ac), 20.83 (Me, Ac), 20.68 (Me, Ac), 20.64 (Me, Ac). HR-ESI-TOF/MS (m/z): [M+Na]$^+$ calcd. for C$_{27}$H$_{35}$NNaO$_{12}$S, 620.17776; found, 620.17694.

Intermediate: Methyl 5-[(tert-butoxycarbonyl)amino]-4,7,8,9-penta-O-acetyl-2,3,5-dideoxy-2-para-methylthiophenol-D-glycero-β-galacto-non-2-ulopyranosonate (4)

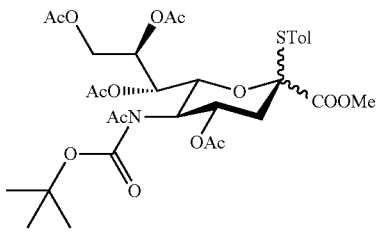

4

Similar to the previously described procedure (Büll et al., 2015, DOI: 10.1021/acschembio.5b00501), 3 (30.93 g; 51.7 mmol) was dissolved in THF (500 ml; 0.1 M). Successively, Boc$_2$O (24.0 ml; 103 mmol; 2 eq.) and 4-dimethylaminopyridine (3.16 g; 25.9 mmol; 0.5 eq.) were added. After stirring at 70° C. for 2 hrs, the 4 mixture was concentrated in vacuo. The residue was dissolved in EtOAc and washed with sat. aq. NaHCO$_3$. The organic layer was dried over MgSO$_4$, filtered and concentrated in vacuo. Silicagel flash column chromatography (0%→10% Ace in DCM) afforded 4 (31.66 g; 45.4 mmol; 88%) as a slightly yellow foam. TLC: (Acet:DCM, 5:95 v/v) R$_f$=0.47 $^1$H NMR (500 MHz, CDCl$_3$, major anomer) δ 7.34 (d, J=8.2 Hz, 2H, 2×CH, meta STol), 7.14 (d, J=8.0 Hz, 3H, 2×CH, ortho STol), 5.80 (td, J=11.0, 4.9 Hz, 1H, H-4), 5.44 (dd, J=10.1, 2.1 Hz, 1H, H-6), 5.35 (t, J=2.5 Hz, 1H, H-7), 5.12 (dt, J=8.2, 2.6 Hz, 1H, H-8), 4.85 (t, J=10.5 Hz, 1H, H-5), 4.49 (dd, J=12.4, 2.3 Hz, 1H, H-9$_b$), 4.06 (dd, J=12.4, 8.2 Hz, 1H, H-9$_a$), 3.58 (s, 3H, OMe), 2.74 (dd, J=13.8, 4.9 Hz, 1H, H-3$_{eq}$), 2.36 (s, 3H, Me, NAc), 2.34 (s, 3H, Me, STol), 2.13 (dd, J=13.8, 11.1 Hz, 1H, H-3$_{ax}$), 2.07 (s, 3H, Me, OAc), 2.06 (s, 3H, Me, OAc), 1.97 (s, 3H, Me, OAc), 1.97 (s, 3H, Me, OAc), 1.72 (s, 9H, tBu, Boc). $^{13}$C NMR (126 MHz, CDCl$_3$, major anomer) δ 173.93 (CO, Ac), 170.64 (CO, Ac), 170.50 (CO, Ac), 170.33 (CO, Ac), 169.94 (CO, Ac), 168.28 (C-1), 152.10 (CO, Boc), 140.21 (CCH$_3$, STol), 136.40 (2×CH meta STol), 129.95 (2×CH ortho STol), 125.76 (C-5, STol), 89.50 (C-2), 85.42 (C(CH$_3$)$_3$, Boc), 72.91, (C-8), 72.29 (C-6), 68.68 (C-7), 66.54 (C-4), 62.53 (C-9), 52.98 (C-5), 52.57 (OMe), 38.88 (C-3), 28.29 (tBu, Boc), 26.73 (Me, NHAc), 21.44 (Me, STol), 21.13 (Me, OAc), 20.93 (Me, OAc), 20.81 (2×Me, OAc). HR-ESI-TOF/MS (m/z): [M+Na]$^+$ calcd. for C$_{32}$H$_{43}$NNaO$_{14}$S, 720.23019; found, 720.23055.

Intermediate: Methyl 5-(tert-butoxycarbamado)-2,3,5-dideoxy-2-para-methylthiophenol-D-glycero-β-galacto-non-2-ulopyranosonate (5)

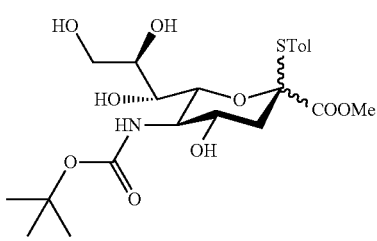

5

As described previously (Büll et al., 2015, DOI: 10.1021/acschembio.5b00501), 4 (31.65 g; 45.4 mmol) was dissolved in MeOH (200 ml; 0.23 M) and K$_2$CO$_3$ (3.13 g; 22.7 mmol; 0.5 eq.) was added. After stirring at r.t. for 24 hrs the reaction was quenched with AcOH to pH 6 and filtered. The filtrate was concentrated in vacuo. Silicagel flash column chromatography (0%→10% MeOH in DCM) afforded 5 (18.39 g; 37.7 mmol; 83%). TLC: (MeOH:DCM, 10:90 v/v) R$_f$=0.56 $^1$H NMR (500 MHz, CDCl$_3$, major anomer) δ 7.35 (d, J=8.1 Hz, 2H, 2×CH, meta STol), 7.11 (d, J=8.0 Hz, 2H, 2×CH, ortho STol), 5.27 (d, J=8.7 Hz, 1H, NH), 4.30 (d, J=10.4 Hz, 1H, H-6), 4.08 (td, J=10.9, 4.6 Hz, 1H, H-5), 3.80-3.65 (m, 5H, H-9$_a$; H-9$_b$; H-8; H-7; H-5), 3.57 (s, 3H, OMe), 2.71 (dd, J=13.8, 4.7 Hz, 1H, H-3$_{eq}$), 2.32 (s, 3H, Me, STol), 2.05-1.99 (m, 1H, H-3$_{ax}$), 1.45 (s, 9H, tBu, Boc). $^{13}$C NMR (126 MHz, CDCl$_3$, major anomer) δ 169.49 (C-1), 157.82 (CO, Boc), 139.98 (C-Me STol), 135.73 (2×CH, meta STol), 129.87 (2×CH, ortho STol), 126.24 (C-5 STol), 89.59 (C-2), 81.13 (C(CH$_3$)$_3$, Boc) 72.85 (C-6), 70.56 (C-7), 70.23 (C-8), 68.20 (C-4), 64.55 (C-9), 54.12 (C-5), 52.78 (OMe), 40.67 (C-3), 28.47 (tBu, Boc), 21.39 (Me, STol). HR-ESI-TOF/MS (m/z): [M+Na]$^+$ calcd. for C$_{22}$H$_{33}$NNaO$_9$S, 510.17737; found, 510.17732.

Intermediate: Methyl 5-(tert-butoxycarbamado)-4,7,8,9-penta-O-acetyl-2,3,5-dideoxy-2-para-methylthiophenol-D-glycero-β-galacto-non-2-ulopyranosonate (6)

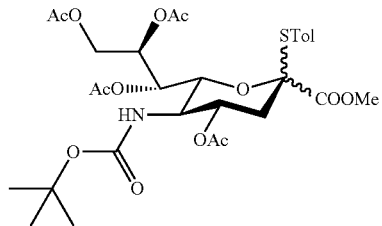

6

As described previously (Büll et al., 2015, DOI: 10.1021/acschembio.5b00501), 5 (8.39 g; 17.2 mmol) was dissolved in Pyr (62 ml; 764 mmol; 44.4 eq.). Ac$_2$O (36 ml; 382 mmol; 22.2 eq.) was slowly added. After stirring at r.t. for 7 hrs, the mixture was concentrated in vacuo using Tol for co-evaporation. The residue was dissolved in EtOAc and washed successively with HCl (0.1 M) and sat. aq. NaHCO$_3$. The organic layer was dried over MgSO$_4$ and filtered and concentrated in vacuo. Silicagel flash column chromatography (0%→50% EtOAc in Hept) afforded 6 (10.26 g; 15.6 mmol; 91%) as a white foam. TLC: (EtOAc:Hept, 50:50 v/v) R$_f$=0.47 $^1$H NMR (500 MHz, CDCl$_3$) δ 7.32 (d, J=7.7 Hz, 2H, 2×CH, meta STol), 7.14 (d, J=7.7 Hz, 2H, 2×CH, ortho STol), 5.55 (t, J=2.6 Hz, 1H, H-7), 5.33 (td, J=11.1, 4.8 Hz, 1H, H-4), 5.01 (dt, J=8.5, 2.5 Hz, 1H, H-8), 4.55 (dd, J=10.5, 2.6 Hz, 1H, H-6), 4.51 (dd, J=12.2, 2.3 Hz, 1H, H-9$_a$), 4.45 (d, J=10.7 Hz, 1H, NH), 4.04 (dd, J=12.2, 8.5 Hz, 1H, H-9$_b$), 3.79 (q, J=10.6 Hz, 1H, H-5), 3.61 (s, 3H, OMe), 2.67 (dd, J=13.8, 4.8 Hz, 1H, H-3$_{eq}$), 2.34 (s, 3H, Me, STol), 2.10 (s, 3H, Me, OAc), 2.08 (s, 3H, Me, OAc), 2.04 (s, 4H, H-3$_{ax}$; Me, OAc), 1.97 (s, 3H, Me, OAc), 1.40 (s, 9H, tBu, Boc). $^{13}$C NMR (126 MHz, CDCl$_3$) δ 170.98 (CO, OAc), 170.61 (CO, OAc), 170.43 (CO, OAc), 169.93 (CO, OAc), 168.48 (C-1), 155.35 (CO, Boc), 140.22 (C-Me, STol) 136.38 (2×CH, meta STol), 129.99 (2×CH ortho STol), 125.41 (C-5, STol), 88.87 (C-2), 80.29 (C(CH$_3$)$_3$, Boc), 73.34 (C-6), 72.90 (C-8), 69.51 (C-4), 69.12 (C-7), 62.92 (C-9), 52.68 (OMe), 50.96 (C-5), 37.59 (C-3), 28.28 (tBu, Boc), 21.44 (Me, STol), 21.21 (Me, OAc), 20.94 (Me, OAc), 20.83 (Me, OAc), 20.82 (Me, OAc). HR-ESI-TOF/MS (m/z): [M+Na]$^+$ calcd. for C$_{30}$H$_{41}$NNaO$_{13}$S, 678.21963; found, 678.21799.

Intermediate: Methyl 5-(tert-butoxycarbamado]-4,7,8,9-tetra-O-acetyl-2,6-anhydro-3,5-dideoxy-D-glycero-D-galacto-non-2-enonate (7)

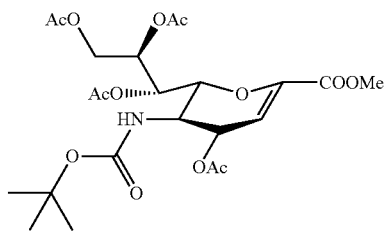

To a solution of 6 (2.757 g; 4.22 mmol) in DCM (42.2 ml; 0.1 M), slowly Br$_2$ (0.239 ml; 4.64 mmol; 1.1 eq.) was added. After 2.5 hrs stirring at r.t., the reaction was diluted with DCM and washed with 10% Na$_2$S$_2$O$_3$. The milky organic layer was dried over MgSO$_4$, filtered and the clear filtrate was extracted once more with 10% Na$_2$S$_2$O$_3$ aq. before drying over MgSO$_4$, filtering. The filtrate was concentrated in vacuo, redissolved in DCM (42.0 ml; 0.1 M) and TEA (1.699 g; 16.79 mmol; 4 eq.) was added. The reaction was stirred overnight at r.t. and concentrated in vacuo. The residue was dissolved in EtOAc and washed successively with HCl (0.1 M) and sat. aq. NaHCO$_{O3}$. The organic layer was dried over MgSO$_4$, filtered and again concentrated in vacuo. Silicagel flash column chromatography (0%→45% EtOAc in Hept) afforded 7 (1.734 g; 3.26 mmol; 78% two steps) as a white solid. TLC: (EtOAc:Hept, 60:40 v/v) R$_f$=0.62 $^1$H NMR (500 MHz, CDCl$_3$) δ 5.99 (d, J=3.1 Hz, 1H, H-3), 5.55 (t, J=4.3 Hz, 1H, H-7), 5.47 (dd, J=7.5, 3.1 Hz, 1H, H-4), 5.37 (ddd, J=6.8, 4.9, 3.4 Hz, 1H, H-8), 4.65 (d, J=9.9 Hz, 1H, NH), 4.60 (dd, J=12.3, 3.4 Hz, 1H, H-9$_a$), 4.33 (dd, J=9.0, 3.8 Hz, 1H, H-6), 4.19 (dd, J=12.2, 6.8 Hz, 1H, H-9$_b$), 4.09 (q, J=8.9 Hz, 1H, H-5), 3.80 (s, 3H, OMe), 2.13 (s, 3H, Me, OAc), 2.08 (s, 3H, Me, OAc), 2.06 (s, 3H, Me, OAc), 1.41 (s, 9H, tBu, Boc). $^{13}$C NMR (126 MHz, CDCl$_3$) δ 170.73 (CO, Ac), 170.68 (CO, Ac), 170.05 (CO, Ac), 169.91 (CO, Ac), 161.78 (C-1), 154.98 (CO, Boc), 145.15 (C-2), 108.11 (C-3), 80.57 (C(CH$_3$)$_3$, Boc), 76.94 (C-6), 70.58 (C-8), 68.60 (C-4), 67.92 (C-7), 62.10 (C-9), 52.66 (OMe), 48.01 (C-5), 28.27 (tBu, Boc), 20.96 (Me, OAc), 20.91 (Me, OAc), 20.85 (Me, OAc), 20.80 (Me, OAc). HR-ESI-TOF/MS (m/z): [M+Na]$^+$ calcd. for C$_{23}$H$_{33}$NNaO$_{13}$, 554.18496; found, 554.18611.

Methyl 5-(tert-butoxycarbamado)-4,7,8,9-penta-O-acetyl-3,5-dideoxy-3-fluoro-D-glycero-β-galacto-non-2-ulopyranosonate (8)

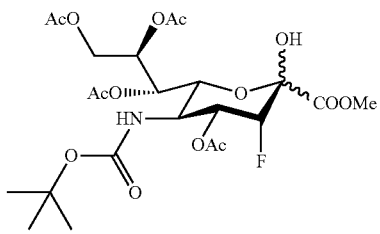

To a solution of 7 (1.724 g; 3.24 mmol) in a 1:3 mixture of H$_2$O and DMF (32 ml; 0.1 M), Selectfluor (3.45 g; 9.73 mmol; 3 eq.) was added. The reaction was stirred at 60° C. for 3 hrs. The mixture was quenched with sat. aq. NaHCO$_3$ and concentrated in vacuo—even though conversion was incomplete. The residue was dissolved in EtOAc and washed successively with HCl (0.1M) and sat. aq. NaHCO$_3$. The organic layer was dried over MgSO$_4$, filtered and concentrated in vacuo. Silicagel flash column chromatography (0%→50% EtOAc in Hept) afforded 8 (789 mg; 1.39 mmol; 72% based on recovery of starting material) as a white foam. TLC: (EtOAc:Hept, 60:40 v/v) R$_f$=0.47 $^1$H NMR (500 MHz, CDCl$_3$) δ 5.52 (s, 1H, OH), 5.47 (dd, J=4.4, 2.3 Hz, 1H, H-7), 5.37-5.23 (m, 2H, H-8; H$_4$), 4.94 (d, J=10.3 Hz, 1H, NH), 4.92 (dd, J=49.8, 2.1 Hz, 1H, H-3), 4.81 (dd, J=12.3, 2.5 Hz, 1H, H-9$_a$), 4.26 (dd, J=10.6, 2.3 Hz, 1H, H-6), 4.18-4.08 (m, 2H, H-5; H-9$_b$), 3.85 (s, 3H, OMe), 2.16 (s, 3H, Me, OAc), 2.09 (s, 3H, Me, OAc), 2.09 (s, 3H, Me, OAc), 2.04 (s, 3H, Me, OAc), 1.40 (s, 9H, tBu, Boc). $^{13}$C NMR (126 MHz, CDCl$_3$) δ 171.68 (CO, Ac), 171.48 (CO, Ac), 170.60 (CO, Ac), 170.19 (CO, Ac), 167.70 (C-1), 155.22 (CO, Boc), 94.45 (d, J=25.5 Hz, C-2), 87.06 (d, J=185.1 Hz, C-3), 80.09 (C(CH$_3$)$_3$, Boc), 71.91 (C-8), 71.46 (C-6), 69.96 (d, J=17.3 Hz, C-4), 68.63 (C-7), 63.01 (C-9), 53.50 (OMe), 46.36 (C-5), 28.31 (tBu, Boc), 21.13 (Me, OAc), 20.99 (Me, OAc), 20.85 (Me, OAc), 20.78 (Me, OAc). HR-ESI-TOF/MS (m/z): [M+Na]$^+$ calcd. for C$_{23}$H$_{34}$FNNaO$_{14}$, 590.18610; found, 590.18498.

Methyl 5-(tert-butoxycarbamado)-2,4,7,8,9-penta-O-acetyl-3,5-dideoxy-3-fluoro-D-glycero-β-galacto-non-2-ulopyranosonate (9)

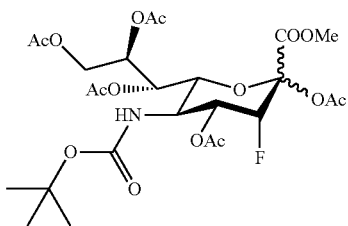

To a solution of 8 (789 mg; 1.39 mmol) in Pyr (12 ml; 148 mmol; 107 eq.), Ac$_2$O (6 ml; 63.6 mmol; 45.7 eq.) was slowly added. After stirring at r.t. for 24 hrs, the mixture was concentrated in vacuo using Tol for co-evaporation. The residue was dissolved in EtOAc and washed successively with HCl (0.1M) and sat. aq. NaHCO$_3$. The organic layer was dried over MgSO$_4$, filtered and concentrated in vacuo. Silicagel flash column chromatography (0%→50% EtOAc in Hept) afforded 9 (717 mg; 1.176 mmol; 95%) as a white foam. TLC: (EtOAc:Hept, 50:50 v/v) R$_f$=0.42 $^1$H NMR (500 MHz, CDCl$_3$) δ 5.46-5.34 (m, 2H, H-7; H-4), 5.18-5.11 (m, 1H, H-8), 4.92 (dd, J=49.1, 2.5 Hz, 1H, H-3), 4.60-4.54 (m, 1H, H-9$_a$), 4.48 (d, J=9.5 Hz, 1H, NH), 4.19 (dd, J=12.4, 6.6 Hz, 1H, H9$_b$), 4.12-3.97 (m, 2H, H-6; H-5), 3.84 (s, 3H, OMe), 2.17 (s, 3H, Me, OAc), 2.16 (s, 3H, Me, OAc), 2.12 (s, 3H, Me, OAc), 2.05 (s, 3H, Me, OAc), 2.04 (s, 3H, Me, OAc), 1.40 (s, 9H, tBu, Boc). $^{13}$C NMR (126 MHz, CDCl$_3$) δ 170.73 (CO, Ac), 170.48 (CO, Ac), 170.36 (CO, Ac), 170.25 (CO, Ac), 167.24 (CO, Ac), 165.28 (C-1), 154.88 (CO, Boc), 95.33 (d, J=29.0 Hz, C-2), 87.21 (d, J=185.1 Hz, C-3), 80.51 (C(CH$_3$)$_3$, Boc), 72.67 (C-6), 71.39 (C-8), 68.97 (d, J=17.2 Hz, C-4), 68.09 (C-7), 62.32 (C-9), 53.60 (OMe), 46.32 (C5), 28.27 (tBu, Boc), 21.00 (Me, OAc), 20.90 (Me, OAc), 20.86 (Me, OAc), 20.82 (Me, OAc), 20.74 (Me, OAc). HR-ESI-TOF/MS (m/z): [M+Na]$^+$ calcd. for C$_{25}$H$_{36}$FNNaO$_{15}$, 632.19667; found, 632.19540.

Reference Compound: Methyl 5-(trifluoroacetamido)-2,4,7,8,9-penta-O-acetyl-3,5-dideoxy-3-fluoro-D-glycero-β-galacto-non-2-ulopyranosonate (10)

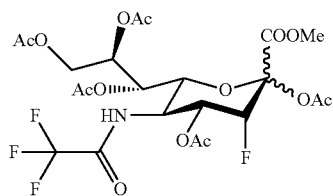

TFA protected Sialic acid 10 was a common side product after TFA deprotection. Further investigation discovered that TFA, if not removed carefully, forms a mixed anhydride with chloroformates resulting in a sometimes quantitative coupling of TFA to the relatively unreactive amine. Later deprotection reactions were therefore done with TfOH which avoids this problem. Boc inhibitor 9 (50 mg; 82 µmol) was dissolved in a 1:2 mixture of TFA and DCM (1.6 ml; 0.05 M). The mixture was stirred for 2 hrs at r.t. (TLC: (EtOAc:Hept, 60:40 v/v) R$_f$=0.09). The mixture was then concentrated in vacuo. The residue was dissolved in DCM (0.83 ml; 0.1 M) and additional TFA (188 µl, 2.5 mmol, 30 eq) and TEA (690 µl; 4.95 mmol; 60 eq.) were added. Isobutyl chloroformate (also possible with other chloroformates) (76 µl; 589 µmol; 20 eq.) was added and the reaction was stirred for 16 hrs. The mixture was diluted with DCM and washed successively with 0.1M HCl and sat. NaHCO$_3$. The organic layer was dried over MgSO$_4$, filtered and concentrated in vacuo. Silicagel flash column chromatography (0%→50% EtOAc in Hept) afforded 10 (44 mg; 74 µmol; 90%) as a white solid. TLC: (EtOAc:Hept, 60:40 v/v) R$_f$=0.50 $^1$H NMR (500 MHz, CDCl$_3$) δ 7.02 (d, J=9.1 Hz, 1H, NH), 5.61 (ddd, J=27.4, 11.0, 2.5 Hz, 1H, H-4), 5.29 (dd, J=5.3, 2.0 Hz, 1H, H-7), 5.13 (ddd, J=6.1, 5.2, 2.4 Hz, 1H, H-8), 4.97 (dd, J=48.9, 2.5 Hz, 1H, H-3), 4.57 (dd, J=12.5, 2.5 Hz, 1H, H-9$_a$), 4.38 (ddd, J=10.7, 2.0, 0.8 Hz, 1H, H-6), 4.26-4.17 (m, 2H, H-5; H-9$_b$), 3.85 (s, 3H, OMe), 2.19 (s, 3H, Me, OAc), 2.18 (s, 3H, Me, OAc), 2.11 (s, 3H, Me, OAc), 2.05 (s, 3H, Me, OAc), 2.04 (s, 3H, Me, OAc). $^{13}$C NMR (126 MHz, CDCl$_3$) δ 171.70 (CO, Ac), 170.78 (CO, Ac), 170.76 (CO, Ac), 170.51 (CO, Ac), 167.22 (C-1), 164.94 (CO, Ac), 157.68 (q, J=37.8 Hz, CO, TFA), 115.50 (q, J=288.4 Hz, CF$_3$), 95.16 (d, J=29.0 Hz, C-2), 86.90 (d, J=186.1 Hz, C-3), 71.27 (C-8), 71.00 (C-6), 68.00 (d, J=16.9 Hz, C-4), 67.91 (C-7), 62.06 (C-9), 53.75 (OMe), 46.43 (d, J=2.4 Hz, C-5), 20.99 (Me, OAc), 20.82 (Me, OAc), 20.80 (Me, OAc), 20.60 (Me, OAc), 20.56 (Me, OAc). HR-ESI-TOF/MS (m/z): [M+Na]$^+$ calcd. for C$_{22}$H$_{27}$F$_4$NNaO$_{14}$, 628.12654; found, 628.12591.

Methyl 5-(acetoxyamido)-2,4,7,8,9-penta-O-acetyl-3,5-dideoxy-3-fluoro-D-glycero-β-galacto-non-2-ulopyranosonate (11)

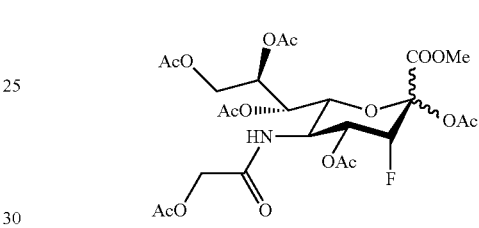

Boc inhibitor 9 (40 mg; 66 µmol) was dissolved in a 1:1:2 mixture of DCM, H$_2$O and TFA (0.7 ml; 0.1 M). The mixture was stirred for 2 hrs at r.t. (TLC: (EtOAc:Hept, 60:40 v/v) R$_f$=0.09). The mixture was then diluted with H$_2$O and concentrated in vacuo. The residue was dissolved in DCM (0.7 ml; 0.1 M) and successively acetoxyacetyl chloride (11 µl; 97 µmol; 1.5 eq.) and TEA (45 µl; 324 mol; 5 eq) were added. After stirring at r.t. overnight the mixture was diluted with DCM and washed successively with 0.1M HCl and sat. NaHCO$_3$. The organic layer was dried over MgSO$_4$, filtered and concentrated in vacuo. Silicagel flash column chromatography (0%→60% EtOAc in Hept) afforded 11 (17 mg; 28 µmol; 43%) as a white solid. TLC: (EtOAc:Hept, 80:20 v/v) R$_f$=0.19. $^1$H NMR (500 MHz, CDCl$_3$) δ 6.18 (d, J=9.0 Hz, 1H, NH), 5.64 (ddd, J=27.9, 11.0, 2.5 Hz, 1H, H-4), 5.28 (dd, J=5.3, 2.0 Hz, 1H, H-7), 5.13 (ddd, J=6.3, 5.2, 2.4 Hz, 1H, H-8), 4.95 (dd, J=49.1, 2.5 Hz, 1H, H-3), 4.61 (d, J=15.3 Hz, 1H, CHH Glc), 4.56 (dd, J=12.5, 2.4 Hz, 1H, H-9$_a$), 4.32 (d, J=15.3 Hz, 1H, CHH Gc), 4.30-4.26 (m, 1H, H-6), 4.22-4.15 (m, 2H, H-9$_b$; H-5), 3.84 (s, 3H, OMe), 2.20 (s, 3H, Me, OAc), 2.19 (s, 3H, Me, OAc), 2.17 (s, 3H, Me, OAc), 2.11 (s, 3H, Me, OAc), 2.05 (s, 3H, Me, OAc), 2.05 (s, 3H, Me, OAc). $^{13}$C NMR (126 MHz, CDCl$_3$) δ 171.05 (CO, Ac), 170.88 (CO, Ac), 170.83 (CO, Ac), 170.53 (CO, Ac), 169.98 (CO, Ac), 168.03 (CO, Ac), 167.35 (CO, C-1), 165.23 (CO, NHGc), 95.38 (d, J=29.0 Hz, C-2), 87.28 (d, J=185.5 Hz, C-3), 71.91 (C-6), 71.41 (C-8), 68.27 (C-7), 67.98 (d, J=17.1 Hz, C-4), 63.01 (CH$_2$, Gc), 62.20 (C-9), 53.76 (OMe), 45.88 (d, J=2.6 Hz, C-5), 21.11 (Me, OAc), 21.07 (Me, OAc), 20.95 (Me, OAc), 20.85 (2×Me, OAc), 20.80 (Me, OAc). HR-ESI-TOF/MS (m/z): [M+Na]$^+$ calcd. for C$_{24}$H$_{32}$FNNaO$_{16}$, 632.16028; found, 632.15804.

Reference Compound: Methyl 5-(azidoacetamido)-2,4,7,8,9-penta-O-acetyl-3,5-dideoxy-3-fluoro-D-glycero-β-galacto-non-2-ulopyranosonate (12)

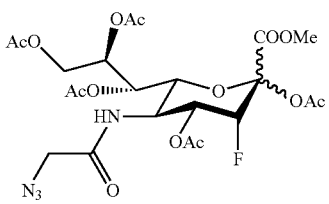

Boc inhibitor 9 (20 mg; 33 μmol) was dissolved in a 1:1:2 mixture of respectively DCM, H$_2$O and TFA (0.65 ml; 0.05 M). The mixture was stirred for 2 hrs at r.t. (TLC: (EtOAc:Hept, 60:40 v/v) R$_f$=0.09). The mixture was then diluted with water and concentrated in vacuo. The residue was dissolved in DCM (0.33 ml; 0.1 M) and successively AzOSu (42 mg; 167 μmol; 5 eq.), Pyr (27 μl; 334 μmol; 10 eq.) and DMAP (2 mg, 17 μmol; 0.5 eq.) were added. After stirring at r.t. for 23 hrs the mixture was diluted with DCM and washed successively with 0.1 M HCl and sat. NaHCO$_3$. The organic layer was dried over MgSO$_4$, filtered and concentrated in vacuo. Silicagel flash column chromatography (0%→50% EtOAc in Hept) afforded 12 (3.1 mg; 5.2 μmol; 16%). TLC: (EtOAc:Hept, 60:40 v/v) R$_f$=0.20. $^1$H NMR (500 MHz, CDCl$_3$) δ 6.31 (d, J=8.6 Hz, 1H, NH), 5.54 (ddd, J=27.5, 10.6, 2.5 Hz, 1H, H-4), 5.34 (dd, J=5.3, 1.8 Hz, 1H, H-7), 5.13 (td, J=5.7, 2.4 Hz, 1H, H-8), 4.95 (dd, J=49.0, 2.5 Hz, 1H, H-3), 4.55 (dd, J=12.5, 2.4 Hz, 1H, H-9$_a$), 4.30-4.22 (m, 2H, H-5; H-6), 4.19 (dd, J=12.6, 6.3 Hz, 1H, H-9$_b$), 3.94-3.83 (m, 5H, CH$_2$ NAz; OMe), 2.20 (s, 3H, Me, OAc), 2.16 (s, 3H, Me, OAc), 2.11 (s, 3H, Me, OAc), 2.05 (s, 3H, Me, OAc), 2.04 (s, 3H, Me, OAc). $^{13}$C NMR (126 MHz, CDCl$_3$) δ 170.94 (CO, Ac), 170.84 (CO, Ac), 170.66 (CO, Ac), 170.47 (CO, Ac), 167.52 (CO, Ac), 167.31 (C-1), 165.20 (CO, Az), 95.64 (d, J=185.7 Hz, C-2), 87.16 (d, J=185.7 Hz, C-3), 71.95 (C-6), 71.43 (C-8), 68.49 (d, J=17.2 Hz, C-4), 68.02 (C-7), 62.16 (C-9), 53.82 (OMe), 52.89 (CH$_2$, Az), 49.50 (C-5), 21.13 (Me, OAc), 21.06 (Me, OAc), 21.00 (Me, OAc), 20.91 (Me, OAc), 20.81 (Me, OAc). HR-ESI-TOF/MS (m/z): [M+Na]$^+$ calcd. for C$_{22}$H$_{29}$FN$_4$NaO$_{14}$, 615.15620; found, 615.15758.

Reference Compound: Methyl 5-(4-pentynacetamido)-2,4,7,8,9-penta-O-acetyl-3,5-dideoxy-3-fluoro-D-glycero-β-galacto-non-2-ulopyranosonate (13)

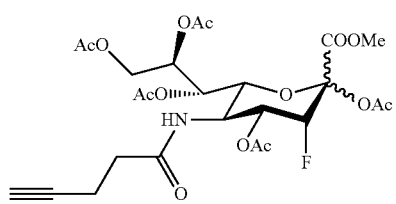

Boc inhibitor 9 (50 mg; 82 μmol) was dissolved in a 1:1:2 mixture of respectively TFA, H$_2$O and DCM (1.6 ml; 0.05 M). The mixture was stirred for 2 hrs at r.t. (TLC: (EtOAc: Hept, 60:40 v/v) R$_f$=0.09). The mixture was then diluted with water and concentrated in vacuo. The residue was dissolved in DCM (0.83 ml; 0.1 M) and successively 4-Pentynoic acid-OSu (226 mg; 1.158 mmol; 14 eq.) and TEA (69 μl; 495 μmol; 6 eq.) were added. After stirring at r.t. overnight the mixture was diluted with DCM and washed successively with 0.1M HCl and sat. aq. NaHCO$_3$. The organic layer was dried over MgSO$_4$, filtered and concentrated in vacuo. Silicagel flash column chromatography (0%→55% EtOAc in Hept) afforded 13 (3.3 mg; 5.60 μmol; 7%) as a white solid. TLC: (EtOAc:Hept, 60:40 v/v) R$_f$=0.09. $^1$H NMR (500 MHz, CDCl$_3$) δ 5.60 (ddd, J=27.9, 11.0, 2.6 Hz, 1H, H-4), 5.54 (d, J=9.0 Hz, 1H, NH), 5.37 (dd, J=5.5, 2.0 Hz, 1H, H-7), 5.15 (ddd, J=6.3, 5.4, 2.5 Hz, 1H, H-8), 4.95 (dd, J=49.1, 2.5 Hz, 1H, H-3), 4.53 (dd, J=12.5, 2.4 Hz, 1H, H-9$_a$), 4.30-4.26 (m, 1H, H-6), 4.21 (dd, J=12.5, 6.3 Hz, 1H, H-9$_b$), 4.13 (q, J=10.3 Hz, 1H, H-5), 3.84 (s, 3H, OMe), 2.56-2.44 (m, 2H, CH$_2$C≡CH), 2.40-2.27 (m, 2H, CH$_2$—CONH), 2.19 (s, 3H, Me, OAc), 2.16 (s, 3H, Me, OAc), 2.11 (s, 3H, Me, OAc), 2.04 (s, 3H, Me, OAc), 2.04 (s, 3H, Me, OAc), 2.02 (t, J=2.6 Hz, 1H, HC≡C). $^{13}$C NMR (126 MHz, CDCl$_3$) δ 171.38 (CO, Ac), 170.85 (CO, Ac), 170.69 (CO, AC), 170.53 (CO, Ac), 170.31 (CO, Ac), 167.28 (C-1), 165.21 (CONH), 95.29 (d, J=29.0 Hz, C-2), 87.12 (d, J=185.1 Hz, C-3), 82.88 (HC≡C), 71.75 (C-6), 71.21 (C-8), 69.79 (HC≡C), 68.33-68.14 (m, C-4; C-7), 62.22 (C-9), 53.65 (OMe), 46.01 (C-5), 35.67 (CH$_2$CONH), 21.02 (Me, OAc), 20.98 (Me, OAc), 20.93 (Me, OAc), 20.92 (Me, OAc), 20.74 (Me, OAc), 14.80 (CH$_2$C≡CH). HR-ESI-TOF/MS (m/z): [M+Na]$^+$ calcd. for C$_{25}$H$_{32}$FNNaO$_{14}$, 612.17045; found, 612.16924.

Methyl 5-(propargylcarbamado)-2,4,7,8,9-penta-O-acetyl-3,5-dideoxy-3-fluoro-D-glycero-β-galacto-non-2-ulopyranosonate (14)

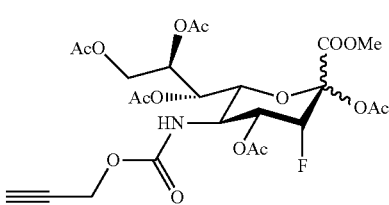

Boc inhibitor 9 (50 mg; 82 μmol) was dissolved in a 1:1:2 mixture of respectively DCM, H$_2$O and TFA (1.6 ml; 0.05 M). The mixture was stirred for 2 hrs at r.t. (TLC: (EtOAc: Hept, 60:40 v/v) R$_f$=0.09). The mixture was then diluted with H$_2$O and concentrated in vacuo. The residue was dissolved in DCM (0.83 ml; 0.1 M) and successively PocOSu (98 mg; 497 μmol; 6 eq.) and TEA (35 μl; 248 μmol; 3 eq.) were added. After stirring at r.t. for 15 hrs the mixture was diluted with DCM and washed successively with 0.1 M HCl and sat. aq. NaHCO$_{03}$. The organic layer was dried over MgSO$_4$, filtered and concentrated in vacuo. Silicagel flash column chromatography (0%→60% EtOAc in Hept) afforded 14 (20 mg; 83 μmol; 40%) as a white solid. TLC: (EtOAc:Hept, 60:40 v/v) R$_f$=0.36. $^1$H NMR (500 MHz, CDCl$_3$) δ 5.53 (dd, J=26.9, 10.8 Hz, 1H, H-4), 5.39-5.36 (m, 1H, H-7), 5.18 (td, J=5.9, 2.5 Hz, 1H, H-8), 4.95 (dd, J=49.1, 2.5 Hz, 1H, H-3), 4.87 (d, J=9.5 Hz, 1H, NH), 4.73 (ddd, J=15.5, 5.4, 2.5 Hz, 1H, CHH. Poc), 4.57-4.49 (m, 2H, CHH, Poc; H-9$_a$), 4.23-4.17 (m, 2H, H9$_b$; H-6), 3.95-3.86

(m, 1H, H-5), 3.84 (s, 3H, OMe), 2.47 (t, J=2.4 Hz, 1H, C≡CH, Poc), 2.18 (s, 3H, Me, OAc), 2.17 (s, 3H, Me, OAc), 2.13 (s, 3H, Me, OAc), 2.05 (s, 3H, Me, OAc), 2.04 (s, 3H, Me, OAc). $^{13}$C NMR (126 MHz, CDCl$_3$) δ 170.75 (CO, Ac), 170.69 (CO, Ac), 170.46 (CO, Ac), 170.24 (CO, Ac), 167.27 (C-1), 165.17 (CO, Ac), 154.75 (CO, Poc), 95.20 (d, J=28.8 Hz, C-2), 87.18 (d, J=185.1 Hz, C-3), 77.95 (C≡CH, Poc), 75.00 (C≡CH, Poc), 71.89 (C-6), 71.00 (C-8), 68.32-67.98 (m, C-4; C-7), 62.20 (C-9), 53.66 (OMe), 53.16 (CH$_2$, Poc), 47.37 (C-5), 21.00 (Me, OAc), 20.94 (Me, OAc), 20.92 (Me, OAc), 20.82 (Me, OAc), 20.72 (Me, OAc). HR-ESI-TOF/MS (m/z): [M+Na]$^+$ calcd. for C$_{24}$H$_{30}$FNNaO$_{15}$, 614.14972; found, 614.15007.

5-(alloxycarbamado)-2,4,7,8,9-penta-O-acetyl-3,5-dideoxy-3-fluoro-D-glycero-β-galacto-non-2-ulopyranosonate (15)

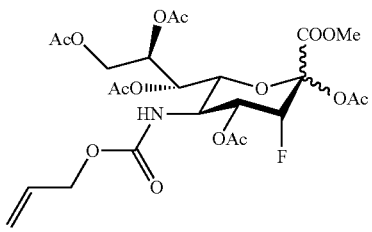

15

Boc inhibitor 9 (50 mg; 82 µmol) was dissolved in a 1:1:2 mixture of respectively TFA, H$_2$O and DCM (1.6 ml; 0.05 M). The mixture was stirred for 2 hrs at r.t. (TLC: (EtOAc: Hept, 60:40 v/v) R$_f$=0.09). The mixture was then diluted with water and concentrated in vacuo. The residue was dissolved in DCM (0.83 ml; 0.1 M) and Alloc-Cl (11 µl; 99 µmol; 1.2 eq.) and TEA (69 µl; 495 µmol; 6 eq.) were added. After stirring at r.t. for 1 hr additional Alloc-Cl (18 µl; 165 µmol; 2 eq.) was added. The reaction was stirred for 15 hrs after which the reaction was still not finished, so additional Alloc-Cl (90 µl; 844 µmol; 10.2 eq.) and TEA (35 µl; 252 µmol; 3 eq.) were added. After stirring at r.t. for 5.5 hrs the mixture was diluted with DCM and washed successively with 0.1M HCl and sat. NaHCO$_3$. The organic layer was dried over MgSO$_4$, filtered and concentrated in vacuo. Silicagel flash column chromatography (0%→50% EtOAc in Hept) afforded 15 (7.7 mg; 13 µmol; 16%) as a white solid. TLC: (EtOAc:Hept, 60:40 v/v) R$_f$=0.32. $^1$H NMR (500 MHz, CDCl$_3$) δ 5.89 (tdd, J=16.1, 8.3, 3.3 Hz, 1H, CHH=CH, Alloc), 5.54 (dd, J=27.7, 10.9 Hz, 1H, H-4), 5.39 (dd, J=5.5, 2.0 Hz, 1H, H-7), 5.28 (dd, J=16.1, 2.4 Hz, 1H, CHH=CH, Alloc), 5.21 (d, J=11.2 Hz, 1H, CHH=CH, Alloc), 5.18 (td, J=6.0, 2.5 Hz, 1H, H-8), 4.95 (dd, J=49.1, 2.5 Hz, 1H, H-3), 4.79 (d, J=9.3 Hz, 1H, NH), 4.60-4.45 (m, 3H, H-9$_a$; OCH$_2$ Alloc), 4.24-4.17 (m, 2H, H-6; H-9$_b$), 3.94-3.87 (m, 1H, H-5), 3.84 (s, 3H, OMe), 2.18 (s, 3H, Me, OAc), 2.17 (s, 3H, Me, OAc), 2.11 (s, 3H, Me, OAc), 2.05 (s, 3H, Me, OAc), 2.04 (s, 3H, Me, OAc). $^{13}$C NMR (126 MHz, CDCl$_3$) δ 170.75 (CO, Ac), 170.66 (CO, Ac), 170.45 (CO, Ac), 170.27 (CO, Ac), 167.30 (C-1), 165.22 (CO, Ac), 155.41 (CO, Alloc), 132.65 (CH$_2$=CH, Alloc), 117.84 (CH$_2$=CH, Alloc), 95.21 (d, J=28.8 Hz, C-2), 87.20 (d, J=184.9 Hz, C-3), 71.98 (C-6), 71.07 (C-8), 68.17-67.92 (C-4; C-7), 66.09 (OCH$_2$, Alloc), 62.24 (C-9), 53.64 (OMe), 47.22 (C-5), 20.99 (Me, OAc), 20.93 (Me, OAc), 20.91 (Me, OAc), 20.80 (Me, OAc), 20.71 (Me, OAc). HR-ESI-TOF/MS (m/z): [M+Na]$^+$ calcd. for C$_{24}$H$_{32}$FNNaO$_{15}$, 616.16537; found, 616.16544.

Methyl 5-(methylcarbamado)-2,4,7,8,9-penta-O-acetyl-3,5-dideoxy-3-fluoro-D-glycero-β-galacto-non-2-ulopyranosonate (16)

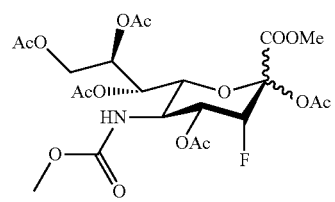

16

Boc inhibitor 9 (50 mg; 82 µmol) was dissolved in a 1:1:3 mixture of respectively TFA, water and DCM (1.6 ml; 0.05 M). The mixture was stirred for 2 hrs at r.t. (TLC: (EtOAc: Hept, 60:40 v/v) R$_f$=0.09). The mixture was then diluted with H$_2$O and concentrated in vacuo. The residue was dissolved in DCM (0.8 ml; 0.1 M) and Me-chloroformate (183 µl; 1.649 mmol; 20 eq.) and TEA (229 µl; 1.649 mmol; 20 eq.) were added. The reaction was stirred at r.t. overnight after which the mixture was diluted with DCM and washed successively with 0.1M HCl and sat. NaHCO$_3$. The organic layer was dried over MgSO$_4$, filtered and concentrated in vacuo. Silicagel flash column chromatography (0%→50% EtOAc in Hept) afforded 16 (16 mg; 27 µmol; 33%). TLC: (EtOAc:Hept:MeOH, 45:45:10 v/v) R$_f$=0.27. $^1$H NMR (400 MHz, CDCl$_3$) δ 5.59-5.47 (m, 1H, H-4), 5.41-5.38 (m, 1H, H-7), 5.17 (ddd, J=6.3, 5.3, 2.5 Hz, 1H, H-8), 4.95 (dd, J=49.1, 2.6 Hz, 1H, H-3), 4.77 (d, J=9.2 Hz, 1H, NH), 4.54 (dd, J=12.5, 2.6 Hz, 1H, H-9$_a$), 4.25-4.17 (m, 2H, H-9$_b$; H-6), 3.88-3.85 (m, 1H, H-5), 3.84 (s, 3H, MeO—C-1), 3.64 (s, 3H, MeO—CONH), 2.18 (s, 3H, Me, OAc), 2.17 (s, 3H, Me, OAc), 2.12 (s, 3H, Me, OAc), 2.05 (s, 3H, Me, OAc), 2.04 (s, 3H, Me, OAc). $^{13}$C NMR (101 MHz, CDCl$_3$) δ 170.73 (2×CO, Ac), 170.45 (CO, Ac), 170.30 (CO, Ac), 167.30 (C-1), 165.21 (CO, Ac), 156.17 (NHCO), 95.20 (d, J=28.7 Hz, C-2), 87.18 (d, J=184.8 Hz, C-3), 72.04 (C$_6$), 71.20 (C-8), 68.42-68.16 (m, C-4; C-7), 62.26 (C-9), 53.62 (MeO—C1), 52.76 (MeO—CONH), 47.26 (C-5), 20.99 (Me, OAc), 20.91 (Me, OAc), 20.90 (Me, OAc), 20.78 (Me, OAc), 20.68 (Me, OAc). HR-ESI-TOF/MS (m/z): [M+Na]$^+$ calcd. for C$_{22}$H$_{30}$FNNaO$_{15}$, 590.14972; found, 590.14874.

Methyl 5-(ethylcarbamado)-2,4,7,8,9-penta-O-acetyl-3,5-dideoxy-3-fluoro-D-glycero-β-galacto-non-2-ulopyranosonate (17)

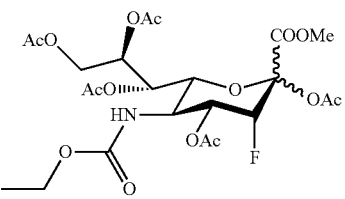

17

Boc inhibitor 9 (50 mg; 82 µmol) was dissolved in a 1:1:3 mixture of respectively TFA, water and DCM (1.6 ml; 0.05 M). The mixture was stirred for 2 hrs at r.t. (TLC: (EtOAc: Hept, 60:40 v/v) $R_f$=0.09). The mixture was then diluted with water and concentrated in vacuo. The 1 residue was dissolved in DCM (0.8 ml; 0.1 M) and Et-chloroformate (197 µl; 1.649 mmol; 20 eq.) and TEA (229 µl; 1.649 mmol; 20 eq.) were added. The reaction was stirred at r.t. overnight after which the mixture was diluted with DCM and washed successively with 0.1M HCl and sat. NaHCO$_3$. The organic layer was dried over MgSO$_4$, filtered and concentrated in vacuo. Silicagel flash column chromatography (0%→50% EtOAc in Hept) afforded 17 (8 mg; 13 µmol; 16%). TLC: (EtOAc:Hept:MeOH, 45:45:10 v/v) $R_f$=0.28. $^1$H NMR (400 MHz, CDCl$_3$) δ 5.58-5.46 (m, 1H, H-4), 5.40 (dt, J=5.0, 2.4 Hz, 1H, H-7), 5.18 (td, J=5.8, 2.7 Hz, 1H, H-8), 4.95 (dd, J=49.2, 2.5 Hz, 1H, H-3), 4.65 (d, J=9.3 Hz, 1H, NH), 4.57-4.51 (m, 1H, H-9$_a$), 4.24-4.16 (m, 2H, H-9$_b$; H6), 4.11-4.03 (m, 2H, CH$_2$, Et), 3.90 (d, J=10.3 Hz, 1H, H-5), 3.84 (s, 3H, OMe), 2.18 (s, 3H, Me, OAc), 2.17 (s, 3H, Me, OAc), 2.12 (s, 3H, Me, OAc), 2.05 (s, 3H, Me, OAc), 2.04 (s, 3H, Me, OAc), 1.25-1.20 (m, 3H, Me, Et). $^{13}$C NMR (101 MHz, CDCl$_3$) δ 170.73 (CO, Ac), 170.66 (CO, Ac), 170.42 (CO, Ac), 170.29 (CO, Ac), 167.27 (C-1), 165.42 (CO, Ac), 155.74 (CONH), 95.24 (d, J=28.6 Hz, C-2), 87.23 (d, J=184.8 Hz, C-3), 72.15 (C-6), 71.16 (C-8), 68.20 (C-4), 67.89 (C-7), 62.27 (C-9), 61.63 (CH$_2$, Et), 53.62 (OMe), 47.13 (C-5), 20.99 (Me, OAc), 20.93 (Me, OAc), 20.91 (Me, OAc), 20.78 (Me, OAc), 20.71 (Me, OAc), 14.62 (Me, Et). HR-ESI-TOF/MS (m/z): [M+Na]$^+$ calcd. for C$_{23}$H$_{32}$FNNaO$_{15}$, 604.16537; found, 604.16438.

Methyl 5-(isobutylcarbamado)-2,4,7,8,9-penta-O-acetyl-3,5-dideoxy-3-fluoro-D-glycero-β-galacto-non-2-ulopyranosonate (18)

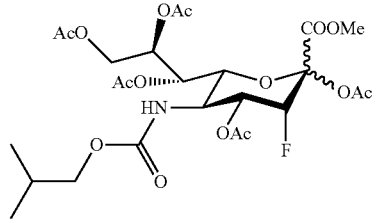

Boc inhibitor 9 (18 mg; 30 µmol) was dissolved in a 1:1:3 mixture of respectively TFA, H$_2$O and DCM (0.6 ml; 0.05 M). The mixture was stirred for 2 hrs at r.t. (TLC: (EtOAc: Hept, 60:40 v/v) $R_f$0.09). The mixture was then diluted with H$_2$O and concentrated in vacuo. The mixture was redissolved in Tol and concentrated in vacuo three times. The residue was then dissolved in DCM (0.3 ml; 0.1 M) and $^i$Bu chloroformate (76 µl; 589 µmol; 20 eq.) and TEA (82 µl; 589 µmol; 20 eq.) were added. The reaction was stirred at r.t. overnight after which the mixture was diluted with DCM and washed successively with 0.1M HCl and sat. NaHCO$_3$. The organic layer was dried over MgSO$_4$, filtered and concentrated in vacuo. Silicagel flash column chromatography (0%→50% EtOAc in Hept) afforded 9 (6 mg; 9.8 µmol; 33%). TLC: (EtOAc:Hept:MeOH, 45:45:10 v/v) $R_f$=0.40. $^1$H NMR (400 MHz, CDCl$_3$) δ 5.64-5.49 (m, 1H, H-4), 5.42-5.37 (m, 1H, H-7), 5.18 (td, J=6.0, 2.5 Hz, 1H, H-8), 4.95 (dd, J=49.2, 2.5 Hz, 1H, H-3), 4.73 (d, J=9.1 Hz, 1H, NH), 4.53 (dd, J=12.5, 2.5 Hz, 1H, H-9$_a$), 4.25-4.17 (m, 2H, H-9$_b$; H-6), 3.92-3.75 (m, 6H, H-5; OMe; CH$_2$, $^i$Bu), 2.18 (s, 3H, Me, OAc), 2.17 (s, 3H, Me, OAc), 2.11 (s, 3H, Me, OAc), 2.04 (s, 3H, Me, OAc), 2.04 (s, 3H, Me, OAc), 1.95-1.84 (m, 1H, CH, $^i$Bu), 0.90 (d, J=6.8 Hz, 6H, 2×Me, $^i$Bu). $^{13}$C NMR (101 MHz, CDCl$_3$) δ 170.72 (CO, Ac), 170.39 (CO, Ac), 170.21 (CO, Ac), 170.00 (CO, Ac), 167.28 (C-1), 165.24 (CO, Ac), 155.87 (CONH), 95.25 (d, J=29.0 Hz, C-2), 87.24 (d, J=184.8 Hz, C-3), 72.00 (C-6), 71.56 (CH$_2$, $^i$Bu), 71.06 (C-8), 68.16-68.01 (m, C-7; C-4), 62.21 (C-9), 53.62 (OMe), 47.18 (C-5), 28.05 (CH$_2$, $^i$Bu), 20.98 (Me, OAc), 20.92 (Me, OAc), 20.89 (Me, OAc), 20.75 (Me, OAc), 20.70 (Me, OAc), 19.02 (2×Me, $^i$Bu) HR-ESI-TOF/MS (m/z): [M+Na]$^+$ calcd. for C$_{25}$H$_{36}$FNNaO$_{15}$, 632.19667; found, 632.19698.

Reference Compound: Methyl 5-(chloroacetamido)-2,4,7,8,9-penta-O-acetyl-3,5-dideoxy-3-fluoro-D-glycero-β-galacto-non-2-ulopyranosonate (19)

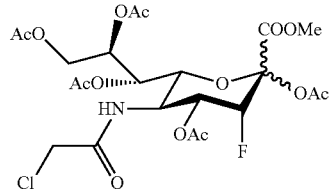

Boc inhibitor 9 (200 mg; 329 µmol) was dissolved in a 1:1:2 mixture of DCM, H$_2$O and TFA (3.3 mL; 0.1 M). The mixture was stirred for 2 hrs at r.t. (TLC: (EtOAc:Hept, 60:40 v/v) $R_f$=0.09). The mixture was then diluted with H$_2$O and concentrated in vacuo. The residue was dissolved in DCM (3.3 mL; 0.1 M) and successively ClAcCl (39 µL; 492 µmol; 1.5 eq.) and TEA (273 µL; 1.97 mmol; 6 eq.) were added. After stirring at r.t. overnight the mixture was concentrated in vacuo. The residue was dissolved in EtOAc and washed with sat. aq. NaHCO$_3$. The organic layer was dried over MgSO$_4$, filtered and concentrated in vacuo. Silicagel flash column chromatography (0%→50% EtOAc in Hept) afforded 19 (116 mg; 198 µmol; 60%) as a white solid. TLC: (EtOAc:Hept, 80:20 v/v) $R_f$=0.48) $^1$H NMR (500 MHz, CDCl$_3$) δ 6.63 (d, J=8.6 Hz, 1H, NH), 5.58 (ddd, J=27.5, 10.6, 2.5 Hz, 1H, H-4), 5.34 (dd, J=5.2, 1.8 Hz, 1H, H-7), 5.12 (ddd, J=6.4, 5.1, 2.4 Hz, 1H, H-8), 4.95 (dd, J=49.0, 2.5 Hz, 1H, H-3), 4.59 (dd, J=12.5, 2.5 Hz, 1H, H-9$_a$), 4.33-4.23 (m, 2H, H-6; H-5), 4.21 (dd, J=12.5, 6.5 Hz, 1H, H-9$_b$), 4.02-3.93 (m, 2H, CH$_2$, ClAc), 3.85 (s, 3H, OMe), 2.19 (s, 3H, Me, OAc), 2.16 (s, 3H, Me, OAc), 2.12 (s, 3H, Me, OAc), 2.06 (s, 3H, Me, OAc), 2.04 (s, 3H, Me, OAc). $^{13}$C NMR (126 MHz, CDCl$_3$) δ 170.77 (CO, Ac), 170.66 (CO, Ac), 170.61 (CO, Ac), 170.47 (CO, Ac), 167.23 (C-1), 166.73 (CO, Ac), 165.08 (CO, ClAc), 95.28 (d, J=29.0 Hz, C-2). 87.01 (d, J=185.7 Hz, C-3), 71.79 (C-6), 71.50 (C-8), 68.14 (d, J=17.2 Hz, C-4), 67.88 (C-7), 62.15 (C-9), 53.68 (OMe), 45.91 (d, J=2.6 Hz, C-5), 42.56 (CH$_2$, ClAc), 21.03

(Me, Ac), 20.91 (Me, Ac), 20.86 (Me, Ac), 20.76 (Me, Ac), 20.66 (Me, Ac). HR-ESI-TOF/MS (m/z): [M+Na]$^+$ calcd. for $C_{22}H_{29}ClFNNaO_{14}$, 608.11583; found, 608.11438.

Reference Compound: Methyl 5-(benzylcarbamado)-2,4,7,8,9-penta-O-acetyl-3,5-dideoxy-3-fluoro-D-glycero-β-galacto-non-2-ulopyranosonate (20)

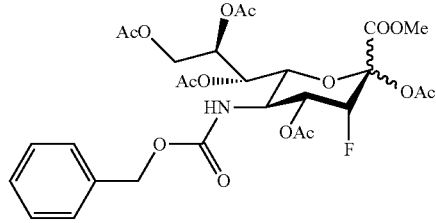

Boc inhibitor 9 (50 mg; 82 μmol) was dissolved in a 1:1:2 mixture of respectively TFA, H$_2$O and DCM (1.6 mL; 0.05 M). The mixture was stirred for 2 hrs at r.t. (TLC: (EtOAc:Hept, 60:40 v/v) R$_f$=0.09). The mixture was then diluted with H$_2$O and concentrated in vacuo. The residue was dissolved in DCM (0.83 mL; 0.1 M) and Cbz-Cl (14 μl; 99 μmol; 1.2 eq.) and TEA (69 μl; 495 μmol; 6 eq.) were added. After stirring at r.t. for 1 hr additional Cbz-Cl (24 μl; 165 μmol; 2 eq.) was added. The reaction was stirred for 15 hrs after which the reaction was still not finished, so additional Cbz-Cl (125 μl; 874 μmol; 10.5 eq.) and TEA (35 μl; 252 μmol; 3 eq.) were added. After stirring at r.t. for 5.5 hrs the mixture was diluted with DCM and washed successively with 0.1M HCl and sat. NaHCO$_{03}$. The organic layer was dried over MgSO$_4$, filtered and concentrated in vacuo. Silicagel flash column chromatography (0%→50% EtOAc in Hept) afforded 20 (3.3 mg; 5.1 μmol; 6%) as a white solid. TLC: (EtOAc:Hept, 60:40 v/v) R$_f$=0.43. $^1$H NMR (500 MHz, CDCl$_3$) δ 7.37-7.30 (m, 5H, 5×CH, Cbz), 5.52 (dd, J=27.7, 11.0 Hz, 1H, H-4), 5.41 (dd, J=5.8, 2.0 Hz, 1H, H-7), 5.18 (td, J=5.9, 2.6 Hz, 1H, H-8), 5.15 (d, J=12.4 Hz, 1H, CHH, Cbz), 5.02-4.88 (m, 2H, CHH, Cbz; H-3), 4.78 (d, J=9.5 Hz, 1H, NH), 4.56-4.49 (m, 1H, H-9$_a$), 4.24-4.17 (m, 2H, H9$_b$; H-6), 3.91 (q, J=10.5 Hz, 1H, H-5), 3.83 (s, 3H, OMe), 2.16 (s, 3H, Me, OAc), 2.17 (s, 3H, Me, OAc), 2.03 (s, 3H, Me, OAc), 2.02 (s, 3H, Me, OAc), 1.97 (s, 3H, Me, OAc). $^{13}$C NMR (126 MHz, CDCl$_3$) δ 170.74 (CO, Ac), 170.64 (CO, Ac), 170.43 (CO, Ac), 170.20 (CO, Ac), 167.26 (C-1), 165.21 (CO, Ac), 155.54 (CO, Cbz), 136.39 (C, Cbz), 128.68 (2×CH, ortho Cbz), 128.36 (CH, para Cbz), 128.15 (2×CH, meta Cbz), 95.22 (d, J=29.0 Hz, C-2), 87.21 (d, J=184.9 Hz, C-3), 71.99 (C-6), 70.98 (C-8), 68.11-67.91 (m, C-4; C-7), 67.18 (CH$_2$, Cbz), 62.21 (C-9), 53.64 (OMe), 47.27 (C-5), 20.97 (Me, OAc), 20.94 (Me, OAc), 20.92 (Me, OAc), 20.72 (Me, OAc), 20.62 (Me, OAc). HR-ESI-TOF/MS (m/z): [M+Na]$^+$ calcd. for $C_{28}H_{34}FNNaO_{15}$, 666.18102; found, 666.18010.

Reference Compound: Methyl 5-[(1-benzyl-1H-1,2,3-triazol-4-yl)methylcarbamado]-2,4,7,8,9-penta-O-acetyl-3,5-dideoxy-3-fluoro-D-glycero-β-galacto-non-2-ulopyranosonate (21)

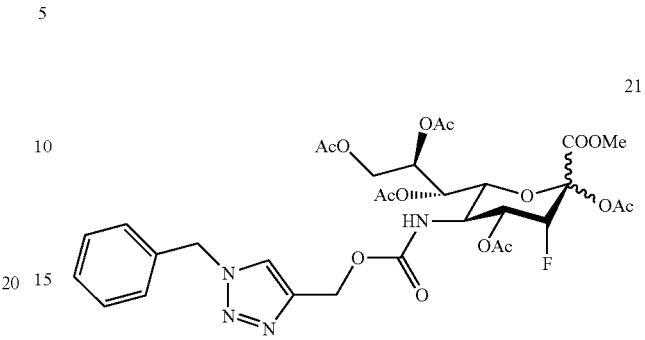

To a mixture of 14 (10 mg; 17 μmol) in a 1:9 mixture of H$_2$O and $^t$BuOH (0.19 ml; 0.09 M), Bn-N$_3$ (4.5 mg; 34 μmol; 2 eq.) was added. A premixture of TBTA (29 mg), DMF (750 μL) and CuI (5.1 mg) was agitated until a homogenous solution was obtained. The TBTA mixture (95 μl) was added to the H$_2$O/$^t$BuOH mixture and 10 mg of copper flakes were added. The reaction was stirred at r.t. overnight, filtered and concentrated in vacuo. Silicagel flash column chromatography (0%→80% EtOAc in Hept) afforded 21 (5.7 mg; 7.7 μmol; 46%) as a white solid. TLC: (EtOAc:Hept, 80:20 v/v) R$_f$=0.37. $^1$H NMR (500 MHz, CDCl$_3$) δ 7.64 (s, 1H, CH, triazole), 7.37 (d, J=2.2 Hz, 2H, 2×CH, ortho Bn), 7.32-7.29 (m, 2H, 2×CH, meta Bn), 6.91 (dd, J=10.3, 6.8 Hz, 1H, CH, para Bn), 5.58-5.41 (m, 2H, CH$_2$, Bn), 5.34-5.28 (m, 1H, H-7), 5.23-5.05 (m, 2H, CH$_2$, Poc), 5.00 (d, J=8.9 Hz, 1H, NH), 4.93 (dd, J=49.1, 2.5 Hz, 1H, H-3), 4.50 (dd, J=12.6, 2.6 Hz, 1H, H-9$_a$), 4.20-4.14 (m, 2H, H-9$_b$; H-6), 3.92 (q, J=10.4 Hz, 1H, H-5), 3.83 (s, 3H, OMe), 2.16 (s, 3H, Me, OAc), 2.14 (s, 3H, Me, OAc), 2.02 (s, 3H, Me, OAc), 2.02 (s, 3H, Me, OAc), 1.97 (s, 3H, Me, OAc). $^{13}$C NMR (126 MHz, CDCl$_3$) δ 170.88 (CO, Ac), 170.72 (CO, Ac), 170.52 (CO, Ac), 170.34 (CO, Ac), 167.39 (C-1), 165.27 (CO, Ac), 155.63 (CO, Poc), 134.64 (C, Bn), 129.38 (2×CH, meta Bn), 129.09 (CH, para Bn), 128.44 (2×CH, ortho Bn), 125.00 (CH, triazole), 95.25 (d, J=28.9 Hz, C-2), 87.21 (d, J=185.0 Hz, C-3), 72.15 (C-6), 71.15 (C-8), 68.47 (d, J=17.0 Hz, C-4), 68.30 (C-7), 62.30 (C-9), 58.65 (CH$_2$, Poc), 54.52 (CH$_2$, Bn), 53.74 (OMe), 47.22 (C-5), 21.07 (Me, OAc), 21.05 (Me, OAc), 21.01 (Me, OAc), 20.78 (Me, OAc), 20.74 (Me, OAc). HR-ESI-TOF/MS (m/z): [M+Na]$^+$ calcd. for $C_{31}H_{37}FN_4NaO_{15}$, 747.21371; found, 747.21371.

Methyl 5-(butylcarbamado)-2,4,7,8,9-penta-O-acetyl-3,5-dideoxy-3-fluoro-D-glycero-β-galacto-non-2-ulopyranosonate (22)

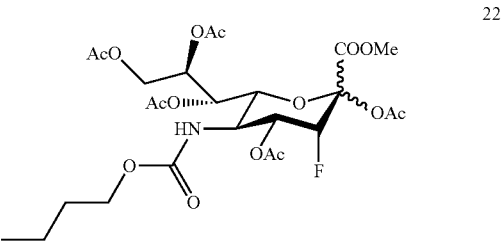

Boc inhibitor 9 (25 mg; 41 µmol) was dissolved in DCM (1 ml; 0.041 M) and TfOH (14 µl; 164 µm; 4 eq.)) was added and stirred for 5 min at r.t. (TLC: (EtOAc:Hept, 60:40 v/v) $R_f$=0.09) then n-Bu chloroformate (27 µl; 205 µm; 5 eq.) and TEA (57 µl; 410 µm; 10 eq.) were added. The reaction was left stirring for 16 hrs at r.t., diluted with an excess of DCM washed successively with 0.1M HCl and sat. NaHCO$_3$. The organic layer was dried over MgSO$_4$, filtered and concentrated in vacuo. Silicagel flash column chromatography (0%→50% EtOAc in Hept) afforded 22 (8 mg; 41 µmol; 32%) as a white solid. TLC: (EtOAc) $R_f$=0.90. $^1$H NMR (500 MHz, CDCl$_3$) δ 5.54 (dd, J=27.9, 11.3 Hz, 1H, H-4), 5.39 (d, J=5.9 Hz, 1H, H-7), 5.18 (td, J=6.0, 2.5 Hz, 1H, H-8), 4.95 (dd, J=49.2, 2.5 Hz, 1H, H-3), 4.73-4.66 (m, 1H, NH), 4.53 (dd, J=12.4, 2.6 Hz, 1H, H-9$_a$), 4.24-4.17 (m, 2H, H-9$_b$; H-6), 4.08-3.96 (m, 2H, (CO)CH$_2$, n-Bu), 3.93-3.84 (m, 1H, H-5), 3.84 (s, 3H, OMe), 2.18 (s, 3H, Me, OAc), 2.17 (s, 3H, Me, OAc), 2.11 (s, 3H, Me OAc), 2.05 (s, 3H, Me, OAc), 2.04 (s, 3H, Me, OAc), 1.61-1.54 (m, 2H, CH$_2$CH$_2$CH$_2$, n-Bu), 1.39-1.32 (m, 2H, CH$_2$CH$_3$, n-Bu), 0.93 (t, J=7.4 Hz, 3H, CH$_2$CH$_3$, n-Bu). $^{13}$C NMR (126 MHz, Chloroform-d) δ 170.59 (CO, Ac), 170.45 (CO, Ac), 170.25 (CO, Ac), 170.09 (CO, Ac), 167.14 (C-1), 165.10 (CO, Ac), 155.70 (CONH), 95.09 (d, J=28.8 Hz, C-2), 87.08 (d, J=184.7 Hz, C-3), 71.92 (C-6), 70.96 (C-8), 69.30 (d, J=13.5 Hz, C-4), 68.00 (C-7), 65.31 (C(O)CH$_2$, n-Bu), 62.09 (C-9), 53.48 (OMe), 46.99 (C-5), 30.85 (CH$_2$CH$_2$CH$_2$, n-Bu), 20.84 (Me, OAc), 20.78 (Me, OAc), 20.75 (Me, OAc), 20.62 (Me, OAc), 20.56 (Me, OAc), 18.93 (CH$_2$CH$_3$, n-Bu), 13.68 (CH$_2$CH$_3$, n-Bu). $^{19}$F NMR (470 MHz, CDCl$_3$) δ −209.10 (dd, J=49.1, 27.9 Hz). HR-ESI-TOF/MS (m/z): [M+Na]$^+$ calcd. for C$_{25}$H$_{36}$FN$_4$NaO$_{15}$, 632.19667; found, 632.19640.

Methyl 5-(2-methoxy-ethylcarbamado)-2,4,7,8,9-penta-O-acetyl-3,5-dideoxy-3-fluoro-D-glycero-R-galacto-non-2-ulopyranosonate (23)

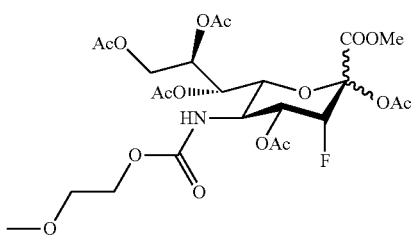

Boc inhibitor 9 (40 mg; 66 µmol) was dissolved in DCM (1 ml; 0.066 M) and TfOH (23 µl; 262 µm; 4 eq.)) was added and stirred for 5 min at r.t. (TLC: (EtOAc:Hept, 60:40 v/v) $R_f$=0.09) F then 2-methoxyethyl chloroformate (38 µl; 328 µm; 5 eq.) and TEA (91 µl; 656 µm; 10 eq.) were added. The reaction was left stirring for 16 hrs at r.t., diluted with an excess of DCM washed successively with 0.1M HCl and sat. NaHCO$_{03}$. The organic layer was dried over MgSO$_4$, filtered and concentrated in vacuo. Silicagel flash column chromatography (0%→50% EtOAc in Hept) afforded 23 (36 mg; 66 µmol; 90%) as a white solid. TLC: (EtOAc) $R_f$=0.80. $^1$H NMR (500 MHz, CDCl$_3$) δ 5.51 (ddd, J=27.9, 11.1, 3.1 Hz, 1H, H-4), 5.39 (dd, J=5.7, 1.9 Hz, 1H, H$_7$), 5.21-5.14 (m, 1H, H$_8$), 4.95 (dd, J=49.1, 2.5 Hz, 1H, H$_3$), 4.86 (d, J=9.1 Hz, 1H, NH), 4.52 (dd, J=12.5, 2.6 Hz, 1H, H9$_a$), 4.23-4.15 (m, 4H, H9$_b$, H$_6$, CH$_2$CH$_2$C(O)), 3.92-3.86 (m, 1H, H$_5$), 3.83 (s, 3H, COOMe), 3.55 (ddd, J=6.6, 5.2, 2.7 Hz, 2H, MeOCH$_2$CH$_2$), 3.37 (s, 3H, OMe), 2.17 (s, 3H, Me OAc), 2.15 (s, 3H, Me OAc), 2.11 (s, 3H, Me OAc), 2.04 (s, 3H, Me OAc), 2.03 (s, 3H, Me OAc). $^{13}$C NMR (126 MHz, CDCl$_3$) δ 170.61 (CO), 170.44 (CO), 170.26 (CO), 170.04 (CO), 167.17 (CO), 165.07 (CO), 155.43 (CONH), 95.05 (d, J=28.9 Hz, C$_2$), 87.01 (d, J=184.8 Hz, C$_3$), 71.82 (C$_6$), 70.66 (C$_8$), 70.61 CH$_2$CH$_2$C(O), 68.16 (d, J=17.1 Hz, C$_4$), 67.98 (C$_7$), 64.46 (MeOCH$_2$CH$_2$), 62.06 (C$_9$), 58.87 (OMe), 53.47 (COOCH$_3$), 46.99 (C$_5$), 20.83 (Me OAc), 20.78 (Me OAc), 20.76 (Me OAc), 20.63 (Me OAc), 20.56 (Me OAc). $^{19}$F NMR (470 MHz, CDCl$_3$) δ −209.21 (dd, J=49.2, 27.9 Hz). HR-ESI-TOF/MS (m/z): [M+Na]$^+$ calcd. for C$_{24}$H$_{34}$FNNaO$_{16}$, 634.17593; found, 634.17656.

Methyl 5-(2,2,2-trichloroethylcarbamado)-2,4,7,8,9-penta-O-acetyl-3,5-dideoxy-3-fluoro-D-glycero-β-galacto-non-2-ulopyranosonate (24)

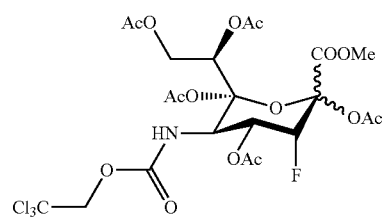

Boc inhibitor 9 (27 mg; 44 µmol) was dissolved in DCM (1 ml; 0.044 M) and TfOH (16 µl; 262 µm; 4 eq.)) was added and stirred for 5 min at r.t. (TLC: (EtOAc:Hept, 60:40 v/v) $R_f$=0.09) Troc-Cl (31 µl; 221 µm; 5 eq.) and TEA (62 µl; 443 µm; 10 eq.) were added. The reaction was left stirring for 16 hrs at r.t., diluted with an excess of DCM washed successively with 0.1M HCl and sat. NaHCO$_3$. The organic layer was dried over MgSO$_4$, filtered and concentrated in vacuo. Silicagel flash column chromatography (0%→50% EtOAc in Hept) afforded 24 (5.2 mg; 66 µmol; 17%) as a white solid. TLC: (EtOAc) $R_f$=0.85. $^1$H NMR (500 MHz, CDCl$_3$) δ 5.67 (ddd, J=27.9, 11.1, 2.5 Hz, 1H, H$_4$), 5.37 (dd, J=6.3, 1.7 Hz, 1H, H7), 5.26-5.16 (m, 2H, NH, H8), 4.97 (dd, J=49.1, 2.5 Hz, 1H, H3), 4.91 (d, 1H, CHH Troc), 4.53 (d, J=12.1 Hz, 1H, CHH Troc), 4.49 (dd, J=12.6, 2.5 Hz, 1H, H9$_a$), 4.29 (d, J=10.4 Hz, 1H, H6), 4.23 (dd, J=12.6, 5.6 Hz, 1H, H9$_b$), 3.84 (s, 3H, OMe), 3.83-3.78 (m, 1H, H5), 2.18-2.17 (m, 6H, 2×Me OAc), 2.17 (s, 3H, Me OAc), 2.04 (s, 3H, Me OAc), 2.04 (s, 3H, Me OAc). $^{13}$C NMR (126 MHz, CDCl$_3$) δ 170.75 (CO), 170.56 (CO), 170.12 (CO), 169.87 (CO), 167.04 (CO), 164.93 (CO), 153.75 (CONH), 95.05 (d, J=28.9 Hz, C2), 86.97 (d, J=184.9 Hz, C3), 95.11 (CCl$_3$ Troc), 74.33 (CH$_2$ Troc), 70.99 (C6), 70.50 (C8), 67.85 (C7), 67.62 (d, J=17.5 Hz, C4), 61.84 (C9), 53.50 (OMe), 47.43 (C5), 30.93 (Me OAc), 20.79 (Me OAc), 20.73 (Me OAc), 20.65 (Me OAc), 20.52 (Me OAc). $^{19}$F NMR (470 MHz, CDCl$_3$) δ−209.54 (dd, J=49.1, 27.7 Hz). HR-ESI-TOF/MS (m/z): [M+Na]$^+$ calcd. for C$_{23}$H$_{29}$Cl$_3$FNNaO$_{15}$, 706.04845; found, 706.04999.

Methyl 5-(2-fluoroethylcarbamado)-2,4,7,8,9-penta-O-acetyl-3,5-dideoxy-3-fluoro-D-glycero-β-galacto-non-2-ulopyranosonate (25)

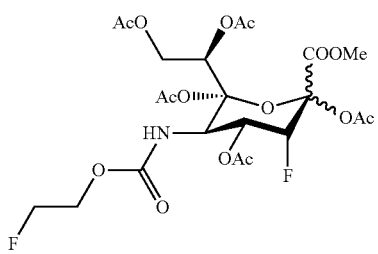

Boc inhibitor 9 (27 mg; 44 μmol) was dissolved in DCM (1 ml; 0.044 M) and TfOH (16 μl; 262 μm; 4 eq.)) was added and stirred for 5 min at r.t. (TLC: (EtOAc:Hept, 60:40 v/v) $R_f$=0.09) 2-fluoroethyl chloroformate (21 μl; 221 μm; 5 eq.) and TEA (62 μl; 443 μm; 10 eq.) were added. The reaction was left stirring for 16 hrs at r.t., diluted with an excess of DCM washed successively with 0.1M HCl and sat. NaHCO$_{O3}$. The organic layer was dried over MgSO$_4$, filtered and concentrated in vacuo. Silicagel flash column chromatography (0%→50% EtOAc in Hept) afforded 25 (16 mg; 66 μmol; 60%) as a white solid. TLC: (EtOAc) $R_f$=0.85. $^1$H NMR (500 MHz, CDCl$_3$) δ 5.51 (ddd, J=27.9, 11.0, 2.5 Hz, 1H, H4), 5.40 (dd, J=5.4, 2.0 Hz, 1H, H7), 5.17 (td, J=5.9, 2.5 Hz, 1H, H8), 4.95 (dd, J=49.1, 2.5 Hz, 1H, H3), 4.94 (d, J=9.4 Hz, 1H, NH), 4.67-4.46 (m, 3H, FCH$_2$CH$_2$, H9$_a$), 4.41-4.24 (m, 2H FCH$_2$CH$_2$), 4.25-4.16 (m, 2H, H9$_b$, H6), 4.00-3.89 (m, 1H, H5), 3.84 (s, 3H, OMe), 2.18 (s, 3H, Me OAc), 2.16 (s, 3H, Me OAc), 2.12 (s, 3H, Me OAc), 2.05 (s, 3H, Me OAc), 2.04 (s, 3H, Me OAc). $^{13}$C NMR (126 MHz, CDCl$_3$) δ 170.63 (CO), 170.48 (CO), 170.37 (CO), 170.12 (CO), 167.13 (CO), 165.04 (CO), 155.24 (CONH), 95.07 (d, J=28.7 Hz, C2), 87.03 (d, J=185.2 Hz, C3), 81.60 (d, J=170.2 Hz, FCH$_2$CH$_2$), 71.91 (C6), 71.00 (C8), 68.21 (d, J=17.3 Hz, C4), 67.96 (C7) 64.29 (d, J=19.9 Hz, FCH$_2$CH$_2$), 62.02 (C9), 53.50 (OMe), 47.05 (C5), 20.83 (Me OAc), 20.77 (Me OAc), 20.75 (Me OAc), 20.57 (Me OAc), 20.54 (Me OAc). $^{19}$F NMR (470 MHz, CDCl$_3$) δ −209.07 (dd, J=49.1, 27.9 Hz). HR-ESI-TOF/MS (m/z): [M+Na]$^+$ calcd. for C$_{23}$H$_{31}$F$_2$NNaO$_{15}$, 622.15594; found, 622.15531.

Intermediate: Methyl 5-(acetamido)-4,7,8,9-tetra-O-acetyl-2,6-anhydro-3,5-dideoxy-D-glycero-D-galacto-non-2-enonate (26)

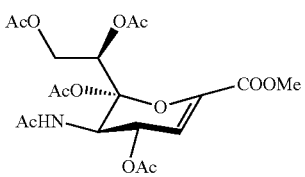

Peracetylated sialic acid 2 (1.02 g, 1.912 mmol) was dissolved in ACN (4 ml; 0.478 M) and cooled to 0° C. TMSOTf (1.03 ml; 5.736 mmol; 3 eq.) was added dropwise to the solution which turned slightly yellow. After 4 hours, the reaction was diluted with an excess EtOAc and washed three times with sat. aq. NaHCO$_3$ (30 ml). The organic layer was concentrated in vacuo and the product was purified on silicagel flash column chromatography (0→30% ACE in DCM), and 26 (0.552 g, 1.166 mmol, 61% yield) was obtained as a white foam. TLC: (Acet:DCM, 30/70) $R_f$=0.50. H NMR (400 MHz, CDCl$_3$) δ 6.05 (d, J=8.9 Hz, 1H, NH), 5.99 (d, J=3.1 Hz, 1H, H-3), 5.54-5.48 (m, 2H, H4; H7), 5.35 (ddd, J=7.5, 4.4, 3.1 Hz, 1H, H-8), 4.65 (dd, J=12.3, 3.1 Hz, 1H, H-9$_a$), 4.40 (dd, J=7.8, 5.1 Hz, 2H, H-6; H-5), 4.20 (dd, J=12.3, 7.3 Hz, 1H, H-9$_b$), 3.81 (s, 3H, OMe), 2.13 (s, 3H, Me, Ac), 2.08 (s, 3H, Me, Ac), 2.07 (s, 3H, Me, Ac), 2.06 (s, 3H, Me, Ac), 1.93 (s, 3H, Me, Ac). $^{13}$C NMR (101 MHz, CDCl$_3$) δ 170.82 (CO, Ac), 170.61 (CO, Ac), 170.19 (CO, Ac), 170.17 (CO, Ac), 161.63 (C-1), 145.06 (C-2), 107.98 (C-3), 76.64 (C-6), 70.85 (C-8), 68.03 (C-7), 67.64 (C-4), 61.97 (C-9), 52.57 (OMe), 46.46 (C-5), 23.09 (Me, Ac), 20.85 (Me, Ac), 20.76 (Me, Ac), 20.72 (Me, Ac), 20.70 (Me, Ac). HRMS (m/z): [M+Na]$^+$ calcd for C$_{20}$H$_{27}$NO$_{12}$, 496.1431; found, 496.1430.

Reference Compound: Methyl 5-(acetamido)-2,4,7,8,9-penta-O-acetyl-3,5-dideoxy-3-fluoro-D-glycero-β-galacto-non-2-ulopyranosonate (27)

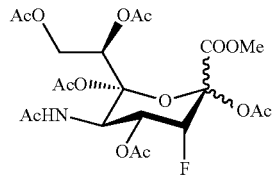

Sialic acid glycal 26 (1.5 g, 3.17 mmol) was solved in DMF (23.8 ml) and H$_2$O (7.9 ml; 0.1 M). Selectfluor (3.37 g, 9.51 mmol; 3 eq.) was added and the reaction was heated to 60° C. for 16 hours, then concentrated in vacuo. Note: Longer reaction times did in our hands not increase the conversion but led to the formation of side-products. The compound was redissolved in EtOAc washed with sat. aq. NaHCO$_{O3}$, dried with MgSO$_4$, filtered, concentrated in vacuo. TLC: (Acet:DCM, 30:70 v/v) $R_f$=0.40. HRMS (m/z): [M+Na]$^+$ calcd for C$_{20}$H$_{28}$FNO$_{13}$, 532.1443; found, 532.1442. The crude fluorinated alcohol was dissolved in Pyr (14.5 ml) and Ac$_{2O}$ (7.3 ml), stirred for 16 hours at r.t. and was evaporated in vacuo. The resulting solid dissolved in EtOAc and sat. aq. NaHCO$_{O3}$. The organic phase was separated and the solvent evaporated in vacuo and purified on silica flash-column chromatography (0→30% ACE in DCM) affording 27 (1.46 g, 2.54 mmol, 80% yield two steps) as a slightly yellow foam. TLC: (Acet:DCM, 30:70 v/v) $R_f$=0.55. $^1$H-NMR (500 MHz, CD$_3$OD, major anomer) δ 5.58 (d, J=8.9 Hz, 1H, NH), 5.46 (dd, J=27.9, 10.7 Hz, 1H, H-4), 5.29 (dd, J=5.0, 1.8 Hz, 1H, H-7), 5.05 (ddd, J=6.7, 5.2, 2.5 Hz, 1H, H-8), 4.87 (dd, J=49.1, 2.5 Hz, 1H, H-3), 4.51 (dd, J=12.5, 2.5 Hz, 1H, H-9$_a$), 4.21-4.10 (m, 3H, H-9$_b$; H-5; H-6), 3.77 (s, 3H, OMe), 2.12-2.09 (m, 6H, 2×Me, OAc), 2.04 (s, 3H, Me, OAc), 1.98 (s, 3H, Me, OAc), 1.97 (s, 3H, Me, OAc), 1.85 (s, 3H, Me, NHAc); $^{13}$C-NMR (126 MHz, CD$_3$OD) δ 170.58 (CO, Ac), 170.56 (CO, Ac), 170.50 (CO, Ac), 170.34 (CO, Ac), 167.11 (C-1), 95.16 (d, J=28.8 Hz, C-2), 86.95 (d, J=185.3 Hz, C-3), 71.91 (C-6), 71.37 (C-8), 68.40 (d, J=17.2 Hz, C-4), 67.93 (C-7), 62.09 (C-9), 53.49 (OMe), 45.53 (C-5), 29.27 (Me, Ac), 20.88 (Me, Ac), 20.79 (Me, Ac), 20.74 (Me, Ac), 20.65 (Me, Ac), 20.51 (Me, Ac); HRMS (m/z): [M+Na]$^+$ calcd for $C_{22}H_3FNO_{14}$, 574.1548; found, 574.1548.

Methyl 5-(S-ethylthiocarbamado)-2,4,7,8,9-penta-O-acetyl-3,5-dideoxy-3-fluoro-D-glycero-β-galacto-non-2-ulopyranosonate (28)

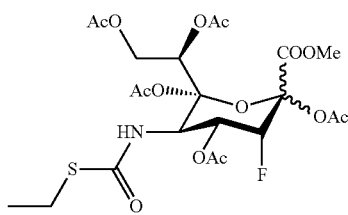

28

Boc inhibitor 9 (0.1 mmol) was dissolved in acetonitrile (1 ml; 0.1M) and trimethysilyl iodide (0.15 mmol; 1.5 eq.) was added. The mixture was stirred at rt. for 2 hrs. The mixture was concentrated in vacuo. The residue was dissolved in $CH_2Cl_2$ (1 ml; 0.1M) and DIPEA (0.4 mmol; 4 eq.), followed by S-ethylchlorothioformate (0.4 mmol; 4 eq.), were added. The reaction was stirred for 16 h at rt after which the mixture was diluted with $CH_2Cl_2$ and washed with 0.1M HCl and sat. $NaHCO_3$. The water layer was extracted twice with $CH_2Cl_2$. The combined organic layers were dried over $MgSO_4$ and concentrated in vacuo. Silicagel flash column chromatography (0% to 60% EtOAc in heptanes) afforded compound 28 (10 mg; 23%). $^1$H NMR (500 MHz, CDCl$_3$) δ 5.54 (dd, J=27.8, 10.6 Hz, 1H), 5.41 (d, J=8.9 Hz, 1H), 5.34 (dd, J=5.5, 1.9 Hz, 1H), 5.17 (td, J=6.0, 2.5 Hz, 1H), 4.94 (dd, J=49.1, 2.5 Hz, 1H), 4.53 (dd, J=12.4, 2.6 Hz, 1H), 4.28-4.06 (m, 3H), 3.84 (s, 3H), 2.86 (q, J=7.3 Hz, 2H), 2.18 (s, 3H), 2.17 (s, 2H), 2.12 (s, 2H), 2.05 (s, 3H), 2.04 (s, 3H), 1.27 (t, J=7.3 Hz, 3H). $^{13}$C NMR (126 MHz, CDCl$_3$) δ 170.60, 170.33, 170.19, 167.11, 165.03, 95.22, 94.99, 87.86, 86.38, 71.76, 70.95, 68.11, 67.09, 53.49, 47.24, 24.58, 20.84, 20.75, 20.64, 20.55, 15.53. $^{19}$F NMR (470 MHz, CDCl$_3$) δ −209.00 (dd, J=49.0, 28.2 Hz). HR-ESI-TOF/MS (m/z): [M+Na$^+$] calcd. for $C_{23}H_{32}FNO_{14}S$, 620.14252; found, 620.14154.

Methyl 5-N-ethylamidnocarbonyl)-2,4,7,8,9-penta-O-acetyl-3,5-dideoxy-3-fluoro-D-glycero-β-galacto-non-2-ulopyranosonate (29)

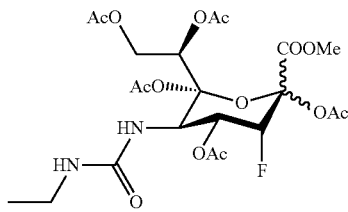

29

Synthesized as described for compound 28, using ethyl isocyanate instead of S-ethylchlorothioformate. Silicagel flash column chromatography (0% to 60% EtOAc in heptanes) afforded compound 29 (14 mg; 35%). H NMR (500 MHz, CDCl$_3$) δ 5.54 (ddd, J=28.4, 11.0, 2.4 Hz, 1H), 5.42 (dd, J=5.0, 2.0 Hz, 1H), 5.14 (ddd, J=7.3, 5.0, 2.5 Hz, 1H), 4.94 (dd, J=49.2, 2.5 Hz, 1H), 4.61-4.57 (m, 2H), 4.51 (d, J=9.1 Hz, 1H), 4.28-4.18 (m, 2H), 4.03 (q, J=10.3 Hz, 1H), 3.84 (s, 3H), 3.13 (dq, J=12.8, 7.2 Hz, 2H), 2.18 (s, 6H), 2.11 (s, 3H), 2.05 (s, 3H), 2.03 (s, 3H), 1.10 (t, J=7.2 Hz, 3H). $^{13}$C NMR (126 MHz, CDCl$_3$) δ 170.77, 170.67, 170.61, 170.46, 167.30, 165.27, 156.82, 95.33, 95.10, 88.00, 86.53, 72.51, 71.51, 69.06, 68.92, 68.24, 62.25, 53.45, 46.45, 35.39, 20.89, 20.83, 20.75, 20.71, 20.56, 15.31. $^{19}$F NMR (470 MHz, CDCl$_3$) δ −208.73 (dd, J=48.9, 28.4 Hz). HR-ESI-TOF/MS (m/z): [M+Na$^+$] calcd. for $C_{23}H_{33}FN_2O_{14}$, 603.18135; found, 603.18059.

Methyl 5-(methylsulfonamido)-2,4,7,8,9-penta-O-acetyl-3,5-dideoxy-3-fluoro-D-glycero-β-galacto-non-2-ulopyranosonate (30)

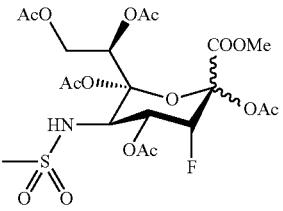

30

Synthesized as described for compound 28, using mesyl chloride instead of S-ethylchlorothioformate. Silicagel flash column chromatography (0% to 60% EtOAc in heptanes) afforded compound 30 (6.6 mg; 24%). $^1$H NMR (500 MHz, CDCl$_3$ δ 5.53 (dd, J=4.7, 1.2 Hz, 1H), 5.47-5.33 (m, 1H), 5.11 (ddd, J=7.1, 4.7, 2.6 Hz, 1H), 4.92 (dd, J=49.0, 2.4 Hz, 1H), 4.62-4.55 (m, 2H), 4.18 (dd, J=12.5, 6.9 Hz, 1H), 4.06-4.01 (m, 2H), 3.85 (s, 3H), 3.02 (s, 3H), 2.21 (s, 3H), 2.18 (s, 3H), 2.16 (s, 3H), 2.06 (s, 3H), 2.05 (s, 1H). $^{13}$C NMR (126 MHz, CDCl$_3$) δ 171.56, 170.88, 170.58, 170.48, 167.02, 164.93, 95.03, 94.80, 87.96, 86.48, 73.05, 71.78, 69.06, 68.92, 67.96, 62.05, 53.57, 48.68, 48.66, 42.54, 21.03, 20.89, 20.79, 20.77, 20.50. $^{19}$F NMR (470 MHz, CDCl$_3$) δ− 208.29 (dd, J=49.1, 27.8 Hz).

Methyl 5-(phenylsulfonamido)-2,4,7,8,9-penta-O-acetyl-3,5-dideoxy-3-fluoro-D-glycero-β-galacto-non-2-ulopyranosonate (31)

31

Synthesized as described for compound 28, using benzenesulfonyl chloride instead of S-ethylchlorothioformate. Silicagel flash column chromatography (0% to 60% EtOAc in heptanes) afforded compound 31 (5.5 mg; 34%). $^1$H NMR (500 MHz, CDCl$_3$ δ 7.92-7.82 (m, 1H), 7.66-7.56 (m, 1H), 7.52 (dd, J=8.4, 6.9 Hz, 1H), 5.47 (dd, J=6.0, 1.5 Hz, 1H), 5.38 (ddd, J=26.9, 11.3, 2.5 Hz, 1H), 5.23 (td, J=5.9, 2.6 Hz, 1H), 5.04 (d, J=7.6 Hz, 1H), 4.95 (dd, J=49.0, 2.5 Hz, 0H), 4.49 (dd, J=12.5, 2.6 Hz, 1H), 4.26-4.19 (m, 1H), 3.84-3.71 (m, 2H), 2.21 (s, 2H), 2.19 (s, 2H), 2.09 (s, 2H), 2.06 (s, 2H), 1.68 (s, 1H). $^{13}$C NMR (126 MHz, CDCl$_3$) δ 171.30, 170.65, 170.46, 170.15, 167.05, 164.90, 141.32, 132.92, 129.18, 127.01, 94.78, 94.55, 87.44, 85.97, 72.61, 70.57, 68.70, 68.07, 67.93, 62.04, 53.46, 49.68, 49.67, 20.87, 20.85, 20.76, 20.50, 20.30. $^{19}$F NMR (470 MHz, CDCl$_3$) δ −210.10 (dd, J=49.1, 26.9 Hz). HR-ESI-TOF/MS (m/z): [M+Na$^+$] calcd. for C$_{26}$H$_{32}$FNO$_{15}$S, 672.13744; found, 672.13539.

Methyl 5-(propylsulfonamido)-2,4,7,8,9-penta-O-acetyl-3,5-dideoxy-3-fluoro-D-glycero-β-galacto-non-2-ulopyranosonate (32)

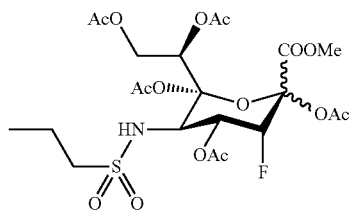

Synthesized as described for compound 28, using 1-propanesulfonyl chloride (1.0 mmol; 10 eq.) instead of S-ethylchlorothioformate (0.4 mmol; 4 eq.). Silicagel flash column chromatography (0% to 60% EtOAc in heptanes) afforded compound 32 (7 mg; 11%). HR-ESI-TOF/MS (m/z): [M+Na$^+$] calcd. for C$_{23}$H$_{34}$FNO$_{15}$S, 638.15309; found, 638.15182.

Example 2—Assay Conditions and Methods

Cell Culture

Mouse B16-F10 melanoma cells (ATCC CRL-6475) were cultured in Minimum Essential Medium (MEM) (Gibco, Invitrogen, Carlsbad, Calif.) containing 5% fetal bovine serum (FBS) (Greiner Bio-one, Frickenhausen, Germany), 1% MEM non-essential amino acids (Gibco), 0.15% sodium bicarbonate (Gibco), 1 mM sodium pyruvate (Gibco), 1.5% MEM vitamins (Gibco), 1% antibiotic-antimycotic solution (50 U/ml penicillin, 50 µg/ml streptomycin and 125 ng/ml amphotericin B) (Gibco). The murine 9464D neuroblastoma cell line was cultured in Dulbecco's Modified Eagle's Medium (DMEM, Glutamax, Gibco) with 10% FBS, 1% non-essential amino acids, 50 µM 2-mercaptoethanol (Sigma-Aldrich) and 1% antibiotic-antimycotic solution (Kroesen et al., 2014, DOI: 10.1002/ijc.28463, Stauffer et al., 2012, DOI: 10.3109/07357907.2012.664670). The murine EL4 T lymphocyte cell line (ATCC TIB-39) was cultured in Iscove's Modified Dulbecco's Medium (IMDM, Gibco) supplemented with 5% FBS and 1% antibiotic-antimycotic solution. Human HEK293 (ATCC CRL-1573) kidney cells and human HeLa (ATCC CCL-2) cervical cancer cells were cultured in DMEM containing 10% FBS, 2 mM glutamine (Lonza, Walkersville, Md.) and 1% antibiotic-antimycotic solution. Human monocytic THP-1 cells (TIB-202, ATCC) were cultured in RRMI-1640 medium (Gibco) supplemented with 10% FBS, 2 mM glutamine and 1% antibiotic-antimycotic solution. All cell lines were cultured in a humidified 5% CO$_2$ incubator at 37° C.

Titration and Long-Term Effect of Fluorine Sialic Acids

To assess the effect of the synthesized compounds on cell surface sialylation, different murine and human cell lines were cultured for three days in the presence of 0-204.8 µM amide and carbamate fluorine sialic acids. Cells treated with an equal final percentage of DMSO were used as control and all cells were subjected to lectin staining and flow cytometry as described below. To investigate the longevity of the effect of the fluorine sialic acids on cell surface sialylation, B16-F10 cells treated with 25.6 µM or 51.2 µM were thoroughly washed with medium to remove fluorine sialic acids from the culture and reseeded. During a period of six days, cells were harvested every day and sialylation was assessed by flow cytometry.

Lectin Staining and Flow Cytometry

For the lectin staining, all cells were harvested and washed with 1× carbo-free blocking solution (Vector Laboratories, Inc., Burlingame, Calif., USA) and stained for 45 minutes at 4° C. in 1× carbo-free blocking solution containing 1 mM CaCl$_2$), 1 mM MgCl$_2$ and biotinylated MALII (5 µg/ml), SNA-1 (1 µg/ml) or PNA (5 µg/ml) all obtained from Vector Laboratories Inc. MALII recognizes α2,3-linked sialic acids, SNA-1 recognizes α2,6-linked sialic acids and PNA binds to terminal 3-galactose. In addition, B16-F10 cells were stained with 2 µg/ml biotinylated AAL (α-linked Fucose), LCA (α-linked Mannose), PHA-L (complex glycans), GSL-I (α-linked Galactose and N-Acetylgalactosamine), WGA (chitobiose), SJA (β-linked Galactose and N-Acetylgalactosamine) and PSA (Glucose and Mannose) purchased from Vector Laboratories Inc. Next, the cells were washed thrice in PBA (1×PBS, 1% BSA, and 0.02% sodium azide) and stained for 10 minutes at 4° C. with 2 µg/ml streptavidin-phycoerythrin (PE) (BD Pharmingen, Franklin Lakes, N.J., USA). The cells were washed thrice again with PBA and fluorescence was assessed using a CyAn ADP flow cytometer (BD Biosciences, San Jose, Calif.) followed by analysis with FlowJo software (Tree Star Inc., Ashland, Oreg.). Untreated cells stained with streptavidin-PE only served as background fluorescence control. The percentages lectin binding was calculated by normalizing the mean fluorescence intensity values from the treated cells with the DMSO controls.

MTT Assay

B16-F10 cells treated for three days with 0.1-204.8 µM fluorine sialic acids or DMSO control were washed with PBS. Next, 60 µl growth medium and 10 µl PBS containing 4 mg/ml Thiazolyl Blue Tetrazolium Blue (MTT) (Sigma-Aldrich, St. Louis, Mo., USA) were added to the cells. The cells were incubated for 30 minutes at 37° C. until blue crystals were clearly detectable inside the cells. Medium was removed and the cells were lysed in 100 µl lysis buffer (isopropanol containing 0.5% SDS, 4% 1N HCl and 3.5% MQ) for 30 minutes at room temperature. Absorbance was measured at 595 nm using an iMark absorbance reader (BioRad, Hercules, Calif., USA).

Statistical Analysis

IC$_{50}$ values and statistics were calculated using Prism 5.03 (GraphPad Software, Inc., La Jolla, Calif.). Statistical significance between the different groups was calculated using one-way ANOVA followed by Bonferroni post-hoc testing and P-values<0.05 were considered significant (p<0.05 *, p<0.01 , p<0.001 *).

Example 3—C-5 Carbamate Sialic Acid Inhibitor are More Potent than the Corresponding C-5 Amide Derivatives The inhibitory potency of 2-14 on the sialic acid biosynthesis was assayed. To this end, B16-F10 cells were fed sialic acid precursors for three day at various concentrations (0.1-204.8 μM). The decrease in cell surface sialylation was measured using biotinylated lectins that are specific for binding α2,3-linked (*Maackia amurensis* Lectin II, MALII) or α2,6-linked (*Sambucus nigra* Lectin, SNA-I) sialic acid residues, subsequently visualized using streptavidin-phycoerythrin. Conversely, binding of the underlying galactose residue uncovered by desialylation was measured using a galactose specific lectin (Peanut, Agglutinin Lectin, PNA). No inhibition was observed without a P-3F$_{ax}$-Neu derivative present. From the concentration dependent inhibition curves, EC$_{50}$ values were extrapolated (FIG. 4). The EC$_{50}$ is defined as the concentration where a 50% decrease in lectin binding is measured. The 5-carbamate derivatives with small substituents proved to be much more potent than the amide derivatives, including the known inhibitor based on natural sialic acid (Ac). The most potent inhibitor showed a 26 fold decrease in EC$_{50}$ for α2,3-inked sialic acid inhibition compared to P-3F$_{ax}$-Neu5Ac. Extended carbamates (—NH—C(=O)—CH$_2$—O— motif) also showed improved potency relative to amide analogues. In addition to the analogues shown in FIG. 1B, the analogues shown below were tested on the same SiaFR scaffold as shown in FIG. 1A.

This scaffold is of compounds according to the invention of general formula (I-ax) wherein each X is acetyl, Z is methyl, L is absent, Q and Q' are both O, and R is variable:

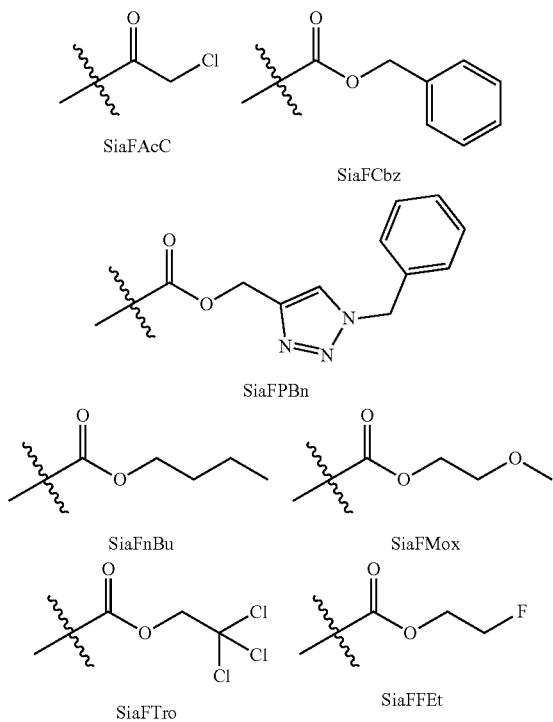

The inhibitors were tested for toxicity (FIG. 5) using the MTT assay. From the results it is clear that larger substituents are worse inhibitors in terms of inhibition and toxicity. Carbamates with smaller hydrophobic alkyl substituents were most potent. In this screen, linear alkyl substituents of α2-3 carbons (7, 8, 10) were best, as including sidechains (11, 12) or 1-carbon substituents (9) gave slightly higher EC$_{50}$ values. The importance of the carbamate was confirmed by an amide homolog (6) of a potent carbamate inhibitor (7), which gave respectively a 44 (MALII) and 22 (SNA-I) times higher EC$_{50}$. Overall, we observed an increased inhibition towards α2,3-linked over α2,6-linked sialic acids. Importantly, the compounds also induce inhibition of sialic acid biosynthesis in cell lines resistant to Ac$_5$SiaNAc-3Fax, namely 9464D cells and EL4 cells (FIG. 6). Tables 1 through 6 show IC50 values of various analogues in different cell lines.

TABLE 1

IC$_{50}$ values (μM) of amide and carbamate fluorine sialic acids in B16-F10 cells.

| Group | Compound | α2,3-Sia IC$_{50}$ | α2,6-Sia IC$_{50}$ |
|---|---|---|---|
| Amides | SiaFAc | 26.79 ± 5.72 | 32.80 ± 3.08 |
| | SiaFTFA | 14.32 ± 0.77 | 33.33 ± 2.63 |
| | SiaFAz | 19.94 ± 2.08 | 32.82 ± 3.55 |
| | SiaFPen | 40.56 ± 5.67 | 52.49 ± 4.31 |
| | SiaFAcC | 17.98 ± 2.12 | ND |
| Extended carbamates | SiaFGc | 04.98 ± 0.33 | 11.78 ± 2.27 |
| Carbamates | SiaFPoc | 00.72 ± 0.20 | 02.59 ± 0.07 |
| | SiaFAll | 01.39 ± 0.21 | 02.87 ± 0.80 |
| | SiaFMe | 04.89 ± 0.25 | 07.54 ± 1.34 |
| | SiaFEt | 01.78 ± 0.16 | 03.87 ± 1.14 |
| | SiaFiBu | 03.33 ± 0.12 | 15.07 ± 3.70 |
| | SiaFBoc | 03.48 ± 0.56 | 08.21 ± 0.67 |
| | SiaFCbz | 14.46 ± 3.51 | ND |
| | SiaFnBu | 7.45 ± 0.92 | 7.91 ± 1.95 |
| | SiaFMox | 25.49 ± 2.53 | 32.38 ± 1.38 |
| | SiaFTro | 3.83 ± 1.06 | 7.85 ± 2.07 |
| | SiaFFEt | 1.25 ± 1.07 | 2.05 ± 1.29 |

TABLE 2

IC$_{50}$ values (μM) of amide and carbamate fluorine sialic acids in THP-1 cells.

| Group | Compound | α2,3-Sia IC$_{50}$ | α2,6-Sia IC$_{50}$ |
|---|---|---|---|
| Amides | SiaFAc | 08.50 ± 1.54 | 10.87 ± 2.47 |
| | SiaFTFA | 03.30 ± 1.26 | 07.19 ± 3.60 |
| | SiaFAz | 10.93 ± 1.98 | 13.23 ± 3.02 |
| | SiaFPen | 10.39 ± 2.14 | 12.58 ± 3.51 |
| Extended carbamates | SiaFGc | 04.24 ± 2.00 | 05.94 ± 2.18 |
| Carbamates | SiaFPoc | 00.42 ± 0.90 | 00.44 ± 1.59 |
| | SiaFAll | 00.41 ± 0.73 | 00.38 ± 1.67 |
| | SiaFMe | 01.98 ± 0.91 | 02.65 ± 1.60 |
| | SiaFEt | 00.45 ± 0.74 | 00.37 ± 1.76 |
| | SiaFiBu | 00.50 ± 1.34 | 00.62 ± 1.77 |
| | SiaFBoc | 01.28 ± 1.36 | 01.72 ± 2.30 |

TABLE 3

IC$_{50}$ values (μM) of amide and carbamate fluorine sialic acids in HEK293 cells.

| Group | Compound | α2,3-Sia IC$_{50}$ | α2,6-Sia IC$_{50}$ |
|---|---|---|---|
| Amides | SiaFAc | 45.22 ± 8.30 | 36.69 ± 3.59 |
| | SiaFTFA | 42.75 ± 2.38 | 41.36 ± 10.44 |
| | SiaFAz | 45.55 ± 5.14 | 47.21 ± 2.89 |
| | SiaFPen | 26.24 ± 2.37 | 44.71 ± 4.33 |
| Extended Carbamates | SiaFGc | 53.60 ± 5.25 | 54.06 ± 15.34 |
| Carbamates | SiaFPoc | 01.19 ± 1.47 | 05.42 ± 1.40 |
| | SiaFAll | 01.83 ± 1.19 | 01.68 ± 3.20 |
| | SiaFMe | 03.31 ± 1.24 | 04.77 ± 2.80 |
| | SiaFEt | 02.02 ± 2.72 | 01.57 ± 4.23 |
| | SiaFiBu | 11.42 ± 4.73 | 09.61 ± 4.83 |
| | SiaFBoc | 10.44 ± 4.76 | 28.03 ± 2.57 |

TABLE 4

IC$_{50}$ values (µM) of amide and carbamate fluorine sialic acids in HeLa cells.

| Group | Compound | α2,3-Sia IC$_{50}$ | α2,6-Sia IC$_{50}$ |
|---|---|---|---|
| Amides | SiaFAc | 52.95 ± 3.61 | 34.50 ± 2.18 |
|  | SiaFTFA | 25.54 ± 2.61 | 33.38 ± 4.38 |
|  | SiaFAz | 80.61 ± 3.26 | 42.19 ± 8.42 |
|  | SiaFPen | 62.31 ± 3.91 | 51.23 ± 6.06 |
| Extended carbamates | SiaFGc | 16.61 ± 3.91 | 12.50 ± 2.52 |
| Carbamates | SiaFPoc | 01.65 ± 2.27 | 01.37 ± 0.81 |
|  | SiaFAII | 01.77 ± 1.78 | 02.04 ± 1.40 |
|  | SiaFMe | 06.33 ± 3.26 | 05.23 ± 1.88 |
|  | SiaFEt | 02.02 ± 1.52 | 01.67 ± 1.31 |
|  | SiaFiBu | 05.15 ± 2.40 | 04.32 ± 1.82 |
|  | SiaFBoc | 12.83 ± 1.61 | 20.55 ± 1.95 |

TABLE 5

IC$_{50}$ values (µM) of amide and carbamate fluorine sialic acids in 9464D cells.

| Group | Compound | α2,3-Sia IC$_{50}$ | α2,6-Sia IC$_{50}$ |
|---|---|---|---|
| Amides | SiaFAc | >102.4 | >102.4 |
|  | SiaFTFA | 46.53 ± 4.41 | >102.4 |
|  | SiaFAz | >102.4 | >102.4 |
|  | SiaFPen | >102.4 | >102.4 |
| Extended carbamates | SiaFGc | >102.4 | >102.4 |
| Carbamates | SiaFPoc | 10.70 ± 2.85 | 40.19 ± 6.56 |
|  | SiaFAII | 06.91 ± 3.56 | 09.64 ± 3.93 |
|  | SiaFMe | 18.31 ± 2.67 | 29.60 ± 4.67 |
|  | SiaFEt | 08.91 ± 2.38 | 28.13 ± 5.51 |
|  | SiaFiBu | 24.45 ± 2.95 | 36.15 ± 6.40 |
|  | SiaFBoc | 36.48 ± 3.81 | >102.4 |

TABLE 6

IC$_{50}$ values (µM) of amide and carbamate fluorine sialic acids in EL4 cells.

| Group | Compound | α2,3-Sia IC$_{50}$ | α2,6-Sia IC$_{50}$ |
|---|---|---|---|
| Amides | SiaFAc | >102.4 | >102.4 |
|  | SiaFTFA | >102.4 | >102.4 |
|  | SiaFAz | >102.4 | >102.4 |
|  | SiaFPen | >102.4 | >102.4 |
| Extended carbamate | SiaFGc | >102.4 | >102.4 |
| Carbamates | SiaFPoc | 51.00 ± 8.62 | 51.65 ± 2.62 |
|  | SiaFAII | 39.92 ± 4.95 | 50.9 ± 6.44 |
|  | SiaFMe | 59.18 ± 4.17 | 52.68 ± 5.45 |
|  | SiaFEt | 42.03 ± 11.04 | 50.58 ± 8.84 |
|  | SiaFiBu | 51.82 ± 18.70 | 51.07 ± 8.97 |
|  | SiaFBoc | 54.58 ± 3.22 | 50.31 ± 3.99 |

The effect on total cell surface glycosylation was also assessed. For this, B16-F$_{10}$ cells were treated for three days with 102.4 µM fluorine sialic acids or DMSO control and were stained with a panel of biotinylated lectins and streptavidin-PE. Lectin binding was determined in two independent experiments by flow cytometry. The following lectins were used: MALII (for α2,3Neu5Ac), PNA (for βGal), AAL (for αFuc), LCA (for αMan), PHA-L (for complex glycans), GSL-I (for αGal, αGalNAc), WGA (for chitobiose), SJA (for βGal, βGalNAc), and PSA (for Glc, Man). Only MaLII showed decreased signal (data not shown).

Example 4—C-5 Carbamate Sialic Acid Inhibitors Induce Prolonged Inhibition of the Sialic Acid Biosynthesis The same compounds as in Example 3 were used to assess the duration of the inhibitory effect. Recovery of sialylation was assessed after treatment of cells with amide and carbamate fluorine sialic acid. For this, B16-F10 cells were incubated for three days with 51.2 µM amide or carbamate fluorine sialic acids or DMSO control. Fluorine sialic acids were removed from the culture and the cells were reseeded. During a period of six days, sialylation was assessed daily with flow cytometry by MALII or SNA-I lectins. FIG. 7 shows recovery of α2,3-sialylation or α2,6-sialylation in time presented as mean percentage lectin binding±SEM normalized to control (n=3). Treatment at 25.6 µM showed similar results (data not shown).

Example 5—C-5 Urea, Thiocarbamate, and Sulphonamide Sialic Acid Inhibitors Performance Analogous to example 3, the inhibitory potency of thiocarbamate 28, urea 29, and sulphonamides 30 and 31 on the sialic acid biosynthesis was assayed. To this end, B16-F10 cells were fed sialic acid precursors for three day at various concentrations (0.1-204.8 µM). The decrease in cell surface sialylation was measured using biotinylated lectins that are specific for binding α2,3-linked (MALII) or α2,6-linked (SNA-1) sialic acid residues, subsequently visualized using streptavidin-phycoerythrin. Conversely, binding of the underlying galactose residue uncovered by desialylation was measured using a galactose specific lectin (Peanut, Agglutinin Lectin, PNA). No inhibition was observed without a P-3F$_{ax}$-Neu derivative present (DMSO vehicle control). From the concentration dependent inhibition curves, EC$_{50}$ values were extrapolated (FIG. 8). The EC$_{50}$ is defined as the concentration where a 50% decrease in lectin binding is measured. The urea and thiocarbamate derivatives proved to be comparable to the carbamate, each being superior to the known inhibitor based on natural sialic acid (Ac). Sulphonamides also proved to be viable inhibitors, with methylsulphonamide 30 outperforming the acetate at various concentrations. IC$_{50}$ values are shown in table 7.

TABLE 7

EC$_{50}$ values (µM) of urea, thiocarbamate, and sulphonamide analogues.

| Compound | α2,3-Sia IC$_{50}$ (MAL) | α2,6-Sia IC$_{50}$ (SNA) |
|---|---|---|
| Acetate | 2.165 | 20.88 |
| Carbamate 17 | 0.9291 | 3.915 |
| Thiocarbamate 28 | 1.675 | 4.825 |
| Urea 29 | 4.201 | 4.892 |
| Sulphonamide 30 | 9.899 | — |
| Phenylsulphonamide 31 | Could not be determined | — |

REFERENCES

Adams and Gahl (GeneReviews, 13 Jun. 2003, PMID: 20301643) Almaraz et al., 2012, DOI 10.1002/bit.24363 Angata and Varki, 2002, DOI: 10.1021/cr000407m Bode et al., 2011, doi: 10.1586/erv.10.174 Büll et al., 2013, DOI: 10.1158/1535-7163.MCT-13-0279 Büll et al., 2014, DOI: 10.1016/j.bbcan.2014.07.005 Büll et al., 2014, DOI: 10.1158/0008-5472.CAN-14-0728 Büll et al., 2015, DOI: 10.1021/nn5061964 Büll et al., 2015, DOI: 10.1021/acschembio.5b 00501 Büll et al., 2016, doi: 10.1016/j.tibs.2016.03.007 Burkart et al., 1997, DOI: 10.1021/ja9723904 Burkart et al., 1999, DOI: 10.1039/A9033621 Chao et al., 2008, DOI: 10.1016/j.carres.2008.01.014

Kroesen et al., 2014, DOI: 10.1002/ijc.28463 Ley, 2003, DOI: 10.1016/S1471-4914(03)00071-6 Macauley et al., 2014, doi: 10.1038/nri3737 Pagan et al., 2018, doi: 10.1016/j.cell.2017.11.041 Rillahan et al., 2012, DOI: 10.1038/nchembio.999 Sedlacek and Seiler, 1978, DOI: 10.1007/BF00199623 Stauffer et al., 2012, DOI: 10.3109/07357907.2012.664670 Stencel-Baerenwald 2014, doi: 10.1038/nrmicro3346 Varki and Schauer, 2009, PMID: 20301246 Volkers et al., 2015, DOI: 10.1038/nsmb.3060 Yin et al., 2017, DOI: 10.1002/bit.26291 WO2008/068638/EP2591787A1/WO2016071431/WO2015148915

The invention claimed is:

1. A compound of general formula (I):

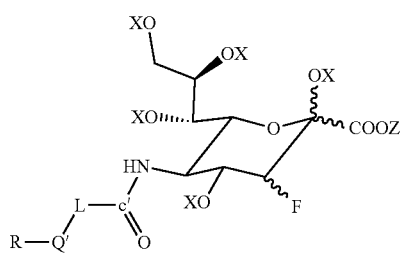

(I)

wherein

X is in each instance independently chosen from the group consisting of hydrogen and a linear, branched, or cyclic $C_{1-6}$ acyl moiety wherein each carbon atom is optionally substituted by a halogen, an alkoxy, or a haloalkoxy moiety, and wherein the acyl chain is optionally unsaturated;

Z is chosen from the group consisting of hydrogen and a linear, branched, or cyclic $C_{1-6}$ alkyl, alkenyl, or alkynyl moiety wherein each carbon atom is optionally substituted by a halogen, an alkoxy, or a haloalkoxy moiety;

Q and Q' are each independently chosen from the group consisting of O, S, and NH;

c' is C;

L is either —CH$_2$— or is absent; and

R is a linear, branched, or cyclic $C_{1-6}$ alkyl, alkenyl, or alkynyl moiety, wherein each carbon atom is optionally substituted by a halogen, an alkoxy, a haloalkoxy, a hydroxyl, or an oxo moiety;

wherein the compound is not of general formula (I) wherein Z is methyl, Q is O, Q' is O, L is absent, R is tert-butyl, X at the anomeric position is axial and is H, and each other X is acetyl.

2. The compound according to claim 1, wherein it is of general formula (II-ax) or (II-eq):

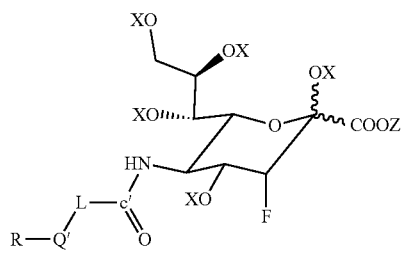

(II-ax)

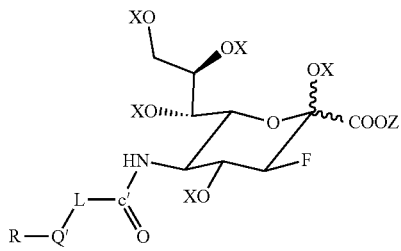

(II-eq)

wherein each of X, Z, Q, Q', c', L, and R are as defined in claim 1.

3. The compound according to claim 1, wherein it is of general formula (III):

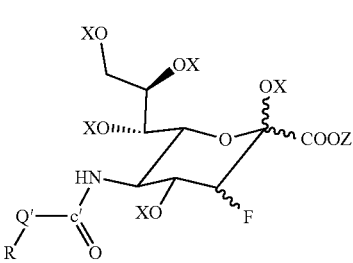

(III)

wherein each of X, Z, Q, Q', c', and R are as defined in claim 1.

4. The compound according to claim 1, wherein

X is in each instance chosen from the group consisting of acetyl, propionyl, and butyryl; and/or Z is chosen from the group consisting of methyl, ethyl, n-propyl, isopropyl, cyclopropyl, allyl, propargyl, n-butyl, tert-butyl, sec-butyl, isobutyl, and cyclobutyl; and/or Q is chosen from the group consisting of O and S; and/or Q' is chosen from the group consisting of O, S, and NH; and/or L is absent; and/or R is a linear, branched, or cyclic $C_{1-6}$ alkyl, alkenyl, or alkynyl moiety, wherein each carbon atom is optionally substituted by a halogen, an alkoxy, a haloalkoxy, a hydroxyl, or an oxo moiety.

5. The compound according to claim 1, wherein

X is acetyl; and/or

Z is methyl; and/or

Q is O; and/or

Q' is O; and/or

L is absent; and/or

R is chosen from the group consisting of methyl, ethyl, isobutyl, tert-butyl, n-butyl, allyl, propargyl, acetyl, 2-methoxyethyl, 2,2,2-trichloroethyl, and 2-fluoroethyl.

6. A method of treating, preventing, or delaying a bacterial infection, viral infection, cancer, a disorder of sialic acid metabolism, or an autoimmune disease in a subject in need thereof, the method comprising administrating to the subject a compound of general formula (I):

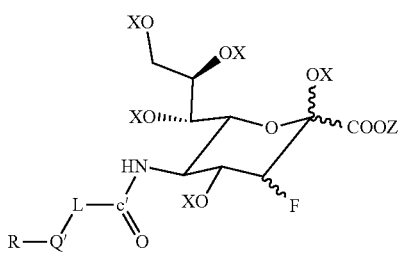

(I)

wherein
X is in each instance independently chosen from the group consisting of hydrogen and a linear, branched, or cyclic $C_{1-6}$ acyl moiety wherein each carbon atom is optionally substituted by a halogen, an alkoxy, or a haloalkoxy moiety, and wherein the acyl chain is optionally unsaturated;
Z is chosen from the group consisting of hydrogen and a linear, branched, or cyclic $C_{1-6}$ alkyl, alkenyl, or alkynyl moiety wherein each carbon atom is optionally substituted by a halogen, an alkoxy, or a haloalkoxy moiety;
Q and Q' are each independently chosen from the group consisting of O, S, and NH;
c' is C;
L is either —CH$_2$— or is absent; and
R is a linear, branched, or cyclic $C_{1-6}$ alkyl, alkenyl, or alkynyl moiety, wherein each carbon atom is optionally substituted by a halogen, an alkoxy, a haloalkoxy, a hydroxyl, or an oxo moiety.

7. A compound of general formula (I):

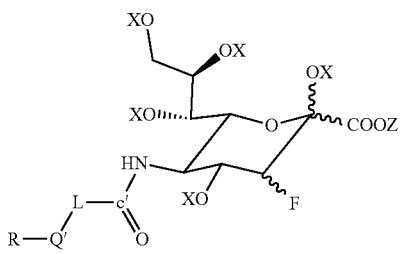

(I)

wherein
c' is S(=O);
X is in each instance independently chosen from the group consisting of hydrogen and a linear, branched, or cyclic $C_{1-6}$ acyl moiety wherein each carbon atom is optionally substituted by a halogen, an alkoxy, or a haloalkoxy moiety, and wherein the acyl chain is optionally unsaturated;
Z is chosen from the group consisting of hydrogen and a linear, branched, or cyclic $C_{1-6}$ alkyl, alkenyl, or alkynyl moiety wherein each carbon atom is optionally substituted by a halogen, an alkoxy, or a haloalkoxy moiety;
Q is O and Q' is absent or is chosen from the group consisting of O, S, and NH;
L is either —CH$_2$— or is absent; and
R is a linear, branched, or cyclic $C_{1-6}$ hydrocarbon moiety, wherein each carbon atom is optionally substituted by a halogen, an alkoxy, a haloalkoxy, a hydroxyl, or an oxo moiety, or optionally R is H when L is absent and Q' is not absent.

8. The compound according to claim 7, wherein it is of general formula (II-ax) or (II-eq):

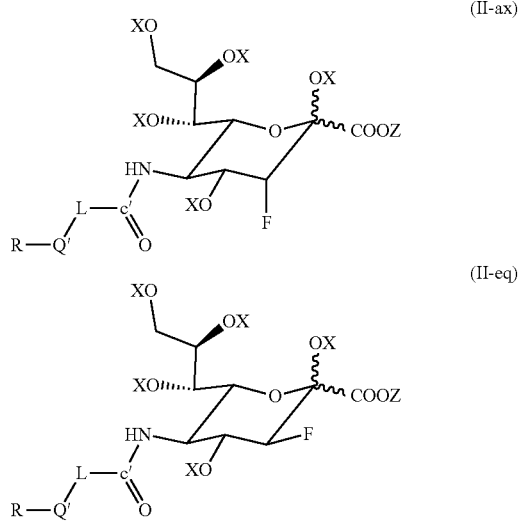

wherein each of X, Z, Q, Q', c', L, and R are as defined in claim 7.

9. The compound according to claim 7, wherein it is of general formula (III):

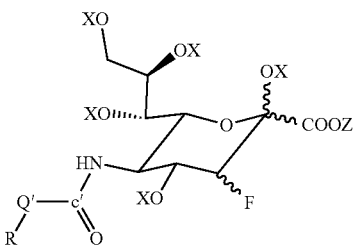

(III)

wherein each of X, Z, Q, Q', c', and R are as defined in claim 7.

10. The compound according to claim 7, wherein
X is in each instance chosen from the group consisting of acetyl, propionyl, and butyryl; and/or
Z is chosen from the group consisting of methyl, ethyl, n-propyl, isopropyl, cyclopropyl, allyl, propargyl, n-butyl, tert-butyl, sec-butyl, isobutyl, and cyclobutyl; and/or
Q is chosen from the group consisting of O and S; and/or
Q' is chosen from the group consisting of O, S, and NH; and/or
L is absent; and/or
R is a linear, branched, or cyclic $C_{1-6}$ alkyl, alkenyl, or alkynyl moiety, wherein each carbon atom is optionally substituted by a halogen, an alkoxy, a haloalkoxy, a hydroxyl, or an oxo moiety.

11. The compound according to claim 7, wherein
X is acetyl; and/or
Z is methyl; and/or
Q is O; and/or
Q' is O; and/or
L is absent; and/or R is chosen from the group consisting of methyl, ethyl, isobutyl, tert-butyl, n-butyl, allyl, propargyl, acetyl, 2-methoxyethyl, 2,2,2-trichloroethyl, and 2-fluoroethyl.

12. A method of treating or delaying a bacterial infection, viral infection, cancer, a disorder of sialic acid metabolism, or an autoimmune disease in a subject in need thereof, the method comprising administrating to the subject a compound of general formula (I):

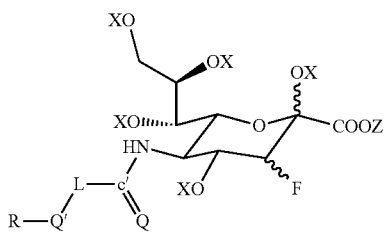

wherein c' is S(=O);

X is in each instance independently chosen from the group consisting of hydrogen and a linear, branched, or cyclic $C_{1-6}$ acyl moiety wherein each carbon atom is optionally substituted by a halogen, an alkoxy, or a haloalkoxy moiety, and wherein the acyl chain is optionally unsaturated;

Z is chosen from the group consisting of hydrogen and a linear, branched, or cyclic $C_{1-6}$ alkyl, alkenyl, or alkynyl moiety wherein each carbon atom is optionally substituted by a halogen, an alkoxy, or a haloalkoxy moiety;

Q is O and Q' is absent or is chosen from the group consisting of O, S, and NH;

L is either —$CH_2$— or is absent; and

R is a linear, branched, or cyclic $C_{1-6}$ hydrocarbon moiety, wherein each carbon atom is optionally substituted by a halogen, an alkoxy, a haloalkoxy, a hydroxyl, or an oxo moiety, or optionally R is H when L is absent and Q' is not absent.

* * * * *